(12) United States Patent
Reiserer et al.

(10) Patent No.: US 11,746,317 B2
(45) Date of Patent: Sep. 5, 2023

(54) MASSIVELY PARALLEL, MULTIPLE-ORGAN PERFUSION CONTROL SYSTEM

(71) Applicant: VANDERBILT UNIVERSITY, Nashville, TN (US)

(72) Inventors: Ronald S. Reiserer, Nashville, TN (US); Gregory B. Gerken, Nashville, TN (US); David K. Schaffer, Nashville, TN (US); John P. Wikswo, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 17/984,151

(22) Filed: Nov. 9, 2022

(65) Prior Publication Data
US 2023/0121352 A1 Apr. 20, 2023

Related U.S. Application Data

(63) Continuation-in-part of application No. 17/947,302, filed on Sep. 19, 2022, which is a continuation of
(Continued)

(51) Int. Cl.
*C12M 1/00* (2006.01)
*C12M 1/24* (2006.01)
(Continued)

(52) U.S. Cl.
CPC ............ *C12M 29/10* (2013.01); *C12M 23/08* (2013.01); *C12M 23/10* (2013.01); *C12M 23/12* (2013.01);
(Continued)

(58) Field of Classification Search
CPC ...... C12M 29/10; C12M 23/08; C12M 23/10; C12M 23/12; C12M 23/16; C12M 23/50;
(Continued)

(56) References Cited

U.S. PATENT DOCUMENTS

| 4,858,883 A | * | 8/1989 | Webster | ................ F16K 11/022 137/884 |
| 5,876,190 A | * | 3/1999 | Spring | .................. F04B 53/007 417/454 |

(Continued)

FOREIGN PATENT DOCUMENTS

| EP | 3190172 A3 | 8/2017 |
| EP | 3415611 A1 | 12/2018 |

(Continued)

OTHER PUBLICATIONS

Watson, D E, Hunziker, R, and Wikswo, J P. Fitting tissue chips and microphysiological systems into the grand scheme of medicine, biology, pharmacology, and toxicology. Exp. Biol. Med., 242:1559-1572. 2017. PMCID: PMC5661772.
(Continued)

*Primary Examiner* — Minh Q Le
(74) *Attorney, Agent, or Firm* — Locke Lord LLP; Tim Tingkang Xia, Esq.

(57) ABSTRACT

A fluidic cartridge comprises a fluidic disk having a plurality of alignment openings; a fluidic chip comprising a body, one or more channels formed in the body in fluidic communications with input ports and output ports for transferring one or more fluids between the input ports and the output ports, and a plurality of protrusions formed on the body and received in the alignment openings of the fluidic disk for aligning the fluidic chip to the fluidic disk; an actuator operably engaging with the one or more channels for selectively and individually transferring the one or more fluids through the one or more channels from at least one of the
(Continued)

input ports to at least one of the output ports at desired flow rates; and a tube member defining a cylindrical housing for accommodating the fluidic disk, the fluidic chip and the actuator therein.

52 Claims, 36 Drawing Sheets

Related U.S. Application Data application No. 17/578,966, filed on Jan. 19, 2022, now Pat. No. 11,447,734, application No. 17/984,151 is a continuation-in-part of application No. PCT/US2021/042179, filed on Jul. 19, 2021, and a continuation-in-part of application No. 17/623,350, filed as application No. PCT/US2020/040061 on Jun. 29, 2020, now Pat. No. 11,565,256.

(60) Provisional application No. 63/300,321, filed on Jan. 18, 2022, provisional application No. 63/277,329, filed on Nov. 9, 2021, provisional application No. 63/257,149, filed on Oct. 19, 2021, provisional application No. 63/163,160, filed on Mar. 19, 2021, provisional application No. 63/139,138, filed on Jan. 19, 2021, provisional application No. 63/053,388, filed on Jul. 17, 2020, provisional application No. 62/868,303, filed on Jun. 28, 2019.

(51) Int. Cl.
| | | |
|---|---|---|
| *C12M 1/22* | (2006.01) | |
| *C12M 3/06* | (2006.01) | |
| *C12M 3/04* | (2006.01) | |
| *C12M 1/36* | (2006.01) | |
| *C12M 1/42* | (2006.01) | |
| *C12M 1/32* | (2006.01) | |
| *C12M 1/06* | (2006.01) | |
| *F16K 99/00* | (2006.01) | |

(52) U.S. Cl.
CPC ............ *C12M 23/16* (2013.01); *C12M 23/50* (2013.01); *C12M 23/58* (2013.01); *C12M 27/02* (2013.01); *C12M 27/12* (2013.01); *C12M 35/02* (2013.01); *C12M 35/04* (2013.01); *C12M 41/48* (2013.01); *F16K 99/0013* (2013.01); *F16K 99/0015* (2013.01); *F16K 99/0023* (2013.01); *F16K 99/0028* (2013.01)

(58) Field of Classification Search
CPC ...... C12M 23/58; C12M 27/02; C12M 27/12; C12M 35/02; C12M 35/04; C12M 41/48; F16K 99/0015; F16K 99/0013; F16K 99/0023; F16K 99/0028
USPC ............... 435/289.1; 137/863, 884; 251/331; 417/44.9, 395, 413.1, 477.3, 554
See application file for complete search history.

(56) References Cited

U.S. PATENT DOCUMENTS

| | | | |
|---|---|---|---|
| 7,704,745 B2 | 4/2010 | Baudenbacher et al. | |
| 7,713,733 B2 | 5/2010 | Cliffel et al. | |
| 7,819,636 B2 * | 10/2010 | Huang .................. | F04B 45/043 417/523 |
| 7,887,304 B2 * | 2/2011 | Cai ....................... | F04B 43/026 92/100 |
| 9,006,149 B2 * | 4/2015 | Garcia-Cardena ..... | C12M 23/12 506/10 |
| 9,618,129 B2 | 4/2017 | Block, III et al. | |
| 9,725,687 B2 | 8/2017 | Wikswo et al. | |
| 9,874,285 B2 | 1/2018 | Block, III et al. | |
| 10,023,832 B2 * | 7/2018 | Wikswo ................. | C12M 41/48 |
| 10,078,075 B2 | 9/2018 | Wikswo et al. | |
| 10,444,223 B2 | 10/2019 | Wikswo et al. | |
| 10,487,819 B2 | 11/2019 | Gould et al. | |
| 10,538,726 B2 | 1/2020 | Wikswo et al. | |
| 10,577,574 B2 | 3/2020 | Wikswo et al. | |
| 10,781,809 B2 | 9/2020 | Gould et al. | |
| 11,135,582 B2 | 10/2021 | Schaffer et al. | |
| 11,465,144 B2 | 10/2022 | Schaffer et al. | |
| 2001/0003290 A1 * | 6/2001 | Xu ........................ | F16K 11/022 137/884 |
| 2013/0337565 A1 * | 12/2013 | Banes ..................... | C12M 25/02 435/401 |
| 2014/0004505 A1 * | 1/2014 | Su ........................ | G01N 33/5304 435/7.37 |
| 2017/0276666 A1 * | 9/2017 | Lyons ..................... | C12M 35/04 |
| 2018/0303083 A1 * | 10/2018 | Echeverri ............ | F16K 99/0028 |
| 2019/0048305 A1 * | 2/2019 | De .......................... | C12M 29/10 |
| 2021/0197194 A1 * | 7/2021 | Schaffer .................. | B01L 3/527 |
| 2022/0146017 A1 * | 5/2022 | Hughes ............... | F16K 99/0023 |

FOREIGN PATENT DOCUMENTS

| | | |
|---|---|---|
| WO | 2019231977 A1 | 12/2019 |
| WO | 2020041260 A1 | 2/2020 |
| WO | 2020041357 A2 | 2/2020 |
| WO | 2020264475 A1 | 12/2020 |
| WO | 2022016136 A1 | 1/2022 |

OTHER PUBLICATIONS

LeDuc, P R, Messner, W C, and Wikswo, J P. How do control-based approaches enter into biology? Annu. Rev. Biomed. Eng., 13:369-396. 2011.

King, R D, Whelan, K E, Jones, F M, Reiser, P G K, Bryant, C H, Muggleton, S H, Kell, D B, and Oliver, S G. Functional genomic hypothesis generation and experimentation by a robot scientist. Nature, 427:247-252. 2004.

King, R D, Rowland, J, Oliver, S G, Young, M, Aubrey, W, Byrne, E, Liakata, M, Markham, M, Pir, P, Soldatova, L N, Sparkes, A, Whelan, K E, and Clare, A. The automation of science. Science, 324:85-89. 2009.

King, R D, Rowland, J, Aubrey, W, Liakata, M, Markham, M, Soldatova, L N, Whelan, K E, Clare, A, Young, M, Sparkes, A, Oliver, S G, and Pir, P. The Robot Scientist Adam. Comp, 42:46-54. 2009.

Williams, K, Bilsland, E, Sparkes, A, Aubrey, W, Young, M, Soldatova, L N, De Grave, K, Ramon, J, de Clare, M, Sirawaraporn, W, Oliver, S G, and King, R D. Cheaper faster drug development validated by the repositioning of drugs against neglected tropical diseases. J. R. Soc. Interface, 12: 20141289. 2015.

Coutant, A, Roper, K, Trejo-Banos, D, Bouthinon, D, Carpenter, M, Grzebyta, J, Santini, G, Soldano, H, Elati, M, Ramon, J, Rouveirol, C, Soldatova, L N, and King, R D. Closed-loop cycles of experiment design, execution, and earning accelerate systems biology model development in yeast. Proc. Natl. Acad Sci. U.S.A., 116:18142-18147. 2019.

Kadouri, A, and Spier, R E. Some myths and messages concerning the batch and continuous culture of animal cells. Cytotechnology, 24:89-98. 1997.

Hoskisson, P A, and Hobbs, G. Continuous culture—making a comeback? Microbiol.—SGM, 151:3153-3159. 2005.

Ziv, N, Brandt, N J, and Gresham, D. The Use of Chemostats in Microbial Systems Biology. J. Vis. Exp., 80: e50168. 2013.

Croughan, M S, Konstantinov, K B, and Cooney, C. The Future of Industrial Bioprocessing: Batch or Continuous? Biotechnol. Bioeng., 112:648-651. 2015.

Bielser, J M, Wolf, M, Souquet, J, Broly, H, and Morbidelli, M. Perfusion mammalian cell culture for recombinant protein manufacturing—A critical review. Biotechnol. Adv., 36:1328-1340. 2018.

(56) References Cited

OTHER PUBLICATIONS

Karst, D J, Steinebach, F, and Morbidelli, M. Continuous integrated manufacturing of therapeutic proteins. Curr. Opin. Biotechnol., 53:76-84. 2018.
Monod, J. La technique de culture continue théorie et applications. Ann. Inst. Pasteur (Paris), 79:390-410. 1950.
Novick, A, and Szilard, L. Description of the Chemostat. Science, 112:715-716. 1950.
Novick, A, and Szilard, L. Experiments with the Chemostat on Spontaneous Mutations of Bacteria. Proc. Natl. Acad. Sci., 36:708-719. 1950.
Miller, D R, Schaffer, D K, Neely, M D, McClain, E S, Travis, A R, Block III, F E, McKenzie, J R, Werner, E M, Armstrong, L, Markov, D A, Bowman, A B, Ess, K C, Cliffel, D E, and Wikswo, J P. A bistable, multiport valve enables microformulators creating microclinical analyzers that reveal aberrant glutamate metabolism in astrocytes derived from a tuberous sclerosis patient. Sens. Actuators B Chem., 341: 129972. 2021.
Eklund, S E, Snider, R M, Wikswo, J, Baudenbacher, F, Prokop, A, and Cliffel, D E. Multianalyte microphysiometry as a tool in metabolomics and systems biology. J. Electroanal. Chem., 587:333-339. 2006.
Lima, E A, Snider, R M, Reiserer, R S, McKenzie, J R, Kimmel, D W, Eklund, S E, Wikswo, J P, and Cliffel, D E. Multichamber multipotentiostat system for cellular microphysiometry. Sensors Actuators B: Chem., 204:536-543. 2014. PMCID: PMC4167374.
McKenzie, J R, Cliffel, D E, and Wikswo, J P. Electrochemical monitoring of cellular metabolism. In: Encyclopedia of Applied Electrochemistry. R. Savinell, K. Ota and G. Kreysa, eds. Springer Science+Business Media, New York, pp. 522-528. 2014.
McKenzie, J R, Cognata, A C, Davis, A N, Wikswo, J P, and Cliffel, D E. Real-Time Monitoring of Cellular Bioenergetics with a Multianalyte Screen-Printed Electrode. Anal. Chem., 87:7857-7864. 2015. PMCID: PMC4770793.
Cyr, K J, Avaldi, O M, and Wikswo, J P. Circadian hormone control in a human-on-a-chip: In vitro biology's ignored component? Exp. Biol. Med., 242:1714-1731. 2017. PMCID: PMC5832251.
Unger, M A, Chou, H P, Thorsen, T, Scherer, A, and Quake, S R. Monolithic microfabricated valves and pumps by multilayer soft lithography. Science, 288:113-116. 2000.
Thorsen, T, Maerkl, S J, and Quake, S R. Microfluidic Large-Scale Integration. Science, 298:580-584. 2002.
Enders, J R, Marasco, C C, Wikswo, J P, and McLean, J A. A Dual-Column Solid Phase Extraction Strategy for Online Collection and Preparation of Continuously Flowing Effluent Streams for Mass Spectrometry. Anal. Chem., 84:8467-8474. 2012. PMCID: PMC3518407.
Marasco, C C, Goodwin, C R, Winder, D G, Schramm-Sapyta, N L, McLean, J A, and Wikswo, J P. Systems-level view of cocaine addiction: The interconnection of the immune and nervous systems. Exp. Biol. Med., 239:1433-1442. 2014. PMCID: PMC4216763.
Zhang, X, Romm, M, Zheng, X Y, Zink, E M, Kim, Y M, Burnum-Johnson, K E, Orton, D J, Apffel, A, Ibrahim, Y M, Monroe, M E, Moore, R J, Smith, J N, Ma, J, Renslow, R S, Thomas, D G, Blackwell, A E, Swinford, G, Sausen, J, Kurulugama, R T, Eno, N, Darland, E, Stafford, G, Fjeldsted, J, Metz, T O, Teeguarden, J G, Smith, R D, and Baker, E S. SPE-IMS-MS: An automated platform for sub-sixty second surveillance of endogenous metabolites and xenobiotics in biofluids. Clin. Mass Spectrom., 2:1-10. 2016.
May, J C, Dodds, J N, Kurulugama, R T, Stafford, G C, Fjeldsted, J C, and McLean, J A. Broadscale resolving power performance of a high precision uniform field ion mobility-mass spectrometer. Analyst, 140:6824-6833. 2015. PMCID: PMC4586486.
May, J C, Goodwin, C R, Lareau, N M, Leaptrot, K L, Morris, C B, Kurulugama, R T, Mordehai, A, Klein, C, Barry, W, Darland, E, Overney, G, Imatani, K, Stafford, G C, Fjeldsted, J C, and McLean, J A. Conformational Ordering of Biomolecules in the Gas Phase: Nitrogen Collision Cross Sections Measured on a Prototype High Resolution Drift Tube Ion Mobility-Mass Spectrometer. Anal. Chem., 86:2107-2116. 2014. PMCID: PMC3931330.
Kim, H S, Waqued, S C, Nodurft, D T, Devarenne, T P, Yakovlev, V V, and Han, A. Raman spectroscopy compatible PDMS droplet microfluidic culture and analysis platform towards on-chip lipidomics. Analyst, 142:1054-1060. 2017.
Jahn, I J, Zukovskaja, O, Zheng, X S, Weber, K, Bocklitz, T W, Cialla-May, D, and Popp, J. Surface-enhanced Raman spectroscopy and microfluidic platforms: challenges, solutions and potential applications. Analyst, 142:1022-1047. 2017.
Abu-Absi, N R, Kenty, B M, Cuellar, M E, Borys, M C, Sakhamuri, S, Strachan, D J, Hausladen, M C, and Li, Z J. Real Time Monitoring of Multiple Parameters in Mammalian Cell Culture Bioreactors Using an In-Line Raman Spectroscopy Probe. Biotechnol. Bioeng., 108:1215-1221. 2011.
Whelan, J, Craven, S, and Glennon, B. In situ Raman spectroscopy for simultaneous monitoring of multiple process parameters in mammalian cell culture bioreactors. Biotechnol. Prog., 28:1355-1362. 2012.
Rafferty, C, O'Mahony, J, Burgoyne, B, Rea, R, Balss, K M, and Latshaw, D C. Raman spectroscopy as a method to replace off-line pH during mammalian cell culture processes. Biotechnol. Bioeng., 117:146-156. 2020.
Iversen, J A, Berg, R W, and Ahring, B K. Quantitative monitoring of yeast fermentation using Raman spectroscopy. Anal. Bioanal. Chem., 406:4911-4919. 2014.
Markov, D A, Lillie, E M, Garbett, S P, and McCawley, L J. Variation in diffusion of gases through PDMS due to plasma surface treatment and storage conditions. Biomed. Microdevices, 16:91-96. 2014. PMCID: PMC3945670.
Eklund, S E, Cliffel, D E, Kozlov, E, Prokop, A, Wikswo, J P, Jr., and Baudenbacher, F J. Modification of the CytosensorTM Microphysiometer to Simultaneously Measure Extracellular Acidification and Oxygen Consumption Rates. Anal. Chim. Acta, 496:93-101. 2003.
Velkovsky, M, Cliffel, D, Eklund, S, Eluvathingal, S, Stremler, M A, and Wikswo, J P. Extracting Metabolic Fluxes from Measurements with a Multianalyte MicroPhysiometer. Biophysical Society 49th Annual Meeting, Long Beach, CA, 2005.
Eklund, S E, Thompson, R G, Snider, R M, Carney, C K, Wright, D W, Wikswo, J, and Cliffel, D E. Metabolic discrimination of select list agents by monitoring cellular responses in a multianalyte microphysiometer. Sensors, 9:2117-2133. 2009. PMCID: PMC3345856.
Velkovsky, M, Snider, R, Cliffel, D E, and Wikswo, J P. Modeling the measurements of cellular fluxes in microbioreactor devices using thin enzyme electrodes J. Math. Chem., 49:251-275. 2011 PMCID: PMC3768171.
Byrd, T F, Hoang, L T, Kim, E G, Pfister, M E, Werner, E M, Arndt, S E, Chamberlain, J W, Hughey, J J, Nguyen, B A, Schneibel, E J, Wertz, L L, Whitfield, J S, Wikswo, J P, and Seale, K T. The microfluidic multitrap nanophysiometer for hematologic cancer cell characterization reveals temporal sensitivity of the calcein-AM efflux assay. Sci. Rep., 4: 5117. 2014. PMCID: PMC4038811.
Kwon, T, Prentice, H, De Oliveira, J, Madziva, N, Warkiani, M E, Hamel, J F P, and Han, J. Microfluidic Cell Retention Device for Perfusion of Mammalian Suspension Culture Sci. Rep., 7: 6703. 2017.
Sonmez, U, Jaber, S, and Trabzon, L. Super-enhanced particle focusing in a novel microchannel geometry using inertial microfluidics. J Micromech Microeng., 27: 065003. 2017.
Warkiani, M E, Tay, A K P, Guan, G F, and Han, J. Membrane-less microfiltration using inertial microfluidics. Sci. Rep., 5: 11018. 2015.
Warkiani, M E, Guan, G F, Luan, K B, Lee, W C, Bhagat, A A S, Chaudhuri, P K, Tan, D S W, Lim, W T, Lee, S C, Chen, P C Y, Lim, C T, and Han, J. Slanted spiral microfluidics for the ultra-fast, label-free isolation of circulating tumor cells. Lab Chip, 14:128-137. 2014.
Bosco, B, Paillet, C, Amadeo, I, Mauro, L, Orti, E, and Forno, G. Alternating Flow Filtration as an Alternative to Internal Spin Filter Based Perfusion Process: Impact on Productivity and Product Quality. Biotechnol. Prog., 33:1010-1014. 2017.

(56) References Cited

OTHER PUBLICATIONS

Clincke, M-F, Mölleryd, C, Zhang, Y, Lindskog, E, Walsh, K, and Chotteau, V. Study of a recombinant CHO cell line producing a monoclonal antibody by ATF or TFF external filter perfusion in a WAVE Bioreactor™. BMC Proc., 5: p. 105. 2011.

Karst, D J, Serra, E, Villiger, T K, Soos, M, and Morbidelli, M. Characterization and comparison of ATF and TFF in stirred bioreactors for continuous mammalian cell culture processes. Biochem. Eng. J., 110:17-26. 2016.

Wang, S, Godfrey, S, Ravikrishnan, J, Lin, H, Vogel, J, and Coffman, J. Shear contributions to cell culture performance and product recovery in ATF and TFF perfusion systems. J. Biotechnol., 246:52-60. 2017.

Gorkov, L P. On the Forces Acting on a Small Particle in an Acoustic Field Within an Ideal Fluid. Dokl. Phys., 6:773-775. 1962.

Goddard, G, Martin, J C, Graves, S W, and Kaduchak, G. Ultrasonic particle-concentration for sheathless focusing of particles for analysis in a flow cytometer. Cytometry Part A, 69A:66-74. 2006.

Gencturk, E, Ulgen, K O, and Mutlu, S. Thermoplastic microfluidic bioreactors with integrated electrodes to study tumor treating fields on yeast cells. Biomicrofluidics, 14: 034104. 2020.

Marasco, C C, Enders, J R, Seale, K T, McLean, J A, and Wikswo, J P. Real-time Cellular Exometabolome Analysis with a Microfluidic-mass Spectrometry Platform. PLoS One, 10: e0117685. 2015. PMCID: PMC4344306.

Brown, J A, Pensabene, V, Markov, D A, Allwardt, V, Neely, M D, Shi, M, Britt, C M, Hoilett, O S, Yang, Q, Brewer, B M, Samson, P C, McCawley, L J M, James M., Webb, D J, Li, D, Bowman, A B, Reiserer, R S, and Wikswo, J P. Recreating blood-brain barrier physiology and structure on chip: A novel neurovascular microfluidic bioreactor. Biomicrofluidics, 9: 054124. 2015. PMCID: PMC4627929.

Brown, J A, Codreanu, S G, Shi, M, Sherrod, S D, Markov, D A, Neely, M D, Britt, C M, Hoilett, O S, Reiserer, R S, Samson, P C, McCawley, L J, Webb, D J, Bowman, A B, McLean, J A, and Wikswo, J P. Metabolic consequences of inflammatory disruption of the blood-brain barrier in an organ-on-chip model of the human neurovascular unit. J. Neuroinflammation, 13: 306. 2016. PMCID: PMC5153753.

Brown, J A, Faley, S L, Shi, Y, Hillgren, K M, Sawada, G A, Baker, T K, Wikswo, J P, and Lippmann, E S. Advances in blood-brain barrier modeling in microphysiological systems highlight critical differences in opioid transport due to cortisol exposure. Fluids Barriers CNS, 17: 38. 2020. PMCID: PMC7269003.

May, J C, and McLean, J A. Advanced Multidimensional Separations in Mass Spectrometry: Navigating the Big Data Deluge. Annu. Rev. Anal. Chem., 9:387-409. 2016.

Enders, J R, Marasco, C C, Kole, A, Nguyen, B, Sundarapandian, S, Seale, K T, Wikswo, J P, and McLean, J A. Towards monitoring real-time cellular response using an integrated microfluidics-MALDI/NESI-ion mobility-mass spectrometry platform. IET Syst. Biol., 4:416-427. 2010. PMCID: PMC4254925.

Gutierrez, D B, Gant-Branum, R L, Romer, C E, Farrow, M A, Allen, J L, Dahal, N, Nei, Y W, Codreanu, S G, Jordan, A T, Palmer, L D, Sherrod, S D, McLean, J A, Skaar, E P, Norris, J L, and Caprioli, R M. An Integrated, High-Throughput Strategy for Multiomic Systems Level Analysis. J. Proteome Res., 17:3396-3408. 2018.

Rafferty, C, Johnson, K, O'Mahony, J, Burgoyne, B, Rea, R, and Balss, K M. Analysis of chemometric models applied to Raman spectroscopy for monitoring key metabolites of cell culture. Biotechnol. Prog., 36: e2977. 2020.

Short, K W, Carpenter, S, Freyer, J P, and Mourant, J R. Raman spectroscopy detects biochemical changes due to proliferation in mammalian cell cultures. Biophys. J., 88:4274-4288. 2005.

Ali, A, Abouleila, Y, and Germond, A. An Integrated Raman Spectroscopy and Mass Spectrometry Platform to Study Single-Cell Drug Uptake, Metabolism, and Effects. J. Vis. Exp.: e60449. 2020.

Wolff, A, Perch-Nielsen, I R, Larsen, U D, Friis, P, Goranovic, G, Poulsen, C R, Kutter, J P, and Telleman, P. Integrating advanced functionality in a microfabricated high-throughput fluorescent-activated cell sorter. Lab Chip, 3:22-27. 2003.

Hui, W C, Yobas, L, Samper, V D, Heng, C K, Liw, S, Ji, H, Chen, Y, Cong, L, Li, J, and Lim, T M. Microfluidic systems for extracting nucleic acids for DNA and RNA analysis. Sensors and Actuators A, 133:335-339. 2007.

Gao, J, Yin, X F, and Fang, Z L. Integration of single cell injection, cell lysis, separation and detection of intracellular constituents on a microfluidic chip. Lab Chip, 4:47-52. 2004.

\* cited by examiner

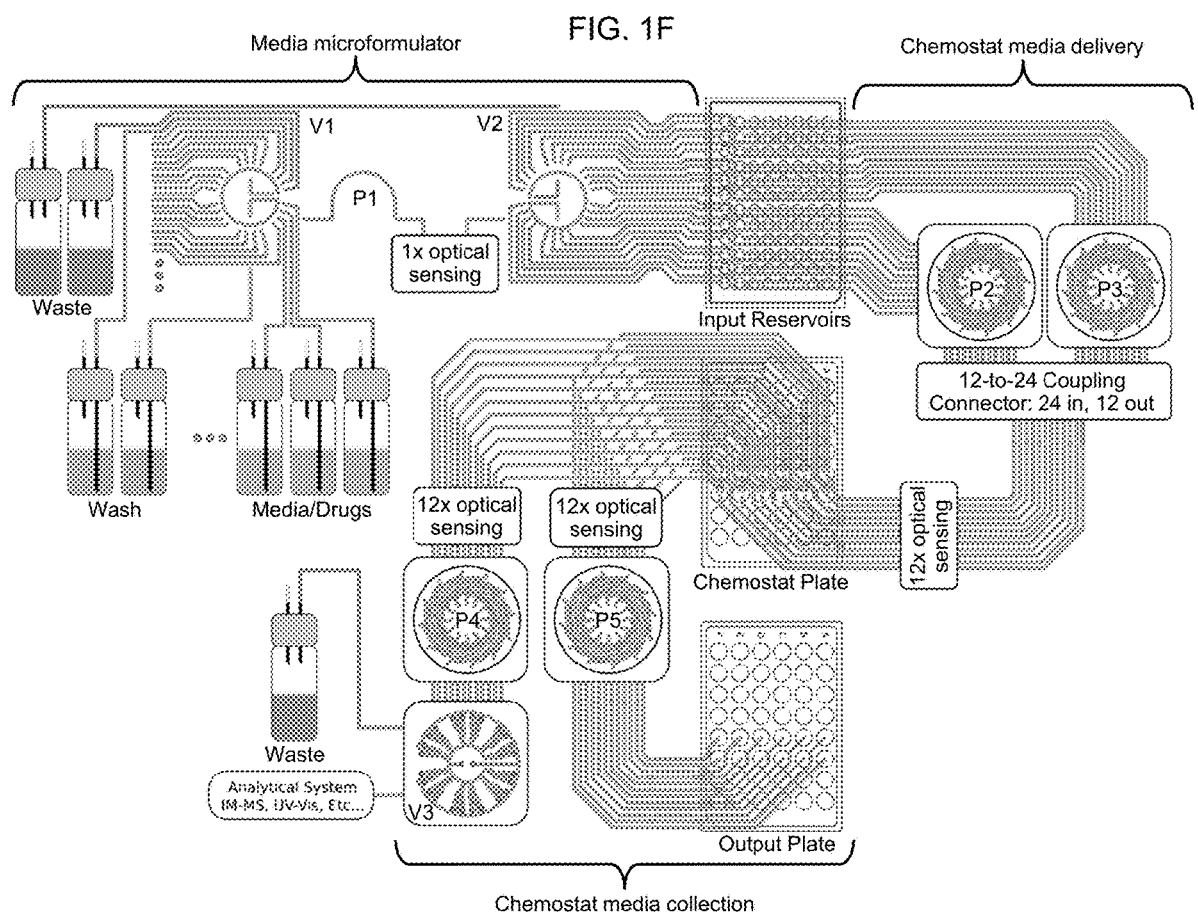

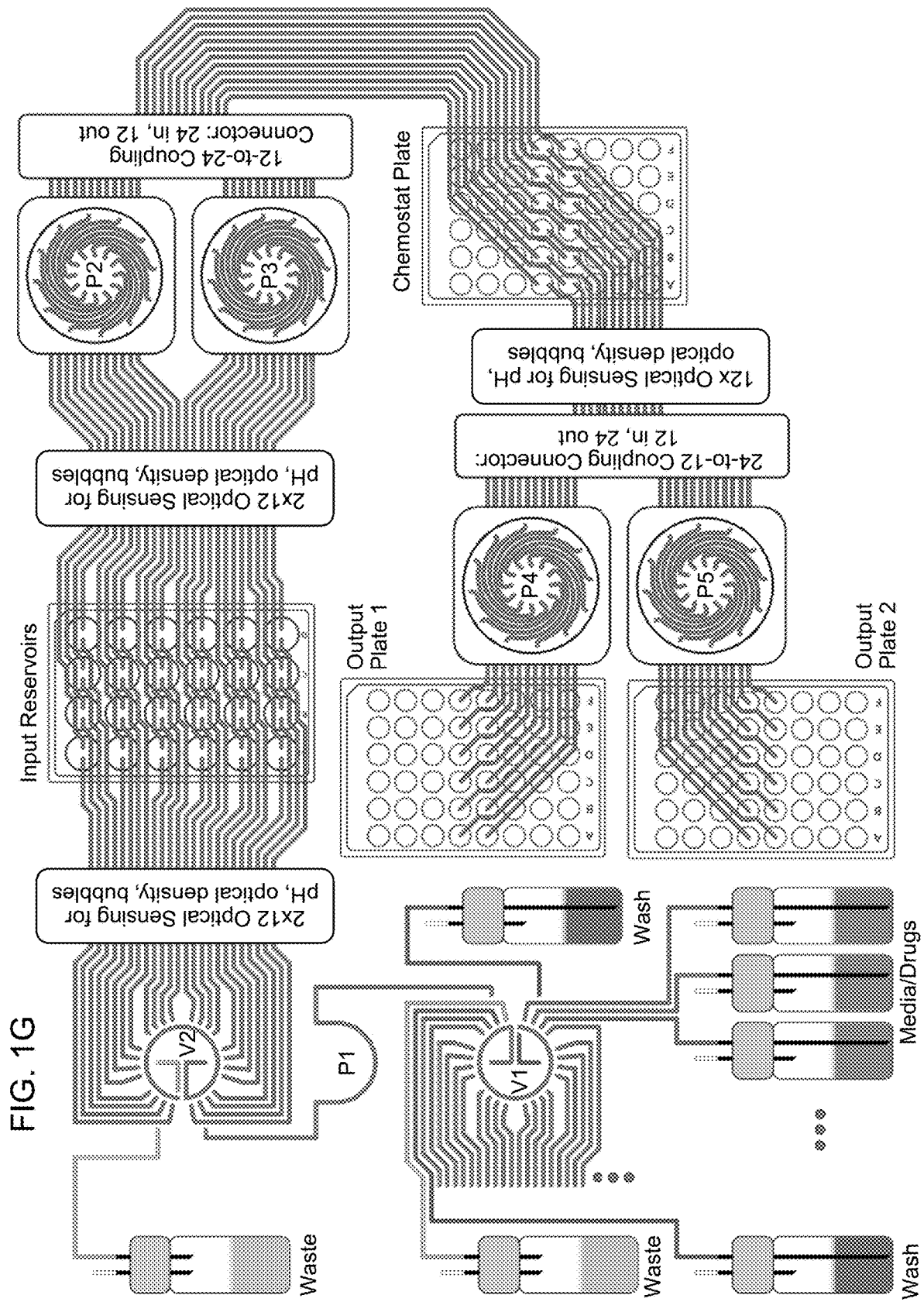

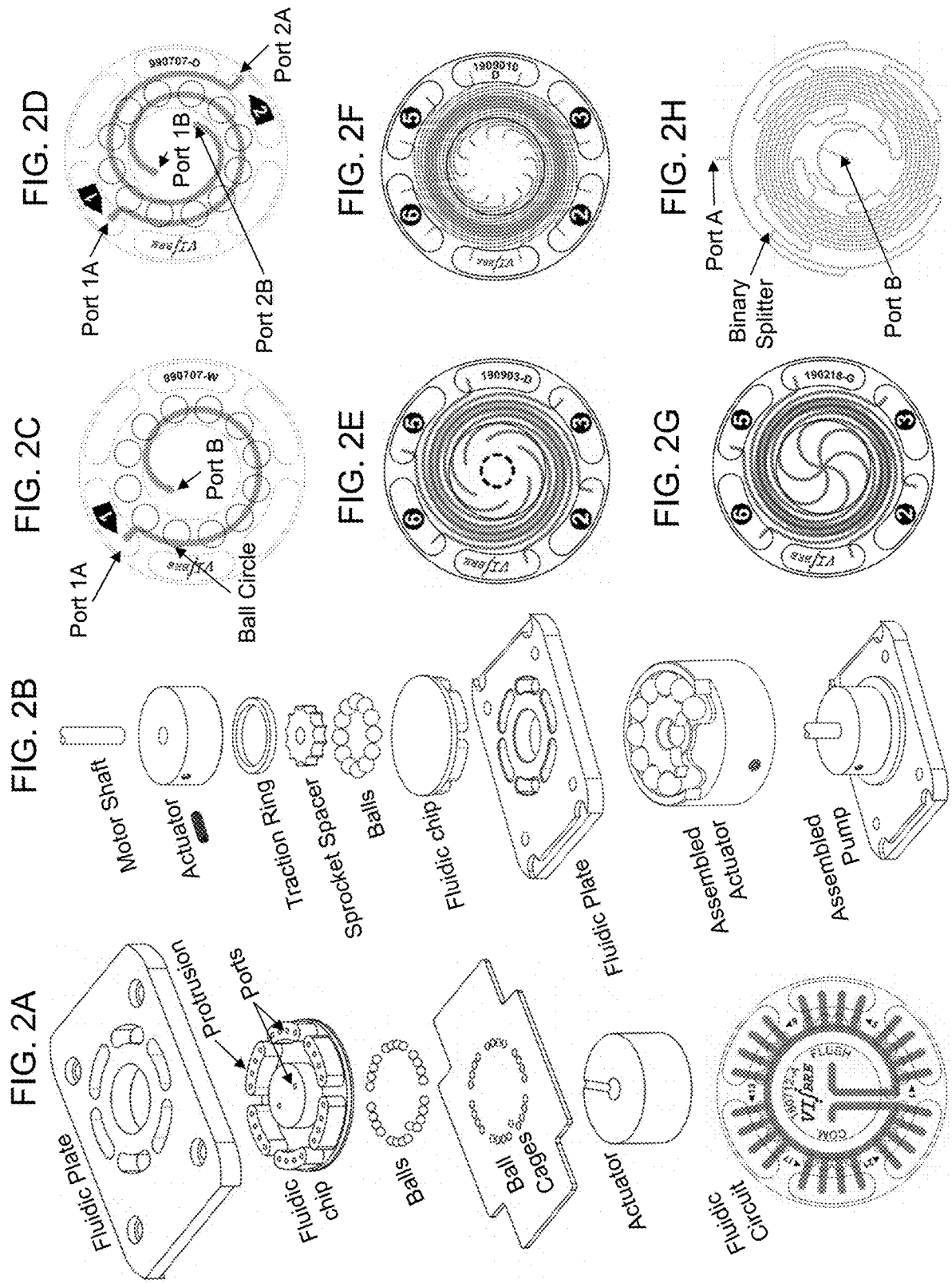

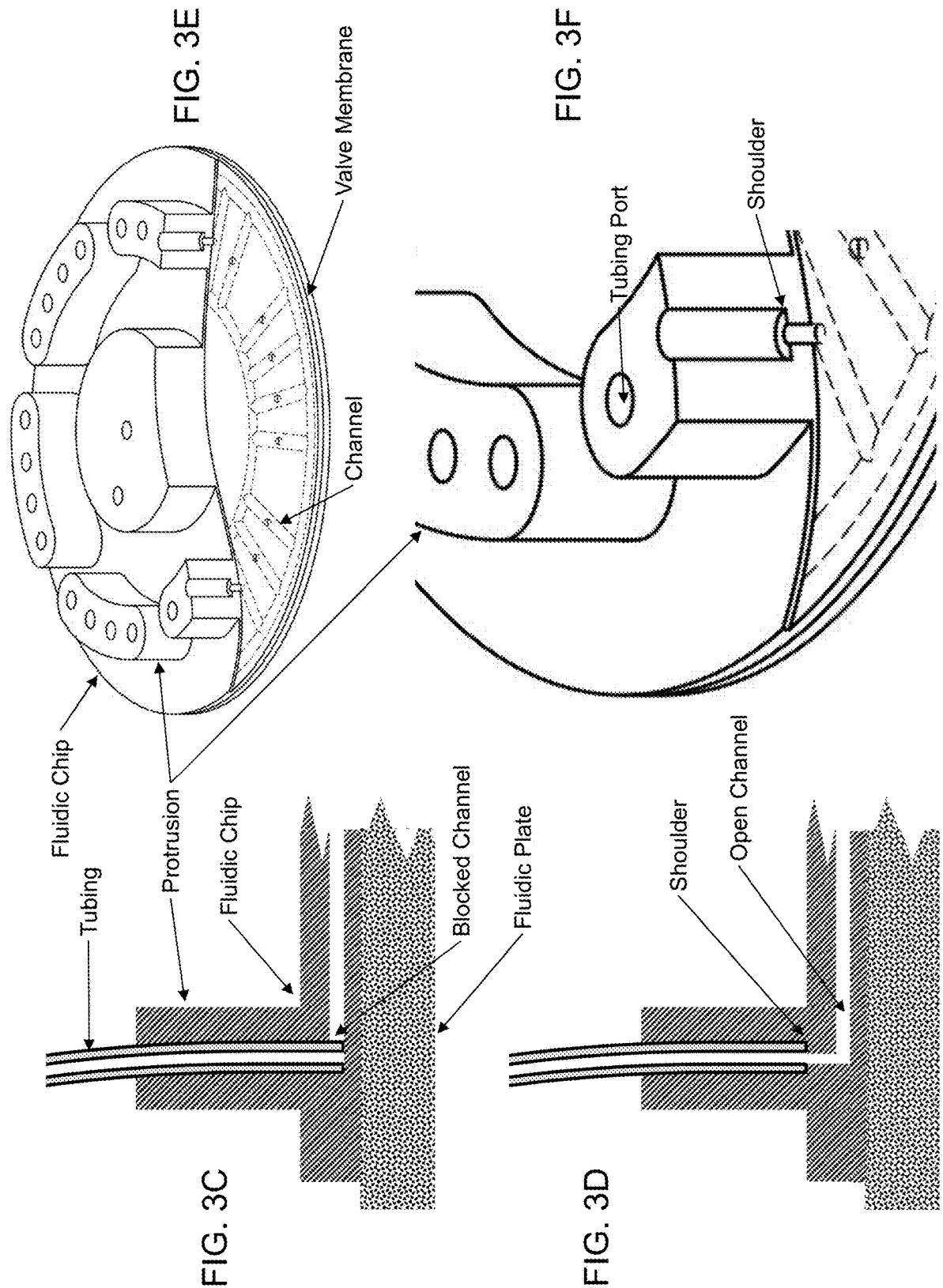

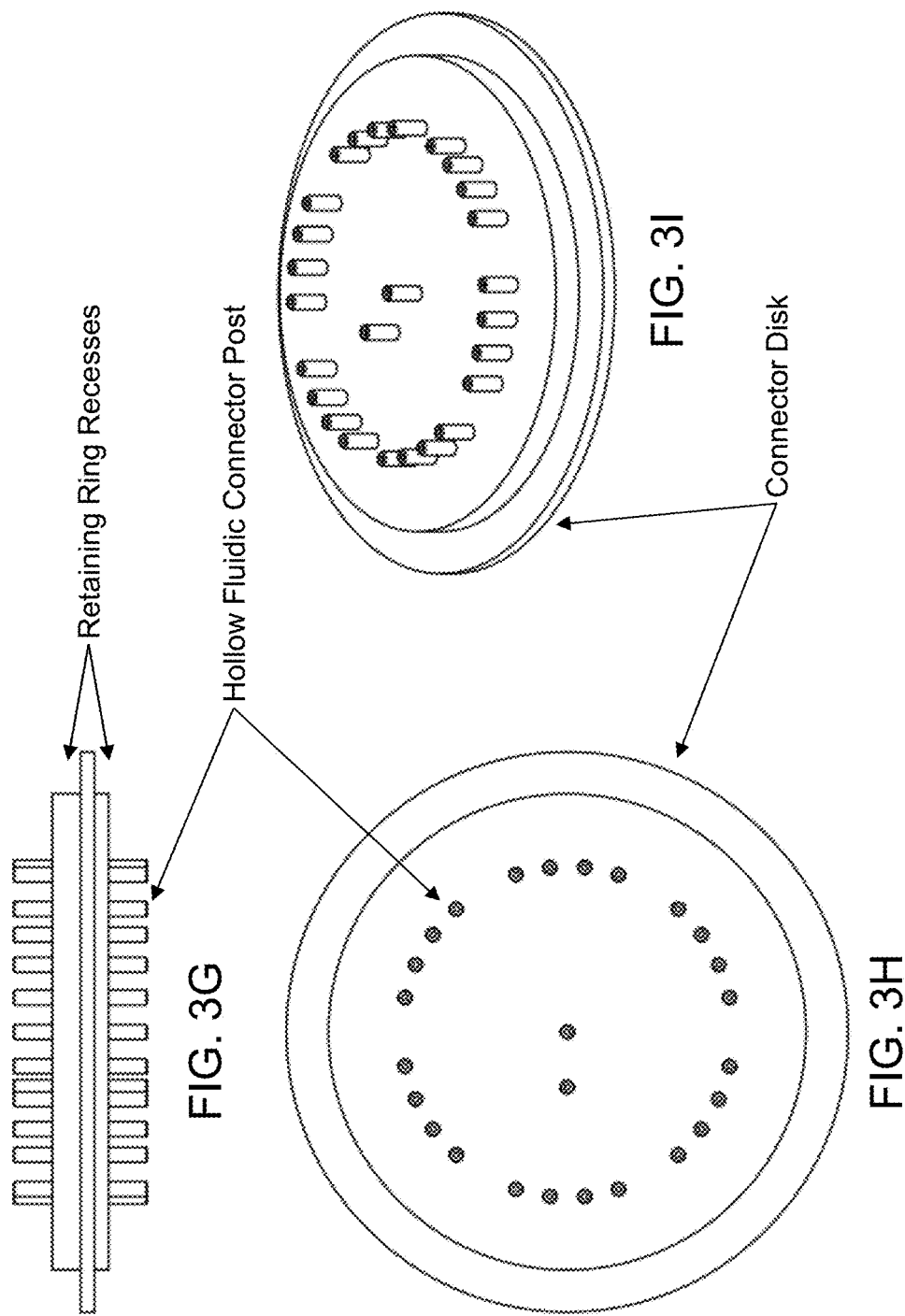

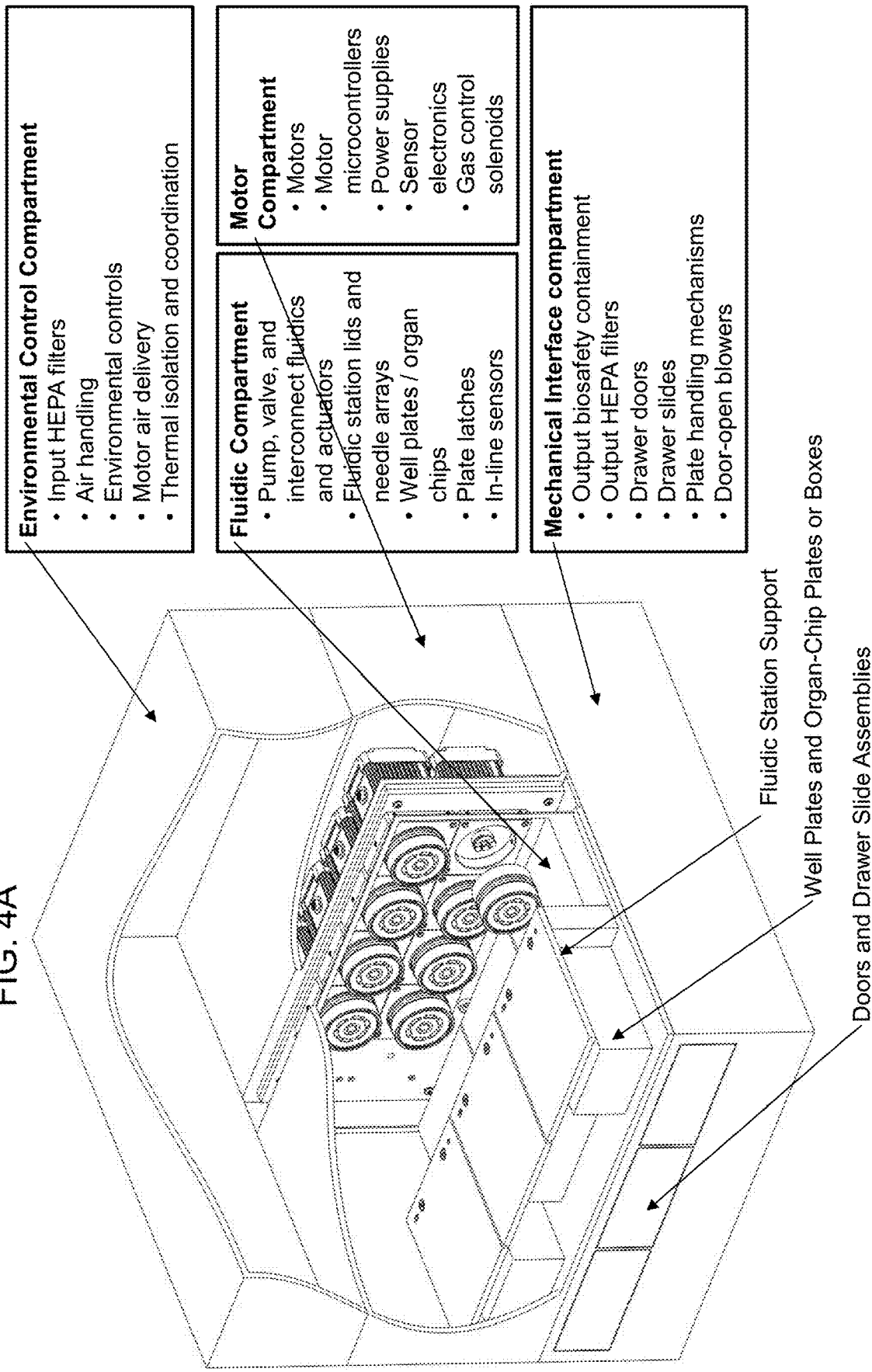

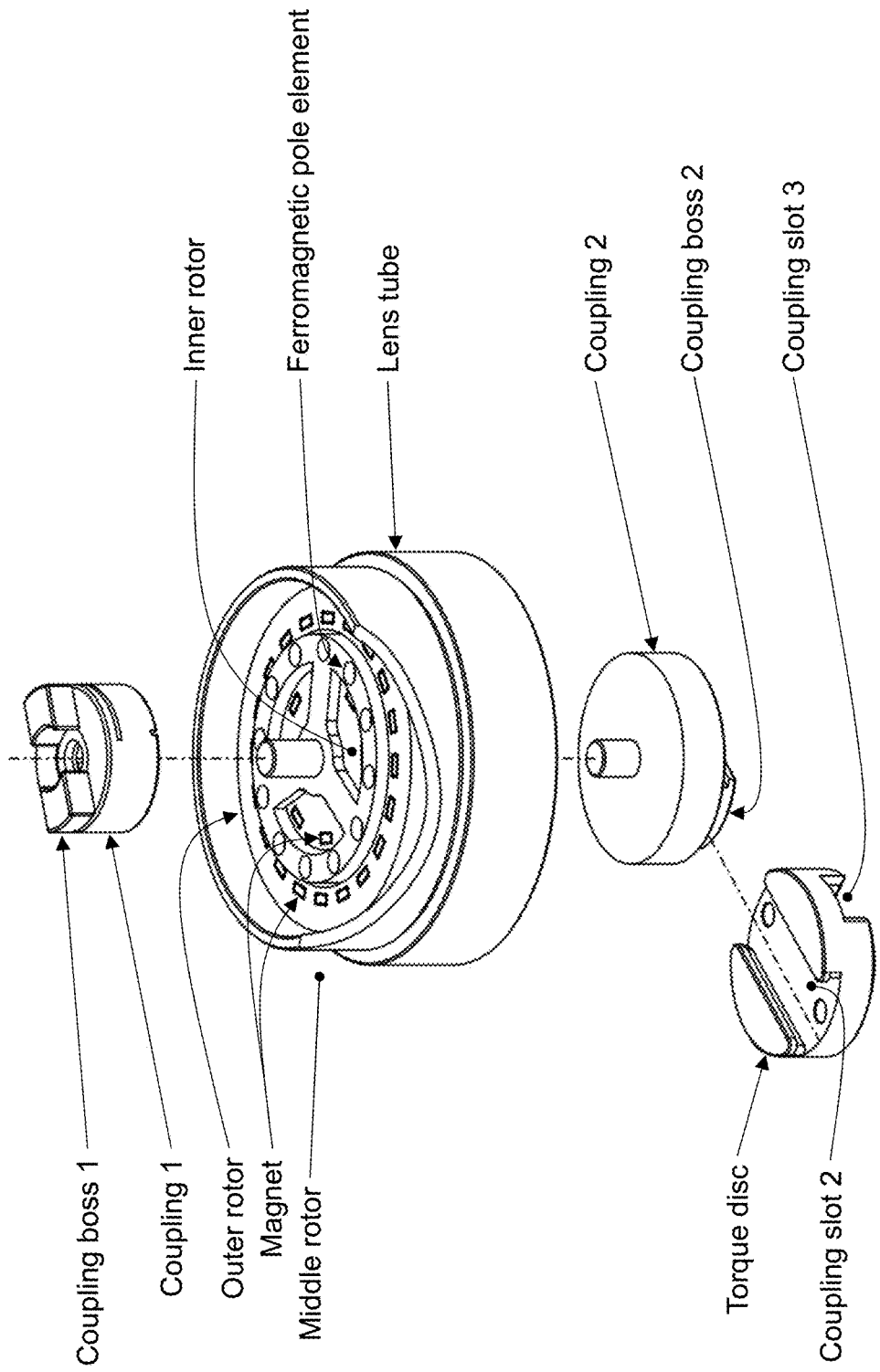

In this example, gear ratio between input and output can be 1:4.33, 1:1.33, or 1:1, depending on which elements are fixed relative to others.

In this example, wherein the sun gear is driving and the upper Oldham feature is fixed to the planet gear, the gear ratio is 6:1

MASSIVELY PARALLEL, MULTIPLE-ORGAN PERFUSION CONTROL SYSTEM

CROSS-REFERENCE TO RELATED PATENT APPLICATIONS

This application claims priority to and the benefit of U.S. Provisional Patent Application Ser. No. 63/277,329, filed Nov. 9, 2021.

This application is a continuation-in-part application of U.S. patent application Ser. No. 17/947,302, filed Sep. 19, 2022, which is a continuation application of U.S. patent application Ser. No. 17/578,966, filed Jan. 19, 2022, now U.S. Pat. No. 11,447,734, which itself claims priority to and the benefit of U.S. Provisional Patent Application Ser. Nos. 63/139,138, filed Jan. 19, 2021, 63/163,160, filed Mar. 19, 2021, 63/257,149, filed Oct. 19, 2021, 63/277,329, filed Nov. 9, 2021, and 63/300,321, filed Jan. 18, 2022.

This application is also a continuation-in-part application of PCT Patent Application Ser. No. PCT/US2021/042179, filed Jul. 19, 2021, which itself claims priority to and the benefit of U.S. Provisional Patent Application Ser. Nos. 63/053,388, filed Jul. 17, 2020; 63/139,138, filed Jan. 19, 2021; and 63/163,160, filed Mar. 19, 2021.

This application is also a continuation-in-part application of U.S. Patent Application Ser. No. 17/623,350, filed Dec. 28, 2021, now allowed, which is a U.S. national entry of PCT Patent Application Ser. No. PCT/US2020/040061, filed Jun. 29, 2020, which itself claims priority to and the benefit of U.S. Provisional Patent Application Ser. No. 62/868,303, filed Jun. 28, 2019.

Each of the above-identified applications is incorporated herein by reference in its entirety.

STATEMENT AS TO RIGHTS UNDER FEDERALLY-SPONSORED RESEARCH

This invention was made with government support under Grant No. UH3TR002097 awarded by the National Institutes of Health (NIH) National Center for Advancing Translational Sciences (NCATS), National Institute of Neurological Disorders and Stroke (NINDS), and Eunice Kennedy Shriver National Institute of Child Health and Human Development (NICHD); Grant Nos. U01TR002383 and (through CFD Research Corporation) HHSN271201700044C awarded by NCATS; by the National Science Foundation (NSF) under Grant No. CBET-1706155 and Grant No. 2117782; and by the National Aeronautics and Space Administration (NASA) under Grant No. 80NSSC20K0108. The government has certain rights in the invention.

FIELD OF THE INVENTION

The invention relates generally to fluidic components, assemblies, and systems required for the control of the perfusion and sampling of multiple organ chips, tissue chips, well plates, chemostats, and other continuous, intermittent, or batch-fed bioreactor systems. These components, assemblies, and systems could be used to create a continuous automated perfusion culture analysis system (CAPCAS) operating as a third-generation "robot scientist" that functions as a fully automated microfluidic system containing 1,000 or more biodevices such as chemostats, bioreactors, organ chips or other biodevices for parallel, independent, long-duration, machine-guided experiments to optimize biological function or infer the dynamics of signaling and metabolism of living systems, such as the single-cell eukaryotic yeast Saccharomyces cerevisiae, bacterial communities, Chinese hamster ovary (CHO) cells used in antibody production, single and coupled organs-on-chips, and other bio-objects that require regular media changes or even continuous perfusion. These fluidic components, assemblies, and systems could also be used to conduct massively parallel biotic and abiotic chemical synthesis experiments.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

The limitations of conventional cell culture on plastic are well recognized, in that the environment in which the cells grow is highly nonphysiological,[1] most notably because the cell culture media is typically changed every day or two so that the cells are almost continuously exposed to an ever-decreasing level of nutrients and increasing levels of metabolites, some of which are cytotoxic, with a rapid replacement of conditioned media with fresh media during which time the cells experience a metabolic and signaling shock. Many times, cell biology experiments are conducted using monolayer monocultures of either immortalized or cancer-derived cell lines, or terminally differentiated primary cells that were dissociated from a specific living organ or tissue or tumor. Hard plastic does not replicate the elastomechanical properties of the extracellular matrix and other tissues upon which cells normally grow in vivo. Frequently, cells that are capable of dividing do so only until they have reached confluence, after which they undergo cell cycle arrest and become senescent.

One of the great advantages of cell culture on plastic is that the culture and testing of cells grown in multi-well plates has been highly automated, typically by using robot arms, automated fluid handlers that operate multi-head pipettes, and centrifuges, plate readers, and other instruments that are compatible with both robot-arm plate handling and pipette fluid handling. However, it is becoming well-recognized that the robot arms and multi-head pipette fluid handlers represent choke points in workflows. For example, the changing of media in a typical well plate undergoing more than one or two days of cell culture requires that the plate is removed from the incubator, the lid removed, media conditioned with metabolites withdrawn from each well and replaced with fresh media or fresh media with the drug being tested, the lid replaced, and the well plate returned to the incubator. This set of operations not only takes time but also exposes the cells to sudden changes in their environment, including levels of nutrients, metabolites, oxygen, and temperature. This intermittent media replacement limits the total number of cells that can be grown in a single well, in that the cells will die if the available nutrients are consumed and metabolic products reach a toxic level.

Many of the limitations of two-dimensional, i.e., flat, biology on plastic have been overcome by the use of continuously perfused microphysiological systems (MPS), which are defined as "fit-for-purpose devices, containing one or more engineered organ(s), organ substructures, and/or functional organ unit(s) in a controllable microenvironment. An MPS represents one or more aspects of the organ or organ system's dynamics, functionality, and/or (patho)physiological response such as responding to biologic, mechanical, electromagnetic (light and/or radiation), or pharmaceutical stimuli in vivo. Ideally, an MPS has the capacity to be monitored under real time. MPS platforms may comprise mono-cultures, co-cultures of multiple cell types, maintenance of explants derived from tissues/organs, and/or inclusion of organoid cell formations," (ASTM (2022). Standard F3570-22, Standard Terminology Relating to Microphysiological Systems. Book of Standards Volume: 13.02, Developed by Subcommittee: F04.43.).[2] The cells cultured in an MPS model can be a superfused cellular monolayer grown on a semipermeable membrane, with media delivery and even another layer of cells on the other side of the membrane. The cultured tissues can be thicker, either through layered or heterogeneous populations of cells grown to a depth that can be supported by superfusion. Other aspects of the limitations of cell culture on plastic are addressed by growing cells in suspension in liquid media or attached to suspended beads, either in batch-fed or perfused bioreactors.

Given their cell density and metabolic activity, microphysiological systems are generally perfused, using either syringe pumps, conventional peristaltic pumps, or elevated reservoirs whose flow is driven by gravity. Syringe pumps require refilling of the syringes, conventional peristaltic pumps are typically large and pulsatile, and the fluid level, and hence flow rate, of a gravity reservoir are always changing and the upper and lower reservoirs require refilling and emptying, respectively. None of these technologies are particularly well suited for the level of massive parallelization that has been achieved using standard well-plate technologies.

In U.S. Pat. Nos. 11,447,734 B2 and 11,474,531 B2, and PCT Patent Application Ser. No. PCT/US2021/042179, which are incorporated herein by reference in their entireties, we have described microfluidic systems that utilize our single- and multi-channel microfluidic pumps and valves, and various configurations of bioreactors. Most notable of these is the Continuous Automated Perfusion Culture Analysis System (CAPCAS) that can provide continuous or intermittent perfusion and/or media exchange for a plurality of chemostats, bioreactors, organs-on-chips, other MPS models, well plates and other bio-objects that support the culture of human and other eukaryotic and prokaryotic cells, including unicellular organisms such as *S. cerevisiae* and *Escherichia coli*. These systems are designed to address the limitations of existing dish, flask, well plate, Transwell, and bioreactor technologies for conventional cell culture technologies. As discussed in detail in U.S. Pat. No. 11,447,734 B2, these systems can be interfaced to conventional automated robot well-plate pipetting and handling systems that are capable of automatic manipulation and measurements of well plates and their transfer between different stations. In some configurations, these microfluidic pumps and valves can be used for long-term maintenance of multiple MPS organ or tissue chips operated in isolation or fluidically coupled together.

The new pump and valve inventions described herein provide a means to support the closed-loop, feed-back sensing and control of the large numbers of in vitro biological systems that will be required to probe the dynamic, non-linear, and redundant signaling and metabolic networks that are the basis for the extreme complexity of biology and are the focus of intense efforts in mathematical modeling.[3] Hence, there is a pressing need for an efficient means to design and conduct the massive number of open- and closed-loop experiments needed to parameterize, validate, and utilize mathematical models of biological signaling and metabolism and to probe and even control biological systems. To date, robot arm and pipetting technologies have been used to create an appropriately equipped self-driving laboratory that utilizes artificial intelligence (AI) and machine learning (ML) to operate as an autonomous robot scientist,[4-8] but the fed-batch mode of operation severely complicates the analysis of data extracted from the systems.

Even in the near term, the exquisite complexity of cellular systems biology models means that developing and evaluating them will require the execution of many millions of hypothesis-led experiments. Only AI systems, coupled with laboratory automation, have the ability to plan, execute, and record such a vast number of experiments.[4] A possible solution to the problem of unravelling the complexity of biology will be to create and utilize robot scientists, which are physically implemented laboratory automation systems that exploit techniques from the field of AI to automatically execute cycles of scientific experimentation: 1) form hypotheses, 2) design and select efficient experiments to discriminate between the hypotheses, 3) physically execute the experiments using laboratory automation equipment, 4) analyze and interpret the data, 5) test the hypotheses, 6) use the results to refine or replace the hypothesis, and 7) repeat the process ad infinitum.[4]

As presented in U.S. Pat. No. 11,447,734 B2, microfluidic pumps and valves that are better suited for this task than are robot arms and multi-head pipettes. The challenge is to devise pumps and valves that have the small size, large number of channels, low cost, and high reliability required for creating a functional and economically viable system that could conduct 1,000 or more simultaneous, independent biological experiments that require continuous or intermittent perfusion and analysis.

We now consider the several embodiments of perfusion systems that could be implemented with the appropriate microfluidic pumps and valves. As an alternative to batch feeding with a pipette, a continuous-flow bioreactor, termed a chemostat, provides a steady supply of food and continuously removes excess yeast or even suspended mammalian cells and their metabolites to maintain steady-state growth. There is an increasing recognition that post-genomic biology and microbial systems biology can benefit from a return to continuous-flow culture systems,[1, 9-14] such as the chemostat shown in FIG. 1A that was invented independently in 1950 by Monod[15] and Novick and Szilard.[16,17] FIG. 1A shows a conventional continuous-flow chemostat. The engineering challenge addressed by this invention is to implement the chemostat shown in FIG. 1A not as a single, stand-alone unit or as part of a set of 4, 16 or 24 units in a single chassis, but in groups of hundreds, a thousand, or more in a format suitable for automated operation as part of a self-driving laboratory or robot scientist.

FIG. 1B shows our microclinical analyzer[18-20] that provides automated calibration of multi-analyte electrochemical sensors, which are prone to drift.[21-25] The microclinical analyzer can also serve as a single-channel microformulator,[18-20, 26, 27] also described in U.S. Pat. Nos. 11,135,582 B2 and 11,465,144 B2 by D. K. Schaffer, et al.,[28, 29] and PCT Patent Application No. PCT/US2021/042179 by J. P. Wikswo, et al.,[30] which are incorporated herein by reference in their entireties.

Building upon this concept, we have shown that rotary planar peristaltic micropumps (RPPMs)[28, 31-35] and rotary planar valves (RPVs)[28, 34, 36-42] can be applied to create multi-well microformulators (FIG. 1C), which use time-division multiplexing to deliver a different, realistic pharmacokinetic (PK) profile of drug concentration versus time to each well of a 96-well plate (inset), and can separately store samples from each well of a 24- or 96-well plate[41-47] (U.S. Pat. Nos. 10,023,832 B2 and 11,465,144 B2, which are incorporated herein by reference in their entireties). The CAPCAS invention involves extending the microformulator concept to a multi-channel system that provides continuous delivery of different media formulations to each well of a multi-well CAPCAS that contains yeast, bacteria, or adherent or non-adherent mammalian cells and provides sensing that includes real-time measurements of optical density, pH, and other process variables as well as using a direct-injection mass spectrometer for at-line solid-phase extraction (SPE) ion mobility-mass spectrometry (IM-MS) analyses with ten-second temporal resolution for untargeted metabolomics.

FIG. 1D illustrates how the concept of the microformulator in FIG. 1C can be used to create a 96-channel chemostat.

FIG. 1E shows how 100 of these units can be connected to create a 9,600-channel chemostat/bioreactor, where pumps and valves provide the means to operate each 96-channel system, and couple these systems to an analysis reservoir and a direct injection mass spectrometer system.

The single, independent chemostat or bioreactor shown in FIG. 1A, the single-channel microclinical analyzer in FIG. 1B, and the 24-well microformulator in FIG. 1C can be readily produced using existing RPPMs and RPVs. It is vastly more challenging to implement the 96 chemostats shown in FIG. 1D, or the 9,600 chemostats in FIG. 1E. Given the ever-growing demand to optimize the biological production of antibodies, proteins, and other biopharmaceuticals, and to understand the complexity of cellular metabolism and signaling, there is a pressing need for compact, low-cost, reliable, sterilizable, and easy-to-maintain high-multiplicity microfluidic pumps and valves.

Therefore, a heretofore unaddressed need exists to address the requirements presented by high-multiplicity assays, chemostats, and bioreactors, as well automated robot scientists that operate as self-driving biological laboratories.

SUMMARY OF THE INVENTION

In view of the aforementioned deficiencies and inadequacies, one aspect of this invention provides a fluidic cartridge. The fluidic cartridge comprises a fluidic disk having a plurality of alignment openings; a fluidic chip comprising a body having a first surface and an opposite, second surface, one or more channels formed in the body in fluidic communications with input ports and output ports for transferring one or more fluids between the input ports and the output ports, and a plurality of protrusions formed on the first surface, wherein the plurality of protrusions are received in the plurality of alignment openings of the fluidic disk for aligning the fluidic chip to the fluidic disk; an actuator operably engaging with the one or more channels at the second surface of the body for selectively and individually transferring the one or more fluids through the one or more channels from at least one of the input ports to at least one of the output ports at desired flow rates; and a tube member defining a cylindrical housing for accommodating the fluidic disk, the fluidic chip and the actuator therein.

In one embodiment, the fluidic cartridge further comprises means for mounting a motor for operably driving the actuator to be activated or deactivated; and means for detachably connecting the motor to the actuator.

In one embodiment, the mounting means comprises a motor plate or motor support structure on which the motor is mounted.

In one embodiment, the fluidic cartridge further comprises an array plate or fluidic module support structure attached to the motor plate or motor support structure for locating the motor.

In one embodiment, the fluidic cartridge is thermally isolated from the motor.

In one embodiment, the fluidic cartridge utilizes alignment pins and sockets to separate and reconnect the motor on the motor plate or motor support structure from the fluidic module on the array plate or fluidic module support structure.

In one embodiment, the fluidic cartridge, once compressed, is inserted into the array plate or fluidic module support structure and held in place with one or more tube retaining screws or other fastening means.

In one embodiment, the tube member comprises a double-threaded tube having a first portion and a second portion extending from the first portion; a threaded lock ring threading onto an exterior surface of the first portion of the double-threaded tube; and a fluidic compression threaded tube threading onto the exterior surface of the first portion of the double-threaded tube and abutting against the threaded lock ring.

In one embodiment, the fluidic cartridge further comprises at least a first threaded retaining ring and a second threaded retaining ring threaded into the fluidic compression threaded tube, such that the fluidic disk is placed between the first threaded retaining ring and the second threaded retaining ring that in turn, is placed between the fluidic disk and the fluidic chip.

In one embodiment, the actuator comprises an actuator bearing assembly placed on the second surface of the fluidic chip; and an actuator body operably engaging with the actuator bearing assembly.

In one embodiment, the fluidic cartridge is a valve cartridge, wherein the actuator bearing assembly comprises a plurality of actuation balls; and an actuation ball cage accommodating the plurality of actuation balls.

In one embodiment, the fluidic cartridge is a pump cartridge, wherein the actuator bearing assembly comprises a plurality of actuation balls; a sprocket accommodating the plurality of actuation balls; a pocket accommodating the plurality of actuation balls; and a traction ring placed on the plurality of actuation balls.

In one embodiment, by the use of the double-threaded tube, the compression of a pump or valve is adjustable simply by rotating the fluidic compression threaded tube and locking it in place with the threaded lock ring.

In one embodiment, the fluidic cartridge further comprises a thrust bearing placed between the motor and the actuator in the housing for supporting a compressive force that is applied by the actuator to the fluidic chip and whose grooves on both surfaces of the thrust bearing races maintain the axial alignment of the actuator.

In one embodiment, the thrust bearing comprises a grooved lower thrust bearing race formed on an upper surface of the actuator body of the actuator; a grooved upper thrust bearing race; a thrust bearing ball cage placed between the lower thrust bearing race and the upper thrust bearing race; a plurality of thrust bearing balls accommodated in the thrust bearing ball cage; and a threaded retaining ring threaded onto an interior surface of the second portion of the double-threaded tube and positioned against the upper thrust bearing race for retaining the thrust bearing as placed in the housing.

In one embodiment, the connecting means comprises a coupling mechanism for operably coupling the fluidic cartridge to the motor, or decoupling the fluidic cartridge from the motor.

In one embodiment, the coupling mechanism comprises an input coupling, a torque disk, and a driven construct.

In one embodiment, the driven construct corresponds to the actuator used directly in the operation of the fluidic cartridge.

In one embodiment, the driven construct is a second coupling that operably mates with yet another coupling, thereby allowing further constructs to be connected to the drivetrain in a daisy chain fashion.

In one embodiment, the coupling mechanism is an Oldham coupling mechanism comprising an Oldham coupling torque disk coupled to the actuator body of the actuator; and an Oldham coupling drive disk coupled between the Oldham coupling torque disk and the motor.

In one embodiment, the torque disk comprises an upper slot that mates with the coupling boss, and a lower t-slot that mates with a t-boss in the driven construct.

In one embodiment, the motor side of the actuator body is provided with an Oldham coupling key having a capture key so that it holds in place the Oldham coupling torque disk when the motor plate is separated from the array plate or fluidic module support structure.

In one embodiment, the coupling mechanism further comprises pairs of magnets that maintain the approximate axial alignment of the coupling of the torque disk to the actuator.

In one embodiment, the fluidic cartridge further comprises an in-line gear reduction adapter operably coupled between the fluidic cartridge and the motor.

In one embodiment, the in-line gear reduction adapter is a mechanical gear reduction adapter comprising a ring gear, sun gear, and a system of planetary gears enclosed within a tubular housing.

In one embodiment, the in-line gear reduction adapter is a magnetic gear reduction adapter comprising an outer magnetic rotor, a rotating ferromagnetic pole element, and an inner magnetic rotor, enclosed within a tubular housing.

In one embodiment, the fluidic chip comprises a one-eight-one pump chip comprising eight spiral channels, each end of which is coupled to a binary splitter network, that are directly, mechanically acted upon by the pump assembly's actuating elements.

In one embodiment, the downstream terminus of each spiral channel is a bifurcation, in which that channel converges with another, similar channel, resulting a 2X channel.

In one embodiment, the 2X channel carrying fluid from two spiral channels during pump operation has a cross-sectional area that equals the sum of the cross-sectional areas of each of its contributing channels, and thereby carrying twice the fluid volume.

In one embodiment, the 2X channel, in turn, converges with another, similar 2X channel to form a 4X channel, whose volumetric flow rate is four times that of a 1X channel, wherein after one more bifurcation, an 8X channel delivers all the fluid being pumped through the chip to a plumbing port, which is used to connect the pump chip to an external conduit including flexible tubing.

In one embodiment, the fluidic network upstream of the spiral channels is configured the same way as the downstream network, wherein an 8X channel begins at a plumbing port, splits into two 4X channels, and so on until the path reaches the spiral channels.

In one embodiment, the fluidic chip utilizes eight parallel pumping channels, each end of which is connected to a binary splitter network.

In one embodiment, the plurality of protrusions is in fluidic communication with the one or more channels through interface ports formed in the plurality of protrusions for allowing connection of external tubing to the fluidic module, wherein the interface ports correspond to the input ports and the output ports.

In one embodiment, each of the interface ports has a shoulder formed with a smaller diameter via within each interface port to prevent tubing from bottoming out against channel floors.

In one embodiment, the fluidic cartridge is fluidically connectable to another cartridge or fluidic device through a fluidic interface connector coupled to the interface ports on the plurality of protrusions.

In one embodiment, the fluidic interface connector is a flexible ribbon connector.

In one embodiment, the fluidic cartridge is in a cylindrical form having an axial symmetry.

In one embodiment, the fluidic cartridge is detachable or separable from the motor.

In one embodiment, the fluidic cartridge is portable, sterilizable replaceable, and/or disposable.

In another aspect, the invention relates to a fluidic system comprising a plurality of fluidic cartridges disposed on a platform, wherein the plurality of cartridges comprises pump cartridges, valve cartridges, or a combination of them.

In another aspect, the invention relates to a continuous perfusion bioreactor, comprising an array of sensing and separation heads containing cell separators and media sensors, wherein each sensing and separation head is in fluidic communication with a well and a well tubing group operably connected to pumps and/or valves. In one embodiment, said pumps and/or valves comprise pump cartridges and/or valve cartridges.

In one embodiment, each sensing and separation head comprises a normal flow filter (NFF), and/or a tangential filter comprising a tangential flow filter (TFF) or an alternating tangential flow filter (ATF).

In one embodiment, the tangential filter is adapted for real-time separation of cells from media while minimizing filter fouling by cells, cell debris, and large molecules, wherein the fouling of the filter membrane is prevented by periodic reversal of one or more pumps.

In one embodiment, each sensing and separation head comprises a cell separator for removing suspended cells from an effluent and returning these cells back to the continuous perfusion bioreactor while removing cell-depleted media to maintain a constant volume in the continuous perfusion bioreactor.

In one embodiment, said cell separator is operably connected between one input pump and two output pumps that control the cell separation and recycling process.

In one embodiment, said cell separator is a microfluidic spiral cell separator.

In one embodiment, each sensing and separation head is in fluidic communication with said well through media/cell delivery tubes, media/cell withdrawal tubes, and emptying tubes for removal of large volumes of cells and media therefrom.

In one embodiment, the well tubing group comprises calibration and input tubes for operably delivering calibration input and media input to said sensing and separation head, a recirculation tube for operably circulating media in said sensing and separation head, and waste and media output tubes for operably removing waste output and media output from said sensing and separation head.

In one embodiment, the array of sensing and separation heads is provided with a plurality of bubble tracking flow meters integrated into the continuous perfusion bioreactor.

In one embodiment, each bubble tracking flow meter comprises two spatially separated pairs of a light-emitting diode (LED) and a photodiode (PD) operably connected between a pump and a valve operating in a coordinated manner for detecting the passage of the bubble and thereby the flow velocity In one embodiment, at least one of the plurality of bubble tracking flow meters is located in one desired position in a fluidic system to measure the flow rate, and hence volume, withdrawn from a single fluidic module.

In one embodiment, the array of sensing and separation heads is provided with a plurality of optical density (OD) measuring devices integrated into the continuous perfusion bioreactor.

In one embodiment, the array of sensing and separation heads is provided with a plurality of optical density (OD) measuring devices integrated into the continuous perfusion bioreactor.

These and other aspects of the invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 1F shows a fluidic schematic for the 12-well microchemostat module. A 48-channel system would have the same topology, except 48 chemostats and pumps, valves, and sensors with proportionally more channels.

FIG. 1G shows an alternative embodiment of a 12-well microchemostat module that has two output plates for off-line sensing and analysis of all chemostat effluent, instead of the single output plate and a sensor valve connected to on-line sensors in FIG. 1F.

FIGS. 2A-2O show construction details of previous versions of pumps and valves that could be used to implement a CAPCAS or other fluidic systems to provide continuous or intermittent perfusion of chemostats, bioreactors, organ chips, or other bio-objects, according to embodiments of the invention, where FIG. 2A shows the sensor valve (V3) shown in FIG. 1F; FIG. 2B shows a rotating planar peristaltic micropump whose actuator contains a groove around which balls roll, with an elastomeric traction ring ensuring that the balls roll rather than slide; FIG. 2C shows a single-channel spiral pump, with the shape of the spiral optimized to minimize peristaltic oscillations and backflow; FIGS. 2D, 2E and 2F respectively show a 2-, 6- and 12-channel spiral pumps; FIG. 2G shows a 6-channel pump with a common central port and six independent outer ports, used for either combining or separating multiple flows; FIG. 2H shows an 8-channel binary-splitter pump that has a single input and a single output, but multiple internal channels to provide a high pumping rate; FIG. 2O shows an assembled pump cartridge according to U.S. Pat. No. 11,465,144 B2 and 11,474,531 B2, which are incorporated herein by reference in their entireties.

FIG. 3A is an exploded views of a 24-channel sensor valve cartridge; FIG. 3C shows one of the failure modes in which a tube is inserted into a punched port so deep as to occlude the channel; FIGS. 3D, 3E, and 3F shows the details of a chip having ports with shoulders that limit the insertion of the tube to a point well above the transverse microfluidic channel; FIGS. 3G, 3H, and 3I shows the details of a connector disk; FIG. 3O shows a configuration of the fluidic side of the actuator for a pump.

FIGS. 4A-4G present the subsystems of a system for mounting pumps and valves that can be used to create a CAPCAS and how they can be implemented in hardware, according to embodiments of the invention, where FIGS. 4A and 4B show one embodiment of the chassis that could contain one of the 12- or 48-channel fluidic systems shown in FIG. 1F; FIGS. 4C-4G provide details that demonstrate how the motor and fluidic assemblies can be readily connected or separated, as required for exchange of fluidic cartridges to revise an experimental design, to replace worn fluidics, or for sterilization, in a lift-side view (FIG. 4C), a lift-side, exploded view (FIG. 4D), a front perspective view (FIG. 4E), a rear perspective view (FIG. 4F) and an enlarged partial front perspective view (FIG. 4G), respectively.

FIGS. 7A-7E show how a mechanical or magnetic in-line gear reduction adapter could be inserted between the motor and the fluidic cartridge in FIG. 4A to increase or decrease the speed with which the pump or valve rotates as compared to the motor that drives it, according to embodiments of the invention, where FIG. 7A shows one embodiment of the in-line gear reduction adapter; FIGS. 7B and 7D show a mechanical gear reduction adapter having a ring gear, sun gear, and a system of planetary gears enclosed within a tubular housing; and FIGS. 7C and 7E show a magnetic gear reduction adapter having an outer magnetic rotor, a rotating ferromagnetic pole element, and an inner magnetic rotor, all enclosed within a tubular housing.

DETAILED DESCRIPTION OF THE INVENTION

Figure 1A:
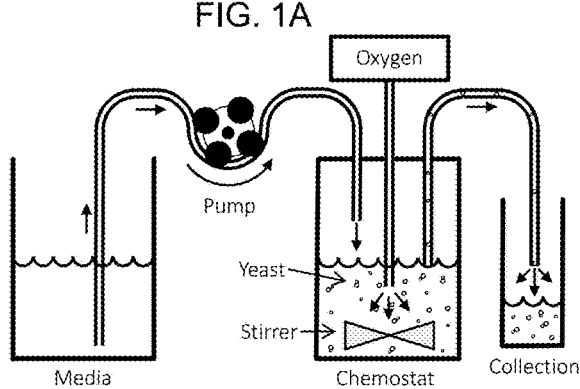
FIGS. 1A-1C present schematic representations of a single-well chemostat (FIG. 1A), a microclinical analyzer (FIG. 1B), and a multi-well microformulator (FIG. 1C), respectively, which provide foundational operations of the invention.
Figure 1B:
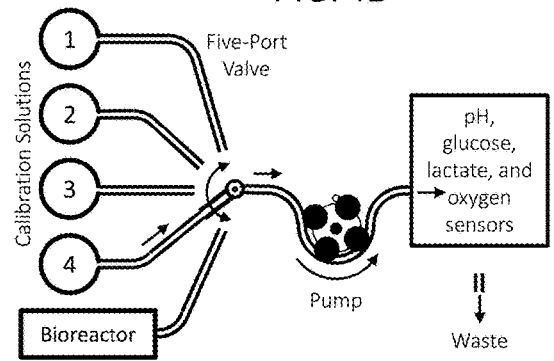
Figure 1C:
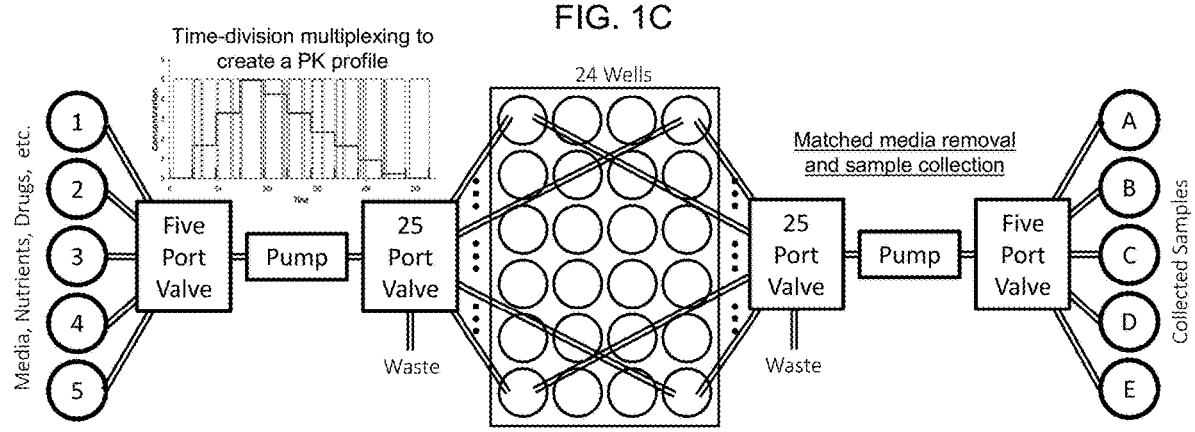

The invention will now be described more fully hereinafter with reference to the accompanying drawings, in which exemplary embodiments of the invention are shown. The invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. As used herein, the term "and/or" includes any and all combinations of one or more of the associated listed items.

As used herein, the term "biodevice" refers to a well plate, a chemostat, an organ chip, a Transwell plate, a bioreactor, an abiotic or biotic chemical synthesis reactor, or other fluidic reservoirs that are contained in a multi-element biodevice array.

As used herein, a chemostat is a particular type of bioreactor, and hence reference to a bioreactor could serve as a reference to a chemostat, or vice versa.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

In view of the aforementioned deficiencies and inadequacies presented in the background, one of the objectives of this invention is to address the need for better hardware for fluid handling of well plates, and arrays of microbioreactors and other biodevices and bio-objects that require continuous perfusion with media, or intermittent removal and replacement of media, or adjustment of the formulation of the media over time, with applications to chemostats and organ chips. In this context, the term "media" would include cell-culture media, nutrient solutions for model organisms such as zebrafish embryos, and even constituent chemical components and reactants in biotic and abiotic chemical synthesis processes. The hardware presented in this invention could enable the simultaneous and fully automated support, interrogation, and analysis of a thousand or more chemostats, bioreactors, well plates, organ chips or other biodevices or chemical reaction chambers, operating as self-driving systems biology laboratories. This system will enable new types of studies to understand, model, and control microbial populations, differentiating stem cells, antibody-producing cells, organoids, and tissue chips.

The invention addresses this need for multi-channel microfluidic pumps and valves to control multiple multi-well chemostats, bioreactors, well plates, or organ chips over a wide range of conditions with E. coli and other prokaryote microbes, different strains of yeast, CHO, and other eukaryotic cells, and other bio-objects. There are innumerable potential applications of this invention, with multiple proven markets that could benefit immediately from high-multiplicity pumps and valves.

The invention builds upon prior inventions described above to enable the fabrication and operation of a new class of automated bioreactor systems. Specifically, the invention in one aspect discloses the microfluidic hardware required to implement a continuous automated perfusion culture analysis system (CAPCAS) comprising one or more fluidic systems configured to operate large numbers of biodevices such as chemostats, wells, bioreactors, abiotic or biotic chemical synthesis reactors, or other biodevice arrays in parallel.

While the inventions herein are discussed primarily in the context of CAPCAS embodiments that include multi-well chemostats and self-driving laboratories that operate as autonomous robot scientists (as discussed in detail in U.S. Pat. No. 11,447,734 B2), the pump and valve architectures of this invention could be applied to a wide variety of fluidic and biomedical applications. Other uses of these technologies that are not discussed in detail in this application include the long-term perfusion and analysis of multiple individual or coupled organs-on-chips, the optimization of commercial and scientific biotechnology processes that include but are not limited to the differentiation of induced pluripotent stem cells (iPSCs) or mesenchymal progenitor cells (MSCs) into a desired progenitor, intermediate phenotype, or terminally differentiated cells for regenerative medicine or biomedical research, and the production of pharmaceutical antibodies and other proteins by Chinese hamster ovary (CHO) cells. Other applications not presented in detail include the imposition of hormonal, chemical, or optical circadian rhythms,[43] and the continuous or circadian feeding of zebrafish embryos in, for example, a 12-well Transwell plate, or the use of a fully automated cell culture system for the study of chemical and biological weapons and their therapeutics and prophylactics.

Figure 1D:
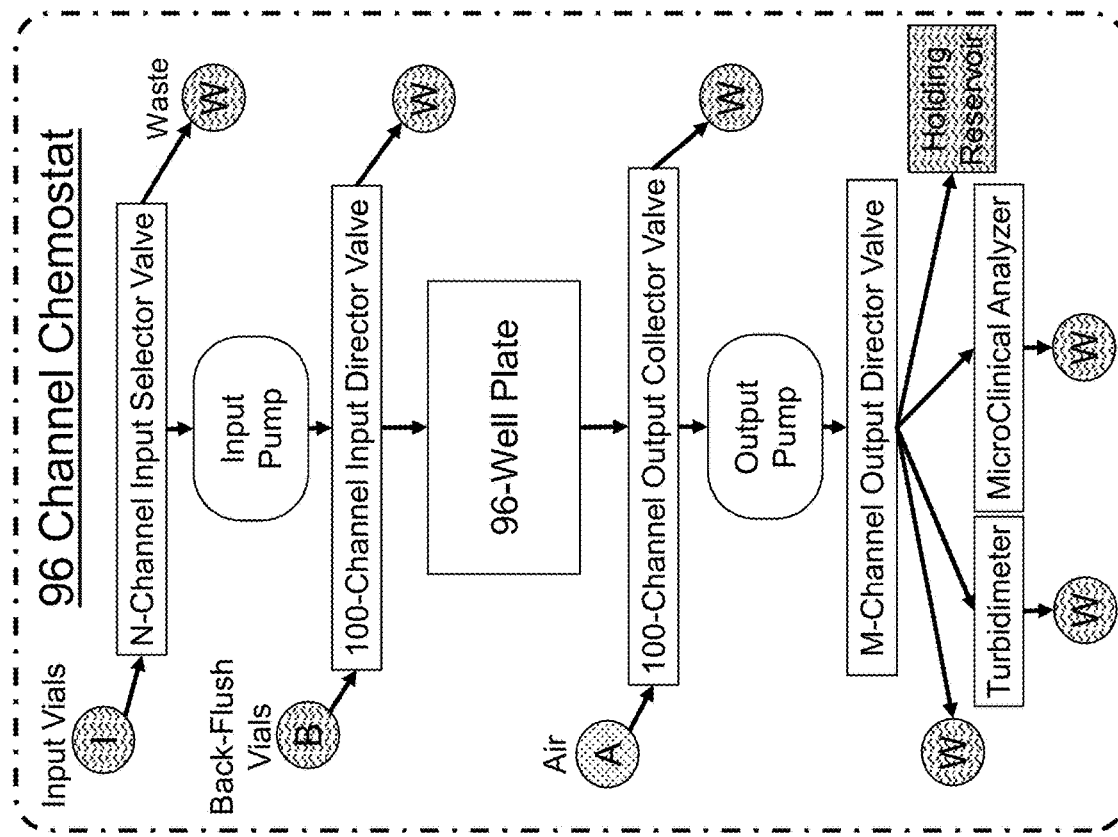
FIG. 1D presents the conceptual design of a 96-channel chemostat/bioreactor.

FIG. 1D shows how a 96-channel chemostat could be implemented using RPPMs and RPVs, wherein each well of the 96-well plate is in fact an independent chemostat that has media delivery, fluid removal, stirring, and gas control. An N-channel selector valve selects media and drugs from input vials and delivers them to a 100-channel input director valve (the 100-channel valve was previously disclosed in PCT Patent Application Serial No. PCT/US2021/042179 by J. P. Wikswo, et al.,[30] which is incorporated herein by reference in its entirety). Reversing the input pump allows fluid such as sterile saline to be used to wash either valve, and sends the wash water to waste reservoirs. The input director valve allows the input pump to deliver the individually formulated media to each well of the 96-well plate. The 100-channel output collector valve, the output pump, and the M-channel output director valve in concert remove media from each well in the 96-well plate and deliver it to waste, a turbidimeter, a microclinical analyzer, or a holding reservoir, for example. Each of the valves has a connection to back-flush vials (B) and pressurized air or other gas (A) to insert one or more bubbles between each sample. The concept shown in FIG. 1D is applicable for any number of chemostats or bioreactors other than 96, for example 12, 24, 48, or 384, with the appropriate minimum number of channels being required for the pumps and valves that comprise the system.

Figure 1E:
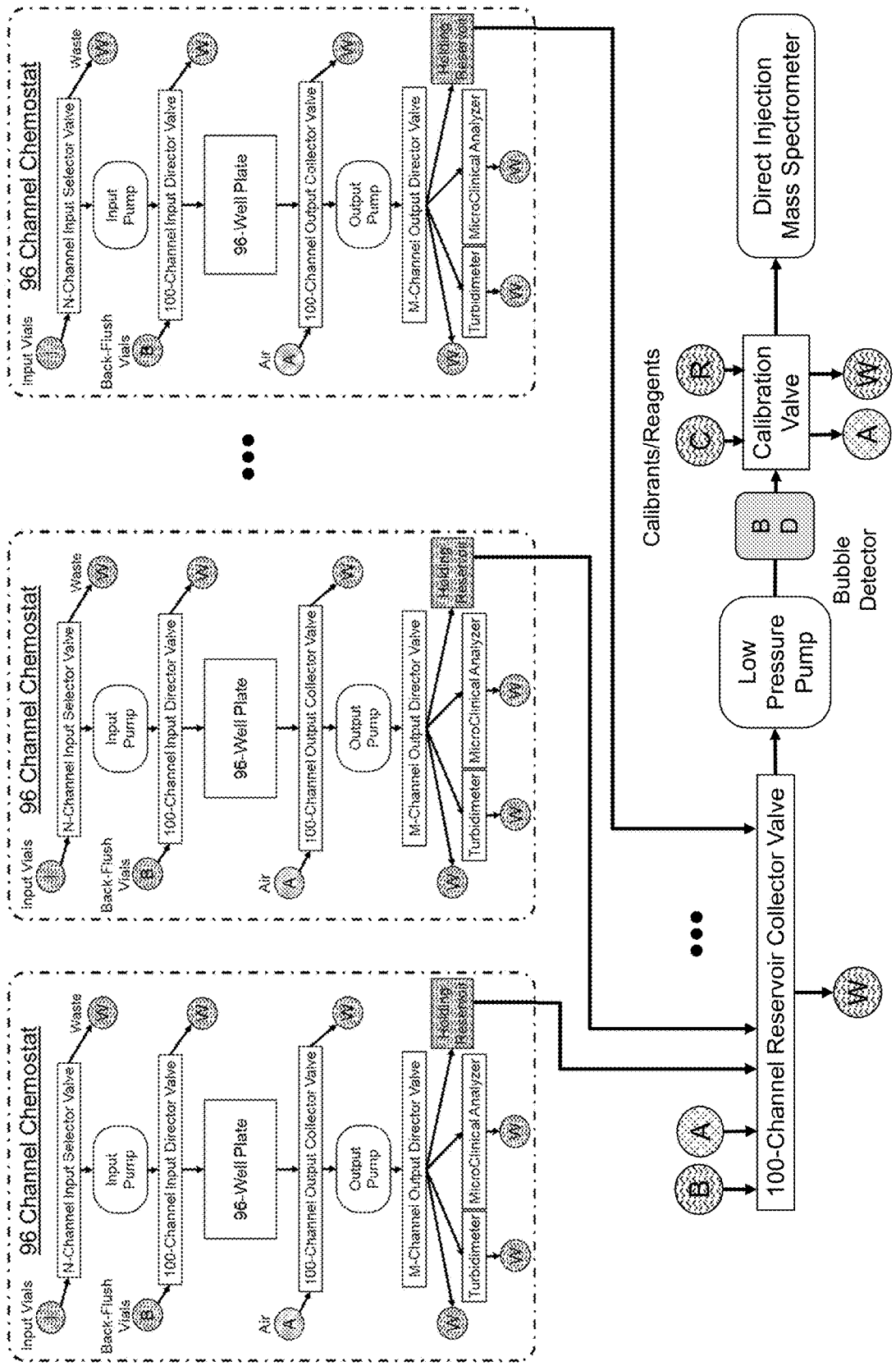
FIG. 1E shows how 100 of these units can be connected to create a 9,600 channel chemostat/bioreactor system, according to embodiments of the invention.

FIG. 1E illustrates how the addition of a second 100-channel valve, termed the reservoir collection valve, can be used to analyze media from any single chemostat in any of 100 96-well plate chemostat arrays, thereby creating a 9,600 chemostat system. By means of this valve, a low-pressure pump withdraws media from the holding reservoir that transiently retains the media and cells withdrawn from the desired chemostat or bioreactor well. A bubble detector identifies where one sample ends and another starts, as the low-pressure pump delivers the samples to the direct injection mass spectrometer. Note that depending upon the type of mass spectrometer, there may be a high-pressure pump for pressure-injection of the sample into either a liquid chromatography system upstream of the mass spectrometer or a sample ionization and injector at the mass spectrometer; these pumps would not use the technologies shown in FIG. 2. The calibration valve can remove air through one port (A), send the leading portions of any sample to waste (W), and inject either a reagent (R) or a calibration solution (C) into the mass spectrometer. This concept could be applied to connect a plurality of chemostat plates with any number of chemostats on each plate.

To demonstrate the feasibility of creating such a system with functional pumps and valves, we next present embodiments of the invention that will provide 12-, 48-, 144- and higher-channel versions of a CAPCAS comprising one or more fluidic systems configured to operate large numbers of chemostats or other biodevices in parallel.

FIGS. 1F-1I outline the assembly of pumps, valves, and sensors required to provide an exquisite level of control for closed-loop control of multiple bioreactors and other bioreactors. Given the volumes of cells and media for multi-omic interrogation of bioreactors and other bio-objects, the multi-channel fluidic pumps and valves must operate at flow rates that typically are between 1 µL and 1 mL per minute, well beyond the flow capability of the classic pneumatic microfluidic valves,[48, 49] which require a dedicated and expensive high-speed solenoid as well as a separate compressed gas line for each solenoid. Other valves, such as microfluidic rocker valves or rotating disk valves, are typically too large and too expensive, or are unable to perform complex valving operations required for robot-scientist interrogation of bio-objects are required to understand the mechanism of action of drugs and toxins. We now describe rotary planar peristaltic micropumps (RPPMs) and rotary planar valves (RPVs) specifically configured to implement the fluidic control circuits shown in FIGS. 1F-1I.

FIGS. 1F and 1G show embodiments of a multi-chemostat fluid control system described in detail in U.S. Pat. No. 11,447,734 B2 that support 12, 48, 144 and more independent chemostats. FIG. 1F shows a fluidic schematic for the 12-chemostat multi-well microchemostat module that has an input reservoir plate whose wells are filled by a microformulator (V1, P1, and V2) to create two banks of input reservoir wells, which are emptied one bank at a time by one of two pumps (P2 and P3) and delivered to the appropriate bioreactor well in the chemostat plate. Two other pumps (P4 and P5) can extract media and possibly suspended cells from each of 12 bioreactor wells and either deliver media from a selected well to an analytical instrument by means of a sensor valve V3 while sending the effluent from the other wells to a common waste, or transfer media from each bioreactor well to another well plate for off-line analysis. The embodiment in FIG. 1G is similar to that in FIG. 1F except that the output of each well of the chemostat plate is delivered by a selected pump (P4 or P5) to be delivered to one of two output plates. In both embodiments, a 48-channel system would have the same topology, except 48 chemostats and pumps, valves, and sensors with proportionally more channels.

The most recent implementation of the pumps and valves that can be utilized will be discussed below, but for now we will first demonstrate an exemplary embodiment of a fluidic system with FIG. 1F, showing how a 12-channel chemostat system can be created using a 25-port RPV (V1), a single-channel RPPM (P1), a 25-port RPV (V2), four 12-channel RPPMs (P2, P3, P4, and P5), a 12- or 24-port sensor or cut-in RPV (V3), an input reservoir well plate, and output plate, as well as multiple 1- and 12-channel optical sensors. As we will see, the 48- and 144-channel versions can have the same topology, except all wells in the chemostat plate would be populated to create 48 chemostats, and pumps, valves, and sensors would have proportionally more channels. The highest channel count systems would be similar in design, but would utilize a 96-well chemostat plate and minimize the use of input and output well plates to conserve space. The details of the chemostats/bioreactors that provide thermal and gas control and stirring are discussed in detail in U.S. Pat. No. 11,447,734 B2.

FIG. 1F shows how pumps, valves, and sensors would be assembled to create a 12-channel chemostat that operated in 12 of the 48 wells of a round-bottom, deep-well plate. The first stage of the multi-well chemostat module is a media microformulator that has a 25-port input selector valve (V1), a single-channel pump (P1), and a 25-port output director valve[28] (V2) that together can create a different time-varying perfusion mixture for each chemostat. The microformulator output is delivered to two sets of 12 wells in the 96-well input reservoir plate, such that one set can be refilled while the second set is being delivered by 12-channel spiral pumps[35] P2 or P3 to twelve populated wells in the 48-well chemostat plate, providing uninterrupted perfusion. Were the cells being cultured exhibiting slow growth, time-division multiplexing could be used by the microformulator (V1, P1, and V2) to deliver a different media formulation to each bioreactor or chemostat. However, the growth rate of some yeast is sufficiently high that the time interval for the microformulator to revisit each well would be too long and between visits there could be significant changes in nutrient and metabolite concentrations. The use of two sets of input reservoir wells in a single well plate (or possibly two well plates) and two associated and dedicated multi-channel pumps, P2 and P3, ensures that one pump can deliver media from one set of reservoir wells simultaneously to each chemostat/bioreactor well, while the other set of reservoir wells is being refilled. This ensures that each chemostat/bioreactor can be perfused without any interruption or human intervention for very long periods of time. In U.S. Pat. No. 11,447,734 B2 we discuss how a faster serial or parallel microformulator might obviate the need for the input reservoir plate, allowing direct delivery of formulated media to the chemostat/biodevice plate.

The effluent (cells plus media) from each chemostat well is collected by a 12-channel pump P4. If the pump speed of P4 is greater than that of P2 or P3, the level of the media in each bioreactor or chemostat will be determined by the height of the withdrawal tube in that well. By overpumping P4, there will be intermittent withdrawal of air and/or foam from each reactor, which can also be used to define a sample bolus for later analysis.

The output of P4 is delivered to the 12-port, multi-mode output/sampling valve V3. This valve will allow each effluent line, one at a time, to be diverted to an external analyzer, such as a VIIBRE/Waters rapid-cycling UPLC-IM-MS[50, 51] or Agilent SPE-IM-MS,[52-54] a Raman[55-60] or UV-Vis spectrometer, optical[61] or electrochemical[18, 19, 21-23, 25-27, 33, 62-66] metabolic sensors, or a planar microfluidic device that would allow visualization of individual yeast cells as they exit a chemostat.[67] When one chemostat is being sampled, valve V3 would direct the media being pumped from the other chemostats to waste, with each chemostat being sampled serially. As appropriate, the analyzer will be equipped with a spiral microfluidic sorter,[68-71] or a filter (alternating tangential flow (ATF) or tangential flow filtration (TFF)[72-75]) for real-time separation of cells from media, as well as an in-line, microfluidic acoustic[76, 77] or electrical[78] lyser. In its third mode, V3 can divert the effluent from all chemostat wells to waste to ensure continuous perfusion when no sample is needed from any well.

It is important to recognize that the separation of cells for media will enable the CAPCAS as presented herein to operate as a continuous perfusion bioreactor for suspension cells, since the cells in the effluent could be separated from the media and returned to the bioreactor to improve the concentration of cells in the bioreactor and hence optimize their production of secreted biomolecules. This is particularly important, for example, when the system is used to culture Chinese Hamster Ovary (CHO) cells, which are a mainstay in the production of biological pharmaceuticals, including antibodies and specific therapeutic proteins.

The pump P5 operates independent of P4 to deliver the effluent from each chemostat well to a separate well in the refrigerating/freezing output plate for off-line transcriptomic or other off-line analysis. The output plate can be removed after bulk sample collection, while P4 continues to withdraw media from each chemostat/bioreactor.

Bidirectional washing of the microformulator, the input reservoirs, and even each well in the chemostat plate is possible. The chemostats can be inoculated by using an external pipettor or robot to seed either the chemostat plate before or after installation beneath the fluidic station. While the output plate would normally be empty at the beginning of an experiment, alternatively it could be used to inoculate an array of sterile chemostats at the beginning of an experiment. A transfer plate that has one or more seeded wells can be installed in place of the output plate with pump P5 run in reverse to deliver the selected cells into various chemostat wells to initiate their culture.

The single-channel optical sensing module after P1 will be used to track an intentionally injected bubble for measurement of flow rate, or to identify when a media or drug reservoir has been emptied. The three 12-channel optical sensing modules will measure, for example, $PO_2$, $PCO_2$, and pH and optical density (OD) of the media entering and leaving each chemostat.

While the spiral microfluidic sorter,[68-71] or alternating tangential flow or tangential flow filtration,[72-75] could separate cells from extracellular media to allow separate analysis of the intracellular and extracellular proteomic and metabolomic profiles, the same technologies could also be used to return the cells to the bioreactor while allowing the conditioned media to exit the system, either for disposal or harvesting of secreted proteins and other cellular products. By including this separation, the chemostats would be converted to continuous perfusion bioreactors, wherein the cells were retained to increase in number and, if desired, continue to produce in quantity the targeted secreted proteins or other molecules. Hence, with the addition of the appropriate spiral, ATF, or TFF separation, the robot-scientist, self-driving CAPCAS platform could then be applied to entirely different classes of industrial problems, including the production of antibodies, enzymes, food protein, or other biomolecules.

A 48-chemostat embodiment would have the same topology as that in FIG. 1F, except that the 12-channel pumps (P2-P5) and the 25-port valves V2 and V3 would be replaced with 50-channel tubing pumps and 100-port valves,[34] respectively. The sensor count would also be increased from 12 to 48. In this case, the fluidic circuit would service all 48 wells in the plate shown, but the topology would be identical. We do not draw the 48- or higher channel-counts circuit to simplify rendering and teaching these embodiments.

The use of the input reservoir plate and the pair of pumps P3 and P4 that ensure continuous perfusion of the chemostats/bioreactors requires, in this design, that the input reservoir plate have twice as many wells as the chemostat/bioreactor plate. Were a 96-well chemostat plate used, two 96-well input reservoir plates could be used, or the microformulator could either be parallelized or its speed increased to eliminate the need for the input reservoir plate or allow the input reservoir plate to be periodically refreshed rather than emptied.

Figure 1H:
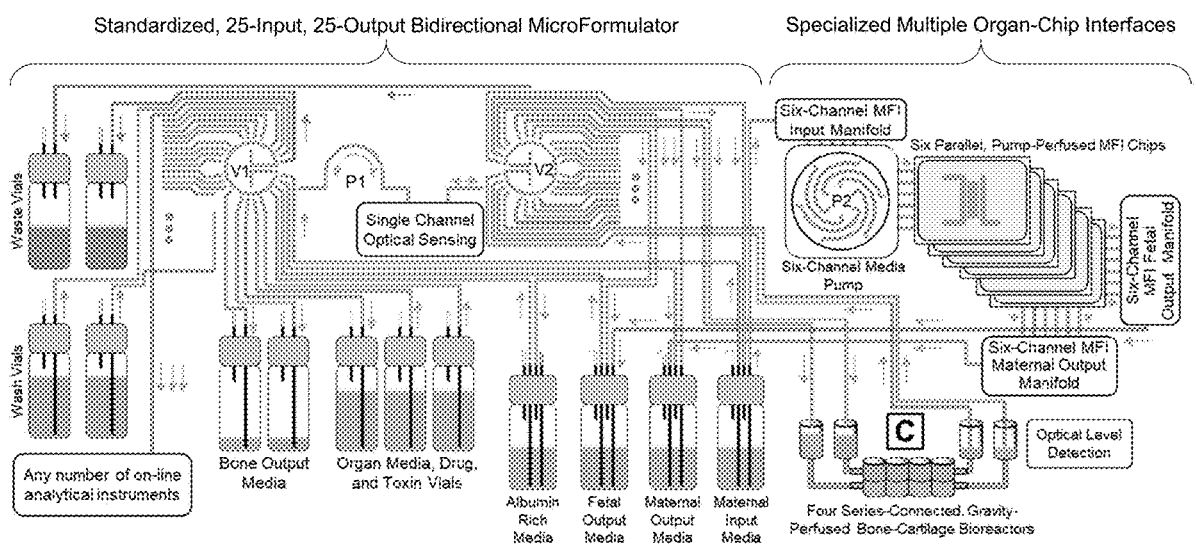
FIG. 1H presents a system layout with a bidirectional microformulator that could support six maternal-fetal interface chips.

FIG. 1H shows a fluidic circuit based upon that in FIG. 1F that is configured to perfuse six parallel, pump-perfused maternal-fetal interface chips and collect their effluent and deliver it to four series-connected, gravity-perfused bone-cartilage bioreactors, all compatible with the CAPCAS architecture. A major advance in this design is to use the microformulator in a bidirectional manner, such that intermediate reservoirs can be used to create mixtures of fluids from a variety of reservoirs, including ones that are downstream of the microformulator. This requires that pump P1 operate in both directions, and that the lengths of the reservoir tubes are appropriate as required for fluid delivery and removal.

Figure 1I:
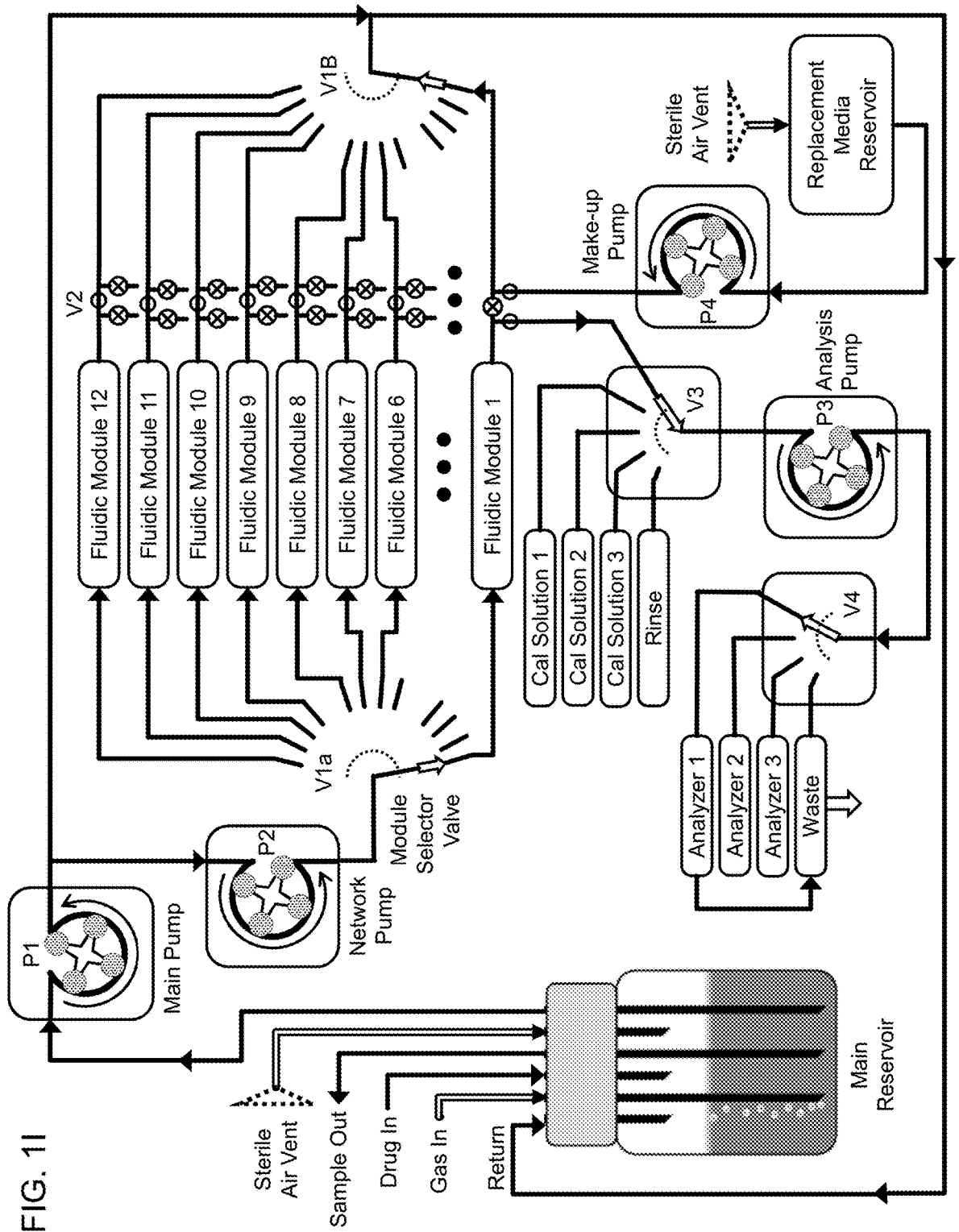
FIG. 1I shows how pumps and valves can be used to interconnect and recirculate media between 12 different fluidic modules, organ chips, bioreactors, or other bio-objects.
Figure 1K:
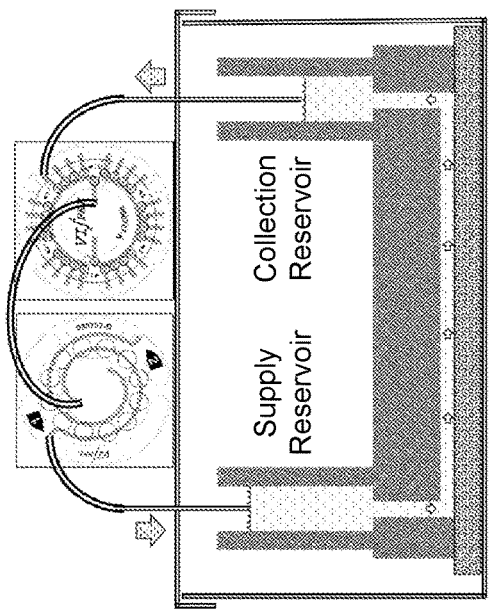
FIGS. 1J-1M respectively show how a system of pumps and valves above a box or well plate (represented in the figure as a simple pump-valve pair) can be used to perfuse through needles inserted into intermediate reservoirs an organ chip (FIG. 1J), maintain the fluid reservoirs in a single-chamber gravity-perfused organ chip or bioreactor (FIG. 1K), a two-chamber barrier bioreactor (FIG. 1L), and both sides of a Transwell (FIG. 1M).

FIG. 1I shows a pump and valve systems that can sequentially perfuse with recirculation of a common media each of 12 fluidic modules (i.e., organ-on-chip, bioreactor, or other bio-object) by means of a pump (P2) and a double valve (V1a and V1b). A cut-in valve (V2) extracts media from each fluidic module for analysis controlled by two valves (V3 and V4) and a pump (P3) while replacing the volume of fluid extracted for analysis with fresh media by means of a make-up pump (P4). Continuous recirculation of the common media between the fluidic modules and the main reservoir is ensured by pump P1.

Figure 1M:
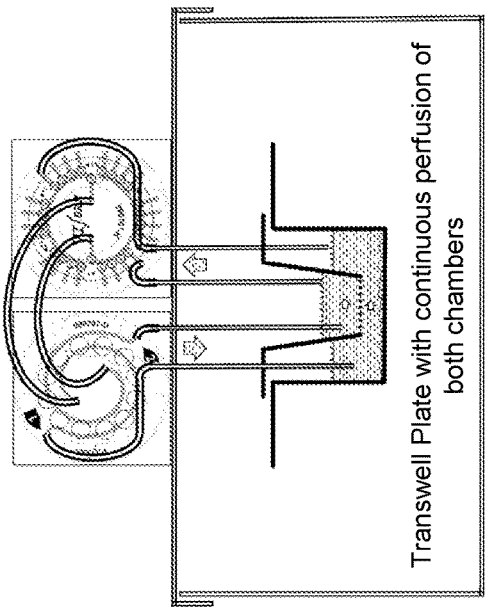

FIGS. 1J-1M show how a system of pumps and valves above a box or well plate (represented in the figure as a simple pump-valve pair) can be used to perfuse through needles inserted into intermediate reservoirs on an organ chip (FIG. 1J), maintain the fluid reservoirs in a single-chamber gravity-perfused organ chip or bioreactor (FIG. 1K) or a two-chamber barrier bioreactor (FIG. 1L), or both sides of a Transwell (FIG. 1M). In each case, the use of multi-channel pumps and valves would allow this fluidic topology to be implemented in multiple organ chips, bioreactors, Transwells, or chemostats at the same time. Because the pumps utilized in shown in FIGS. 1F-1I are pressure-tight against back pressure, as are the valves when in the closed state, when higher perfusion pressures are required without using taller reservoirs and longer needles it would be instead possible to add pressure-tight seals to both the reservoir lid and the lid to the organ-chip plate to allow the fluidic control system to service pressurized-reservoir organ chips such as those manufactured and used by Cell ASIC, Nortis, and Emulate. Similarly, it would be possible to insert pressurized input reservoirs in the fluidic circuit in FIGS. 1F-1G, since the pumps and valves that service that portion of the circuit would act as check valves to maintain the pressure in the reservoir, with the pressure being developed by the pump P1. If desired, this would allow pumps P2 and P3 to be replaced with a valve that would switch the downstream organs from one set of pressurized reservoirs to another. In this context, a key feature of the subject pumps and valves is that the pumps can produce appropriate pressures at flow rates consistent with pressurizing a reservoir, and the valves are normally closed so that they can withstand that pressure.

FIG. 2 shows a previously reported embodiment of a cartridge design that can be used to implement the pumps and valves utilized in FIG. 1. FIG. 2A provides details for the sensor valve (V3) in FIG. 1F. The fluidic circuit is fabricated from polydimethylsiloxane (PDMS). A collection of balls trapped in ball cages is either pressed up into the fluidic chip to close a channel, or allowed to drop to open the channel. The fluidic chip is pressed into the fluidic plate and held in place laterally by protrusions that also serve as tubing ports.

FIG. 2B shows a rotating planar peristaltic micropump whose actuator contains a groove around which balls roll, with an elastomeric traction ring ensuring that the balls roll rather than slide. A free-floating sprocket spacer maintains a uniform separation of the balls.

FIG. 2C shows a single-channel spiral pump, with the shape of the spiral optimized to minimize peristaltic oscillations and backflow.

FIGS. 2D, 2E, and 2F show 2-, 6-, and 12-channel spiral pumps.

FIG. 2G shows a 6-channel pump with a common central port and six independent outer ports, as would be used for either combining or separating multiple flows.

FIG. 2H shows an 8-channel binary-splitter pump that has a single input and a single output, but multiple internal channels to provide a high pumping rate. The width of the channels need not be uniform but can be scaled in proportion to the flow through each section. Such a pump could be fabricated with any number of channels that is a power of two.

Figure 2M:
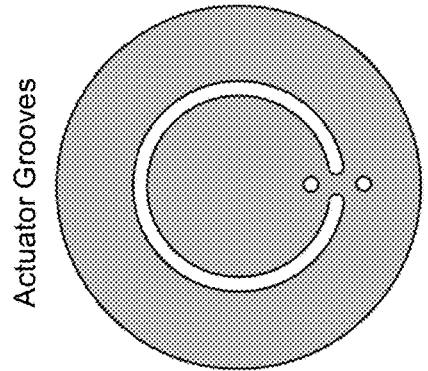
FIGS. 2L, 2M, and 2N provide construction details for the cut-in valve.
Figure 2N:
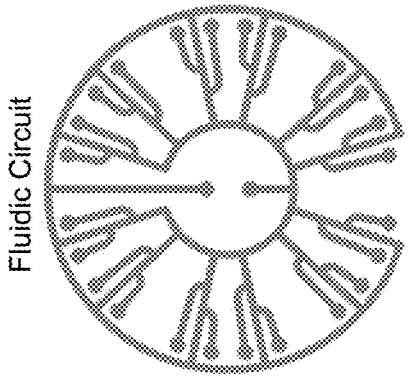
Figure 2L:
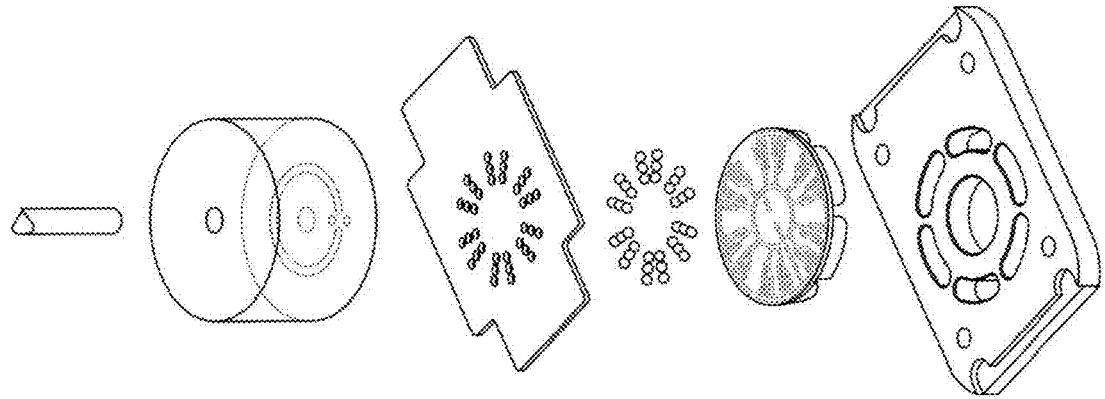
Figure 2J:
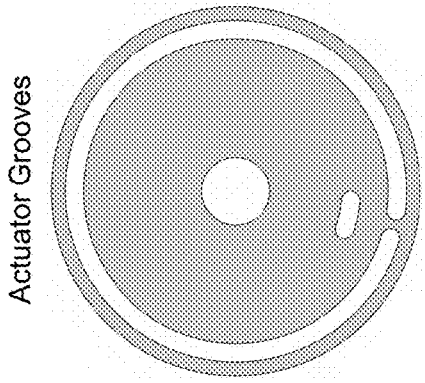
FIGS. 2I, 2J, and 2K provide construction details of the sensor valve.
Figure 2K:
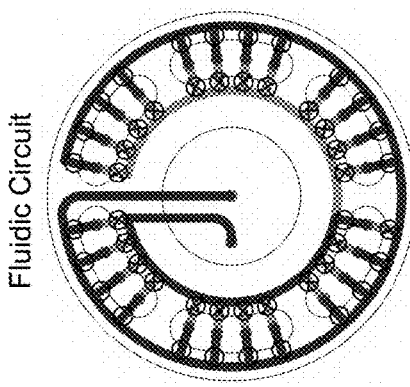
Figure 2I:
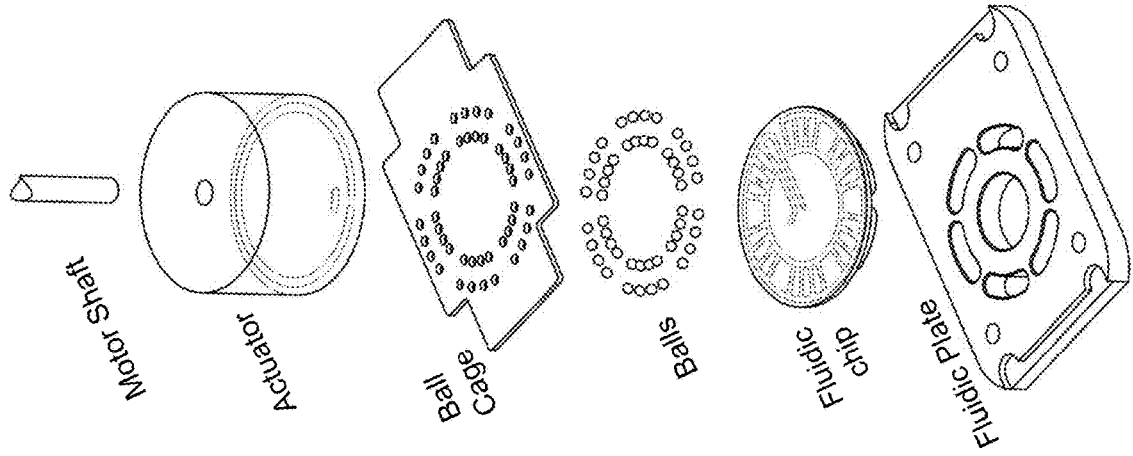

FIGS. 2I, 2J, and 2K provide construction details of the sensor valve, which is designed to allow any one of 24 lines to be directed to a sensor while the remaining 23 channels are directed to a common waste.

FIGS. 2L, 2M, and 2N provide construction details for the cut-in valve, which allows 11 of 12 channels to flow independently, and the chosen $12^{th}$ channel to be diverted to another fluidic circuit, which would allow destructive analysis of the cells and media in that channel and the injection of make-up media downstream of the valve. Either valve could be used for V3 in FIG. 1F; most of our discussion has assumed that V3 will be a sensor valve. The use of a cut-in valve might allow the elimination of P5 and the connection of P4 and V3 to the output plate.

Figure 2O:
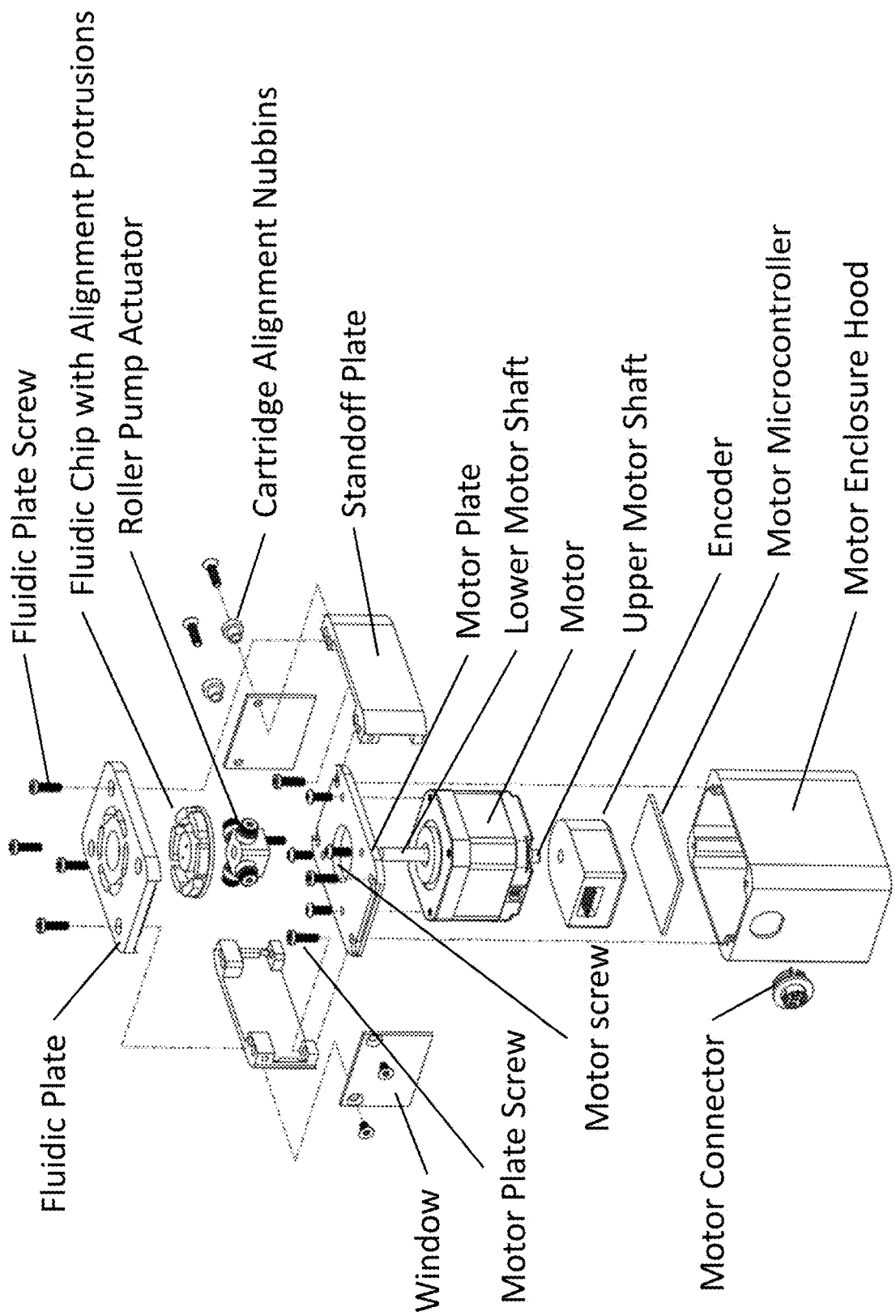

FIG. 2O shows an assembled pump cartridge according to U.S. Pat. No. 11,465,144 B2 and 11,474,531 B2, which are incorporated herein by reference in their entireties.

FIGS. 1F-1I outline embodiments of the sensing and fluidic control system to operate large numbers of chemostats, bioreactors, or other bio-objects in parallel. The coordinated operation of the numerous pumps and valves requires an exquisite level of control of multi-channel fluidic pumping and valving functions that can operate at flow rates that typically are between 1 μL and 1 mL per minute, well beyond the flow capability of the classic pneumatic microfluidic valves,[48, 49] which require a dedicated and expensive high-speed solenoid as well as a separate compressed gas line for each solenoid. Other valves, such as microfluidic rocker valves or rotating disk valves, are typically too large and too expensive, or are unable to perform complex valving operations required for the functions shown, most notably with the multi-port valves and multi-channel pumps in FIGS. 1F-1I. We now describe rotary planar peristaltic micropumps (RPPMs) and rotary planar valves (RPVs) specifically configured to perform the requisite operations.

FIG. 2A provides details for V3 in FIG. 1F, termed a sensor valve. The fluidic circuit is fabricated from PDMS. A collection of balls trapped in ball cages is either pressed up into the fluidic chip to close a channel, or allowed to drop to open the channel. The fluidic chip is pressed into the fluidic plate and held in place laterally by protrusions that also serve as tubing ports.

FIG. 2B shows a rotating planar peristaltic micropump whose actuator contains a groove around which balls roll, with an elastomeric traction ring ensuring that the balls roll rather than slide. A free-floating sprocket spacer maintains a uniform separation of the balls.

FIG. 2C shows a single-channel spiral pump, with the shape of the spiral optimized to minimize peristaltic oscillations and backflow.

FIGS. 2D, 2E, and 2F show 2-, 6-, and 12-channel spiral pumps.

FIG. 2G shows a 6-channel pump with a common central port and six independent outer ports, as would be used for either combining or separating multiple flows.

FIG. 2H shows an 8-channel binary-splitter pump that has a single input and a single output, but multiple internal channels to provide a high pumping rate. The width and/or depth of the channels need not be uniform but can be scaled in proportion to the flow through each section. Such a pump could be fabricated with any number of channels that is a power of two.

FIGS. 2M, 2N, and 2O provide construction details of the sensor valve, which is designed to allow any one of 24 lines to be directed to a sensor while the remaining 23 channels are directed to a common waste. FIGS. 12P, 12Q, and 12R provide construction details for the cut-in valve, which allows 11 of 12 channels to flow independently, and the chosen $12^{th}$ channel to be diverted to another fluidic circuit, which would allow destructive analysis of the cells and media in that channel and the injection of make-up media downstream of the valve. Either valve could be used for V3 in FIG. 1F; most of our discussion has assumed that V3 will be a sensor valve. The use of a cut-in valve might allow the elimination of P5 and the connection of P4 and V3 to the output plate.

We have previously described motor cartridges (FIG. 2O) that were cuboidal, totally enclosed, and wipe-sterilizable in U.S. Pat. No. 11,135,582 B2 and 11,465,144 B2 by D. K. Schaffer, et al.,[28, 29] which are incorporated herein by reference in their entireties. While this cartridge design and the use of a circular chip with alignment protrusion were a significant advance over earlier versions, in which the flat-faced microfluidic chip was pressed against a smooth fluidic plate, the design in FIG. 2O presented a number of serious limitations. The motor and its microcontroller were enclosed in a compartment that could only be accessed by complete disassembly of the system. The parallelism of the plane of the pump and valve actuator and the actuating surface of the fluidic chip was determined by the accuracy of the machining of the standoff plates that separate the fluidic plate from the motor plate or motor support structure, such that measurable departures from planarity adversely affected the operation of the pump or valve. The translational alignment of these plates was determined by the manufacturing tolerances in the location and drilling of the clearance and thread holes for both the fluidic plate screws and the motor plate screws, and the translational alignment environment would be hard to adjust and could change when the fluidic plate screws were tightened. Adjusting compression of a pump or valve actuator required removal of one or both of the windows, the loosening of the set screw (not shown) that locks the actuator to the lower motor shaft, the use of a tool to lift or lower the actuator, the retightening of the set screw, and the replacement of the covers. The system used the internal bearings of the stepping motor to serve as thrust bearings that provided the compression force needed for pump and valve actuation, a function that commercially available stepper motors may or may not be designed to support. The fluidic assembly could not be separated from the motor and its microcontroller, so that it was impossible to use either an autoclave or radiation to sterilize the fluidic components after cartridge assembly. While the interior of the fluidic channels could be sterilized with alcohol and the outside of the cartridge wiped down with alcohol, it was not possible to sterilize the cartridge adequately for operation in a sterile environment, particularly because the interfaces between the standoff plates, the fluidic plate, the motor plate or motor support structure, and the windows provided numerous opportunities for the sequestration and/or migration of microbial contaminants. The motor could not be thermally isolated from the fluidics, leading to fluid heating depending upon motor usage and load.

In view of the foregoing, the invention in one aspect discloses a fluidic cartridge where the fluidics are thermally isolated from the motor. All of the fluidics are installed in a self-aligning housing in a single disposable assembly from which the motor and the fluidics can be readily separated for sterilization and maintenance, which also makes the fluidics disposable and replaceable.

Specifically, the fluidic cartridge comprises a fluidic disk having a plurality of alignment openings; a fluidic chip comprising a body having a first surface and an opposite, second surface, one or more channels formed in the body in fluidic communications with input ports and output ports for transferring one or more fluids between the input ports and the output ports, and a plurality of protrusions formed on the first surface, wherein the plurality of protrusions are received in the plurality of alignment openings of the fluidic disk for aligning the fluidic chip to the fluidic disk; an actuator operably engaging with the one or more channels at the second surface of the body for selectively and individually transferring the one or more fluids through the one or more channels from at least one of the input ports to at least one of the output ports at desired flow rates; and a tube member defining a cylindrical housing for accommodating the fluidic disk, the fluidic chip and the actuator therein.

In one embodiment, the fluidic cartridge further comprises means for mounting a motor for operably driving the actuator to be activated or deactivated; and means for detachably connecting the motor to the actuator.

In one embodiment, the mounting means comprises a motor plate or motor support structure on which the motor is mounted.

In one embodiment, the fluidic cartridge further comprises an array plate or fluidic module support structure attached to the motor plate or motor support structure for locating the motor.

In one embodiment, the fluidic cartridge is thermally isolated from the motor.

In one embodiment, the tube member comprises a double-threaded tube having a first portion and a second portion extending from the first portion; a threaded lock ring threading onto an exterior surface of the first portion of the double-threaded tube; a fluidic compression threaded tube threading onto the exterior surface of the first portion of the double-threaded tube and abutting against the threaded lock ring.

In one embodiment, the fluidic cartridge further comprises at least a first threaded retaining ring and a second threaded retaining ring threaded into the fluidic compression threaded tube, such that the fluidic disk is placed between the first threaded retaining ring and the second threaded retaining ring that in turn, is placed between the fluidic disk and the fluidic chip.

In one embodiment, by the use of the double-threaded tube, the compression of a pump or valve is adjustable simply by rotating the fluidic compression threaded tube and locking it in place with the threaded lock ring.

In one embodiment, the fluidic cartridge further comprises a thrust bearing placed between the motor and the actuator in the housing for supporting a compressive force that is applied by the actuator to the fluidic chip and whose grooves in both thrust bearing races ensure the axial alignment of the actuator.

In one embodiment, the thrust bearing comprises a grooved lower thrust bearing race formed on an upper surface of the actuator body of the actuator; a grooved upper thrust bearing race; a thrust bearing ball cage placed between the lower thrust bearing race and the upper thrust bearing race; a plurality of thrust bearing balls accommodated in the thrust bearing ball cage; and a threaded retaining ring threaded onto an interior surface of the second portion of the double-threaded tube and positioned against the upper thrust bearing race for retaining the thrust bearing that is placed in the housing.

In one embodiment, the connecting means comprises a coupling mechanism for operably coupling the fluidic module to the motor, or decoupling the fluidic module from the motor.

In one embodiment, the coupling mechanism comprises an input coupling, a torque disk, and a driven construct.

In one embodiment, the driven construct corresponds to the actuator used directly in the operation of the fluidic cartridge.

In one embodiment, the driven construct is a second coupling that operably mates with yet another coupling, thereby allowing further constructs to be connected to the drivetrain in a daisy chain fashion.

In one embodiment, the coupling mechanism is an Oldham coupling mechanism comprising an Oldham coupling torque disk coupled to the actuator body of the actuator; and an Oldham coupling drive disk coupled between the Oldham coupling torque disk and the motor.

In one embodiment, the torque disk comprises an upper slot that mates with the coupling boss, and a lower t-slot that mates with a t-boss in the driven construct.

In one embodiment, the motor side of the actuator body is provided with an Oldham coupling key having a capture key so that it holds in place the Oldham coupling torque disk when the motor plate is separated from the array plate or fluidic module support structure.

In one embodiment, the coupling mechanism further comprises pairs of magnets that maintain the approximate axial alignment of the coupling of the torque disk to the actuator.

In one embodiment, the actuator comprises an actuator bearing assembly placed on the second surface of the fluidic chip; and an actuator body operably engaging with the actuator bearing assembly.

In one embodiment, the fluidic cartridge is a valve cartridge, where the actuator bearing assembly comprises a plurality of actuation balls; and an actuation ball cage accommodating the plurality of actuation balls.

In one embodiment, the fluidic cartridge is a pump cartridge, where the actuator bearing assembly comprises a plurality of actuation balls; a sprocket accommodating the plurality of actuation balls; a pocket accommodating the plurality of actuation balls; and a traction ring placed on the plurality of actuation balls.

In one embodiment, the plurality of protrusions is in fluidic communication with the one or more channels through interface ports formed in the plurality of protrusions for allowing connection of external tubing to the fluidic module, wherein the interface ports correspond to the input ports and the output ports. In one embodiment, each of the interface ports has a shoulder formed with a smaller diameter via within each interface port to prevent tubing from bottoming out against channel floors.

In one embodiment, the fluidic cartridge is fluidically connectable to another cartridge or fluidic device through a fluidic interface connector coupled to the interface ports on the plurality of protrusions.

In one embodiment, the fluidic interface connector is a flexible ribbon connector.

In one embodiment, the fluidic cartridge further comprises an in-line gear reduction adapter operably coupled between the fluidic cartridge and the motor.

In one embodiment, the in-line gear reduction adapter is a mechanical gear reduction adapter comprising a ring gear, sun gear, and a system of planetary gears enclosed within a tubular housing.

In one embodiment, the in-line gear reduction adapter is a magnetic gear reduction adapter comprising an outer magnetic rotor, a rotating ferromagnetic pole element, and an inner magnetic rotor, enclosed within a tubular housing.

In one embodiment, the fluidic chip comprises a one-eight-one pump chip comprising eight spiral channels that are directly, mechanically acted upon by the pump assembly's actuating elements.

In one embodiment, the downstream terminus of each spiral channel is a bifurcation, in which that channel converges with another, similar channel, resulting a 2X channel.

In one embodiment, the 2X channel carrying fluid from two spiral channels during pump operation has a cross-sectional area that equals the sum of the cross-sectional areas of each of its contributing channels, and thereby carrying twice the fluid volume.

In one embodiment, the 2X channel, in turn, converges with another, similar 2X channel to form a 4X channel, whose volumetric flow rate is four times that of a 1X channel, wherein after one more bifurcation, an 8X channel delivers all the fluid being pumped through the chip to a plumbing port, which is used to connect the pump chip to an external conduit including flexible tubing.

In one embodiment, the fluidic network upstream of the spiral channels is configured the same way as the downstream network, wherein an 8X channel begins at a plumbing port, splits into two 4X channels, and so on until the path reaches the spiral channels.

In one embodiment, the fluidic chip utilizes eight parallel pumping channels, each end of which is connected to a binary splitter network.

In one embodiment, the fluidic cartridge utilizes alignment pins and sockets to separate and reconnect the motor on the motor plate or motor support structure from the fluidic module on the array plate or fluidic module support structure.

In one embodiment, the fluidic module, once compressed, is inserted into the array plate or fluidic module support structure and held in place with one or more tube retaining screws or other fastening means.

In one embodiment, the fluidic module is in a cylindrical form having an axial symmetry.

In one embodiment, the fluidic module is detachable or separable from the motor.

In one embodiment, the fluidic module is portable, sterilizable, replaceable, and/or disposable.

In another aspect, the invention relates to a fluidic system comprising a plurality of fluidic cartridges disposed on a platform, where the plurality of cartridges comprises pump cartridges, valve cartridges, or a combination of them.

In another aspect, the invention relates to a continuous perfusion bioreactor, comprising an array of sensing and separation heads containing cell separators and media sensors, wherein each sensing and separation head is in fluidic communication with a well and a well tubing group operably connected to pumps and/or valves. In one embodiment, said pumps and/or valves comprise pump cartridges and/or valve cartridges.

In one embodiment, each sensing and separation head comprises a normal flow filter (NFF), and/or a tangential filter comprising a tangential flow filter (TFF) or an alternating tangential flow filter (ATF).

In one embodiment, the tangential filter is adapted for real-time separation of cells from media while minimizing filter fouling by cells, cell debris, and large molecules, wherein the fouling of the filter membrane is prevented by periodic reversal of one or more pumps.

In one embodiment, each sensing and separation head comprises a cell separator for removing suspended cells from an effluent and returning these cells back to the continuous perfusion bioreactor while removing cell-depleted media to maintain a constant volume in the continuous perfusion bioreactor.

In one embodiment, said cell separator is operably connected between one input pump and two output pumps that control the cell separation and recycling process.

In one embodiment, said cell separator is a microfluidic spiral cell separator.

In one embodiment, each sensing and separation head is in fluidic communication with said well through media/cell delivery tubes, media/cell withdrawal tubes, and emptying tubes for removal of large volumes of cells and media therefrom.

In one embodiment, the well tubing group comprises calibration and input tubes for operably delivering calibration input and media input to said sensing and separation head, a recirculation tube for operably circulating media in said sensing and separation head, and waste and media output tubes for operably removing waste output and media output from said sensing and separation head.

In one embodiment, the array of sensing and separation heads is provided with a plurality of bubble tracking flow meters integrated into the continuous perfusion bioreactor.

In one embodiment, each bubble tracking flow meter comprises two spatially separated pairs of a light-emitting diode (LED) and a photodiode (PD) operably connected between a pump and a valve operating in a coordinated manner for detecting the passage of the bubble and thereby the flow velocity In one embodiment, at least one of the plurality of bubble tracking flow meters is located in one desired position in a fluidic system to measure the flow rate, and hence volume, withdrawn from a single fluidic module.

In one embodiment, the array of sensing and separation heads is provided with a plurality of optical density (OD) measuring devices integrated into the continuous perfusion bioreactor.

Without intent to limit the scope of the invention, the exemplary embodiments of the fluidic cartridges and the fluidic system according to the invention are further described below with reference to accompanying drawings. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Figure 3A:
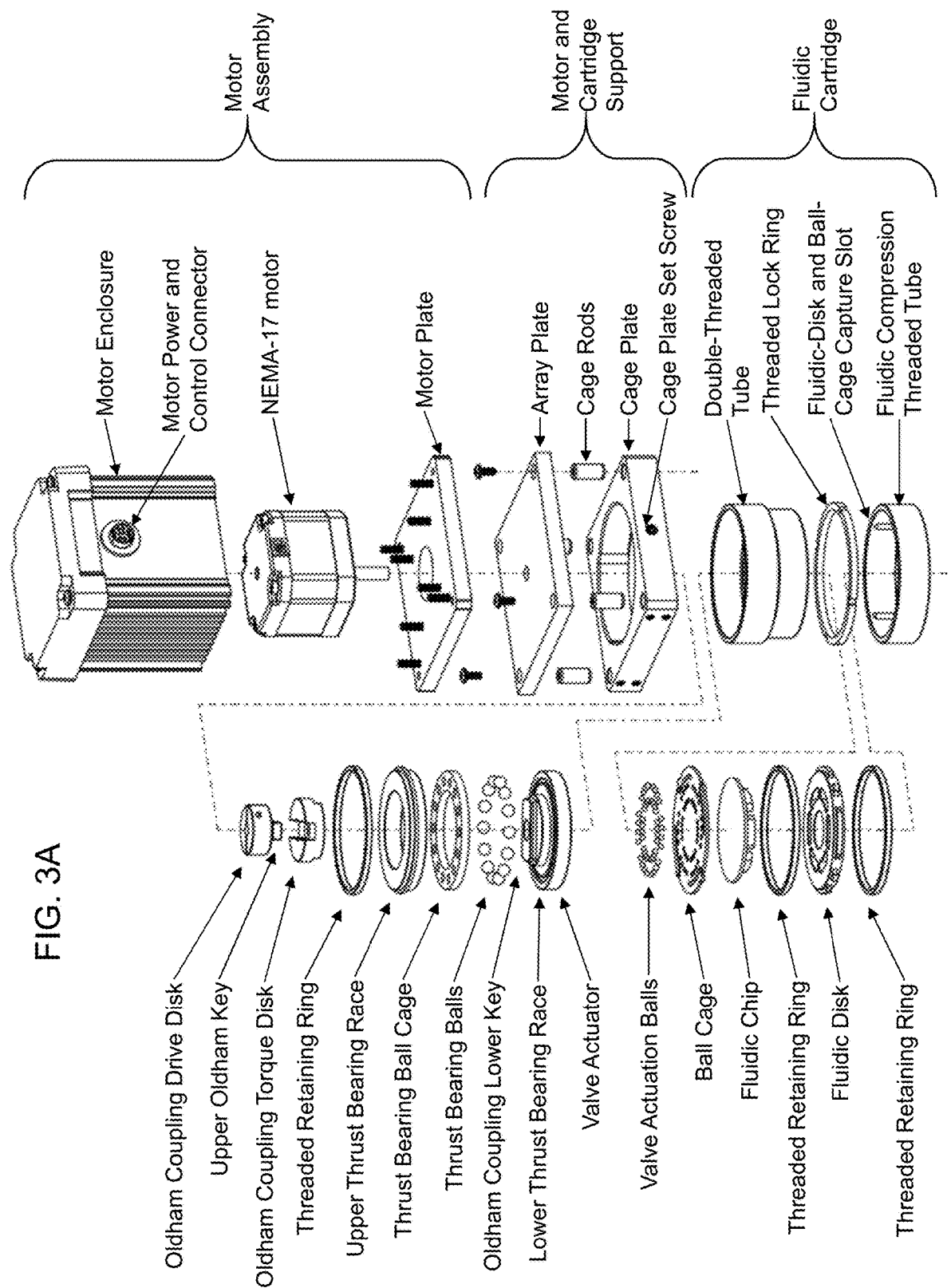
FIGS. 3A-3O show exploded, perspective, and sectional views of cylindrical motor cartridges that contain the pumps and valves required for CAPCAS units, according to embodiments of the invention, where
Figure 3B:
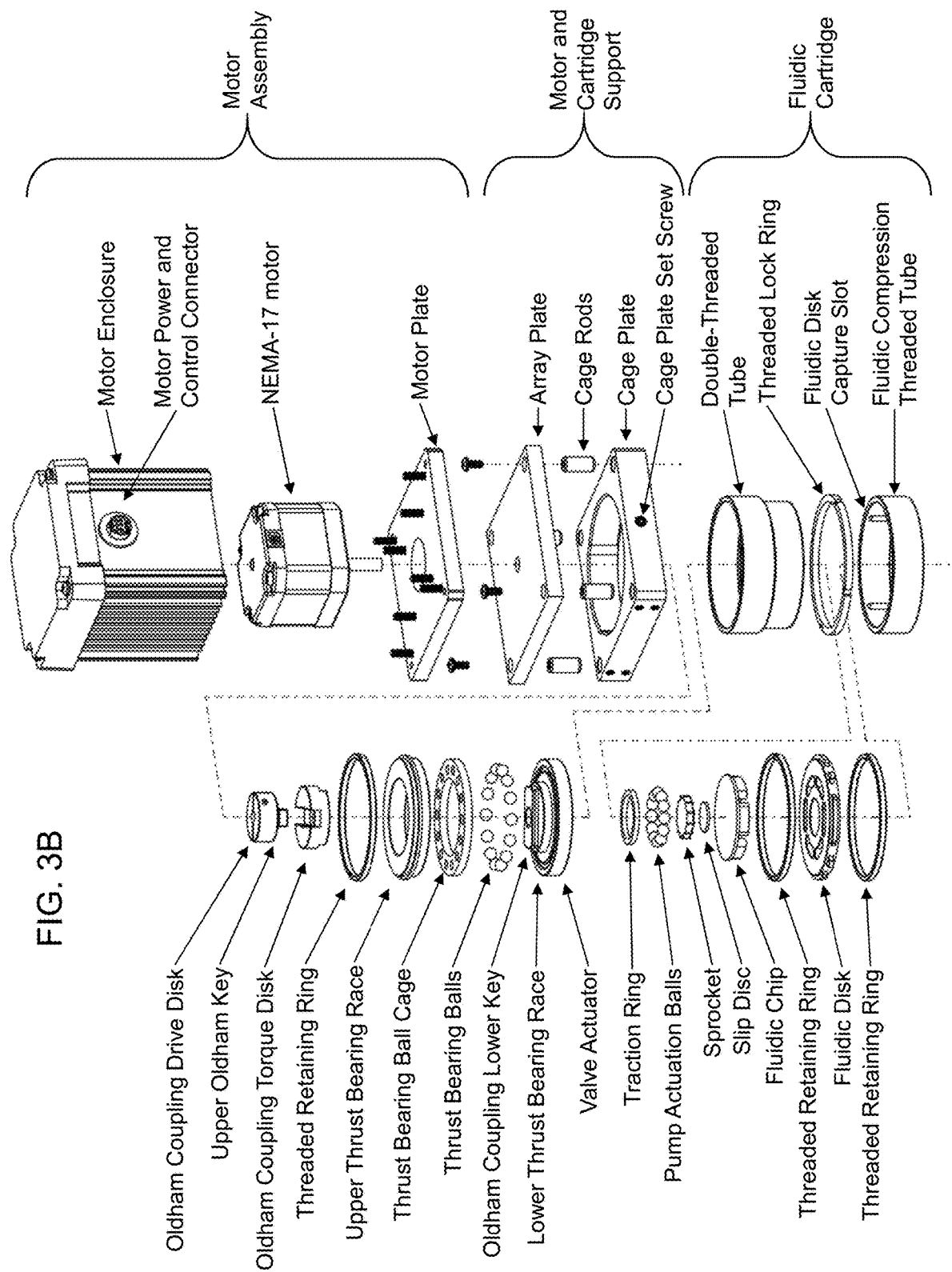
FIG. 3B is an exploded views of a 12-channel spiral pump.

As shown in FIGS. 3A and 3B, the cuboidal geometry of the pump and valve cartridge in FIG. 2O has been replaced with a cylindrical one configured around commercially available threaded tubes and other hardware typically used for mounting optical components.

The use of commercially available lens tubes minimizes the initial requirements for machining while providing an extensible platform that could be easily integrated with custom parts as further embodiments are developed. Ultimately, the fluidic cartridges could be optimized by utilizing custom-designed components.

We recognize the need for precise translational alignment between the fluidic channels and the chip-locating protrusions and the parallelism of all planar surfaces in FIG. 3E.

The cylindrical configuration and axial symmetry in FIG. 3A-3B improve the alignment of the various components, including fluidic channels, the fluidic chip protrusions, the actuator, and the motor. The design simplifies fabrication and assembly, and streamlines the process of compressing the fluidic, thereby producing a more compact cylindrical pump and valve cartridge that can be produced in quantity more economically, is more robust and reproducible, and is more readily serviced. This has eliminated the need to axially align the motor/actuator to the fluidic chip, which was a highly subjective and sensitive operation in the cartridges shown in FIG. 2O.

The fluidic cartridge contains a thrust bearing to support the compressive force that must be applied by the actuator to the fluidic chip, rather than assuming that this force can be provided by the motor. This separate thrust bearing also ensures that the motors and their microcontrollers can be thermally isolated from the fluidic chip.

The pumps have a central support feature, in the form of a slip disc that is backing the pump fluidic chip to prevent the chip from deflecting when ports are intubated.

The tubing ports are cast in place rather than punched, as is the common procedure. Punching produced conical and often ragged ports that may not adequately retain a tube against internal pressure, and punching can also tear the PDMS. Cast ports are cylindrical and smooth over their entire length, and their diameter can be controlled precisely to balance ease of tubing assembly against the probability of the tube being pulled or pushed out of the socket by external or internal forces.

All tubing ports within the fluidic chip have shoulders so that there is both a socket and a smaller diameter via within each port to prevent tubing from bottoming out against channel floors and thereby compromising the function of the fluidic device or ones that are upstream or downstream.

Because the motor can be quickly separated from the fluidics, the fluidic components can be thermally or radiation sterilized without damaging either the motor or its microcontroller.

For the embodiments shown, these cylindrical pump and valve cartridges can be readily fabricated by starting with commercially available, anodized aluminum, threaded lens tubes and retaining rings in widespread use for optical systems, but alternative fabrication means could be used.

The heat-generating motor and the motor microcontroller (not shown) inside the motor enclosure can be thermally isolated from the fluidics, since the only mechanical connection between the two can be through a plastic Oldham coupling that can have minimal thermal conductivity.

The system is fully consistent with the use of ribbon fluidics and multi-port connectors.

The easily decoupled cylindrical fluidic cartridge allows it to become a replaceable/disposable component without requiring the user to be involved in compression adjustments and to decouple the mechanical compression from the motor bearings.

We now discuss these features in detail.

FIGS. 3A and 3B are exploded views of a 24-channel sensor valve cartridge and a 12-channel spiral pump with all components labeled. The Oldham coupling not only accommodates any misalignment of the motor axis with that of the fluidic and its actuator, but it also provides a simple means to separate and reconnect a motor from the cylindrical fluidic cartridge. The motor microcontroller (not shown) can be located inside the motor enclosure.

Classically, the ports in PDMS microfluidic chips are punched after the chip is produced by replica casting. One of the failure modes of this type of chip is that the Tygon tube that is inserted into this punched port can be pressed so deep as to occlude the channel, as shown in FIG. 3C. In theory, this can be avoided by cutting the end of the tube at an angle, but that requires care to insert the tube into the port with the correct orientation so that the tip of the tube does not block the channel. Furthermore, the punched holes are typically sharp-edged and tapered, and the punching process can introduce tears in the PDMS, which can lead to PDMS fragments being pushed into the channel by the end of the tube, spontaneous expulsion of a tube from a port, or leaks. These problems are all avoided by designing molds that allow the production of cast-in-place ports with shoulders that limit the insertion of the tube to a point well above the transverse microfluidic channel, as shown in FIGS. 3D, 3E, and 3F.

A major advantage of the cast-in-place ports is that the location of all ports in a valve or pump are precisely determined. This then makes it possible to connect to the fluidic chip with a rigid fluidic connector. FIGS. 3G, 3H, and 3I show a male-male connector that can be readily produced by either machining or injection molding of a rigid plastic.

Figure 3J:
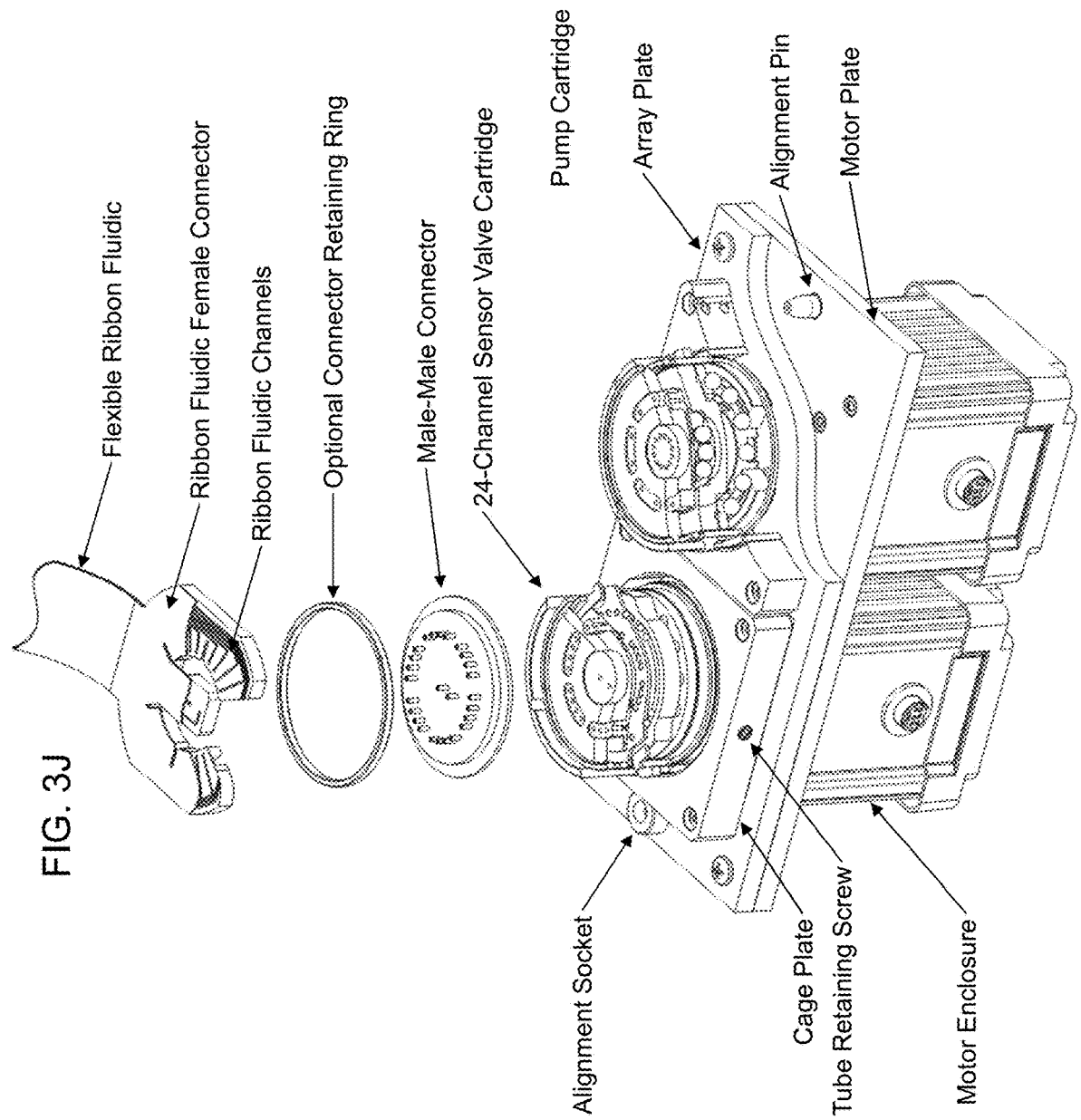
FIG. 3J shows two motors, one driving a 24-channel sensor valve and the other a 12-channel spiral pump, with the two motors being supported by a common motor plate and the cylindrical fluidic cartridges being held to an array plate or fluidic module support structure by commercially available cage plates.

FIG. 3J shows two motors, one driving a 24-channel sensor valve and the other a 12-channel spiral pump, with the two motors being supported by a common motor plate and the cylindrical fluidic cartridges being held to an array plate or fluidic module support structure by commercially available cage plates. FIG. 3J also shows how a flexible ribbon fluidic can be connected to a valve by a male-male connector. The use of alignment pins and sockets simplifies separation and reconnection of the motors on the motor plate from the fluidic cartridges on the array plate or fluidic module support structure.

Figure 3K:
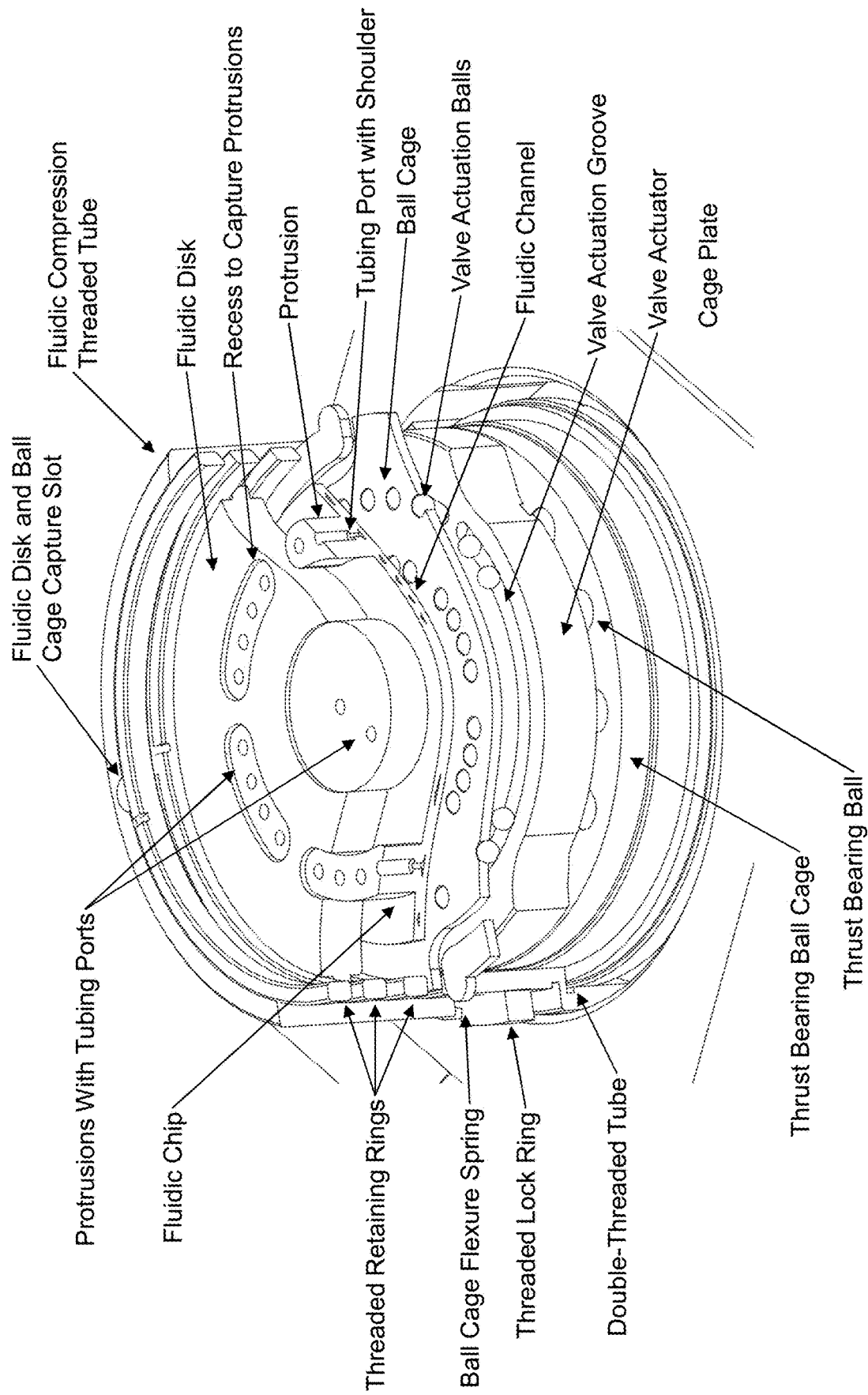
FIGS. 3K and 3L show cut-away views of the valve and pump cylindrical cartridges.
Figure 3L:
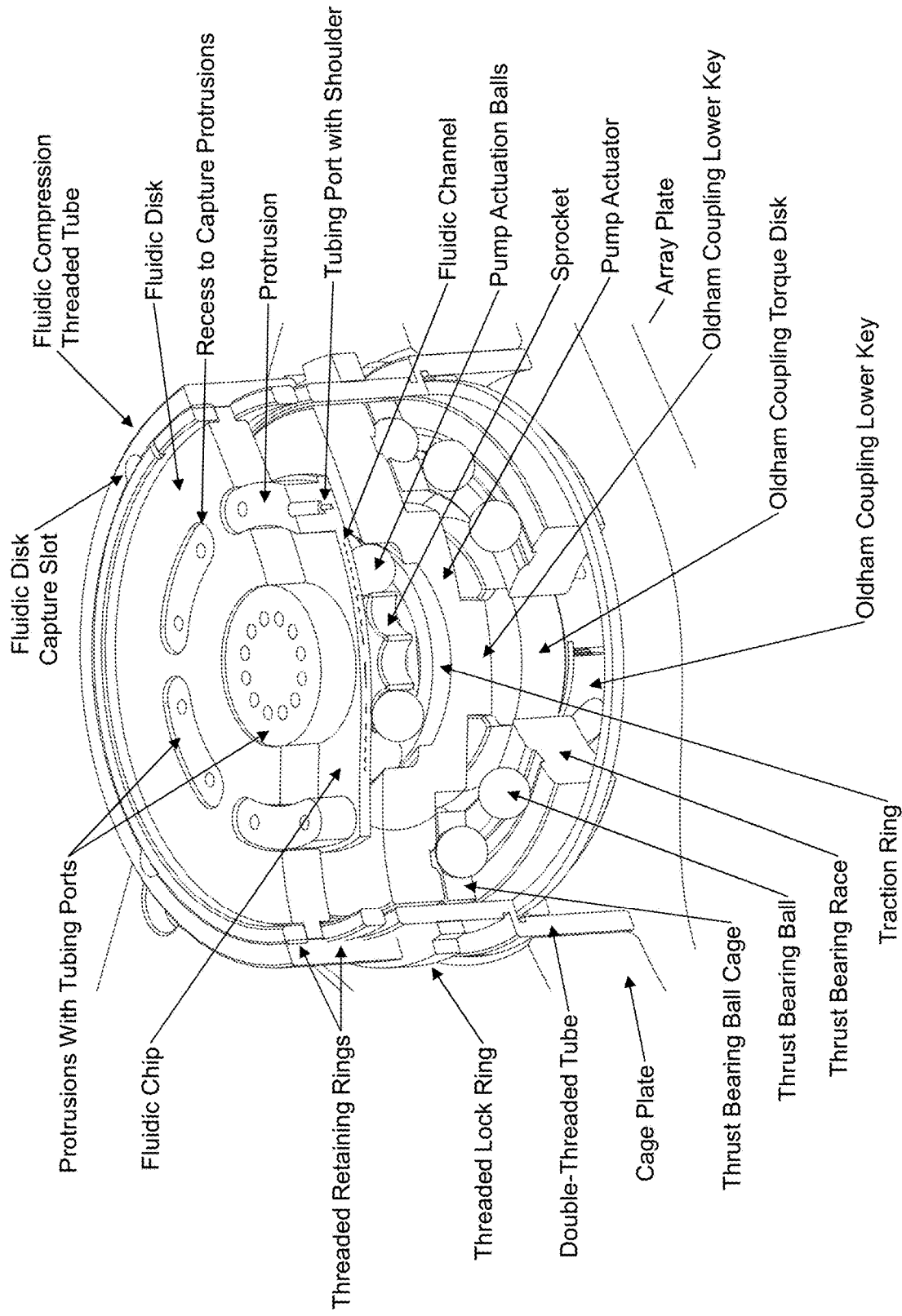

FIGS. 3K and 3L show cut-away views of the valve and pump cylindrical cartridges. The use of a double-threaded tube makes it possible to adjust the compression of a pump or valve simply by rotating the fluidic compression threaded tube and locking it in place with the threaded lock ring. The fluidic cartridge, once compressed, can be inserted into the array plate or fluidic module support structure and held in place with one or more tube retaining screws or other fastening means (FIG. 3J).

Figure 3M:
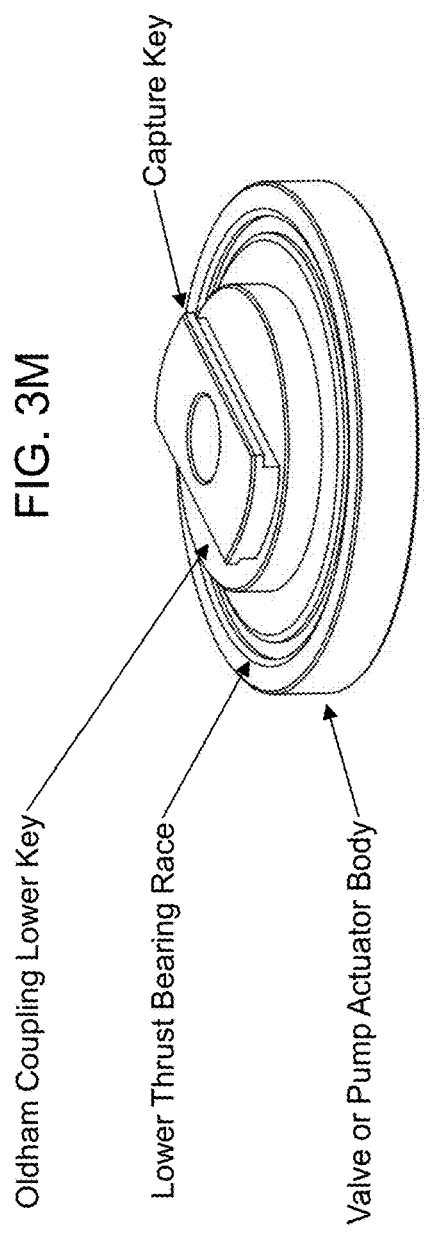
FIG. 3M shows the motor side of the actuator body, with the Oldham coupling key having a capture key so that it will hold in place the Oldham coupling traction disk (FIGS. 3A and 3B) when the motor plate is separated from the array plate or fluidic module support structure.
Figure 3O:
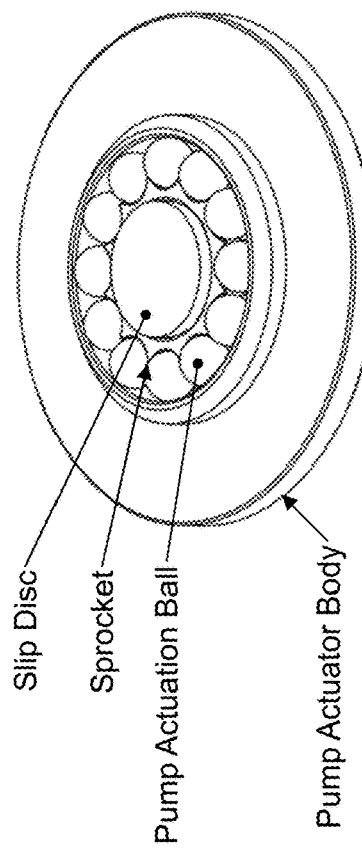
Figure 3N:
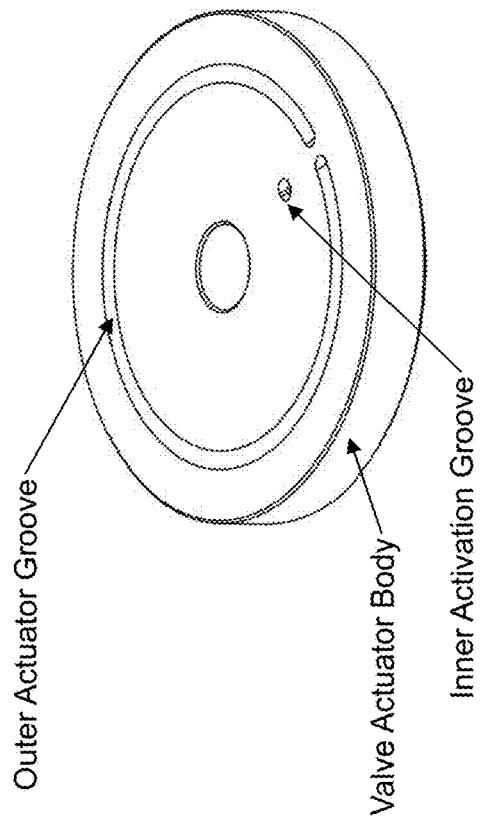
FIG. 3N shows a configuration of the fluidic side of the actuator for a valve.

FIGS. 3M, 3N, and 3O provide details of the valve and pump actuators. FIG. 3M shows the motor side of the actuator body, with the Oldham coupling key having a capture key so that it will hold in place the Oldham coupling traction disk (FIGS. 3A and 3B) when the motor plate is separated from the array plate or fluidic module support structure. The configuration of the fluidic side of the actuator depends upon whether it is for a valve (FIG. 3N) or a pump (FIG. 3O). Because of the pressure required to insert multiple tubes into the tubing sockets at the center of the twelve-channel pump, a slip disk is provided to reduce the distance that the central protrusion is distorted upon tubing insertion. Other types of valves and pumps could have different details on the fluidic side of the actuator.

The modularity of the components in these pump and valve cartridges is central to the economics of this design, which allows the production of a continuous automated perfusion culture analysis system with hundreds of pumps and valves.

Continuous Automated Perfusion Culture Analysis System (CAPCAS)

Figure 4D:
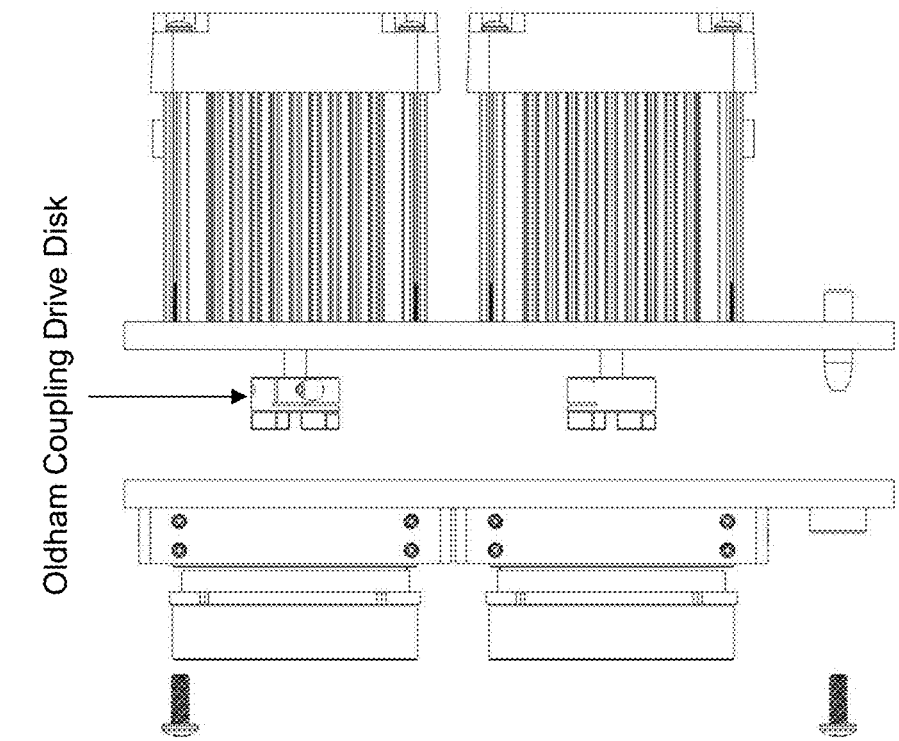
Figure 4C:
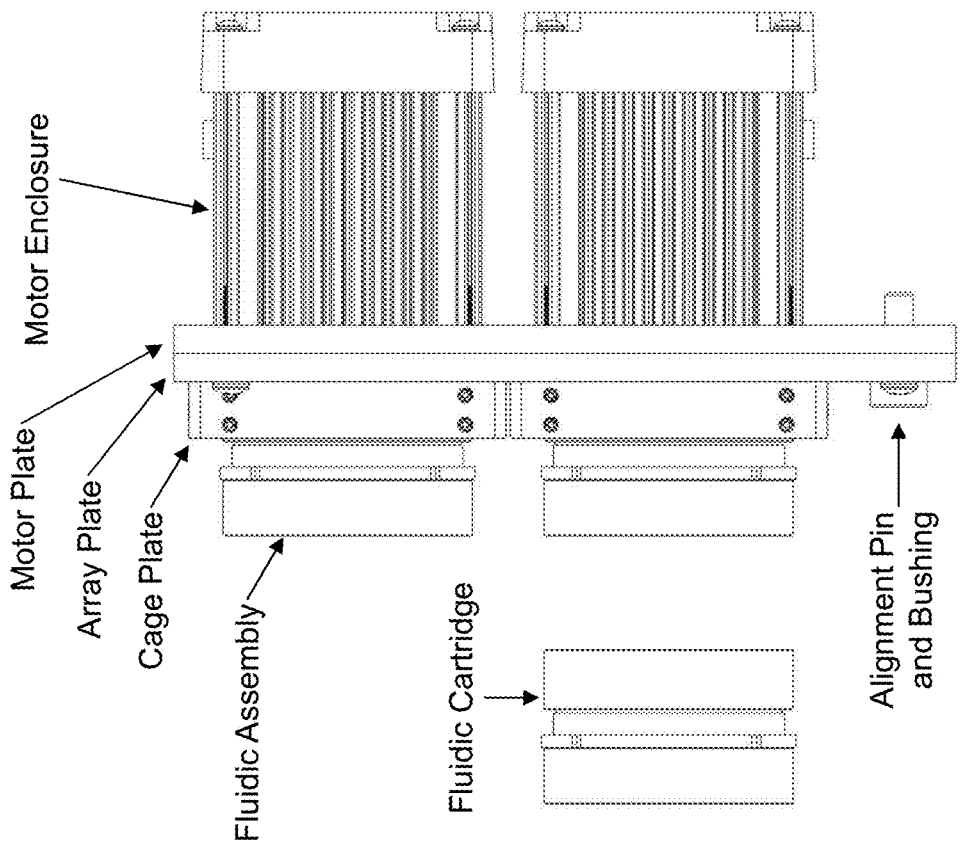
Figure 4E:
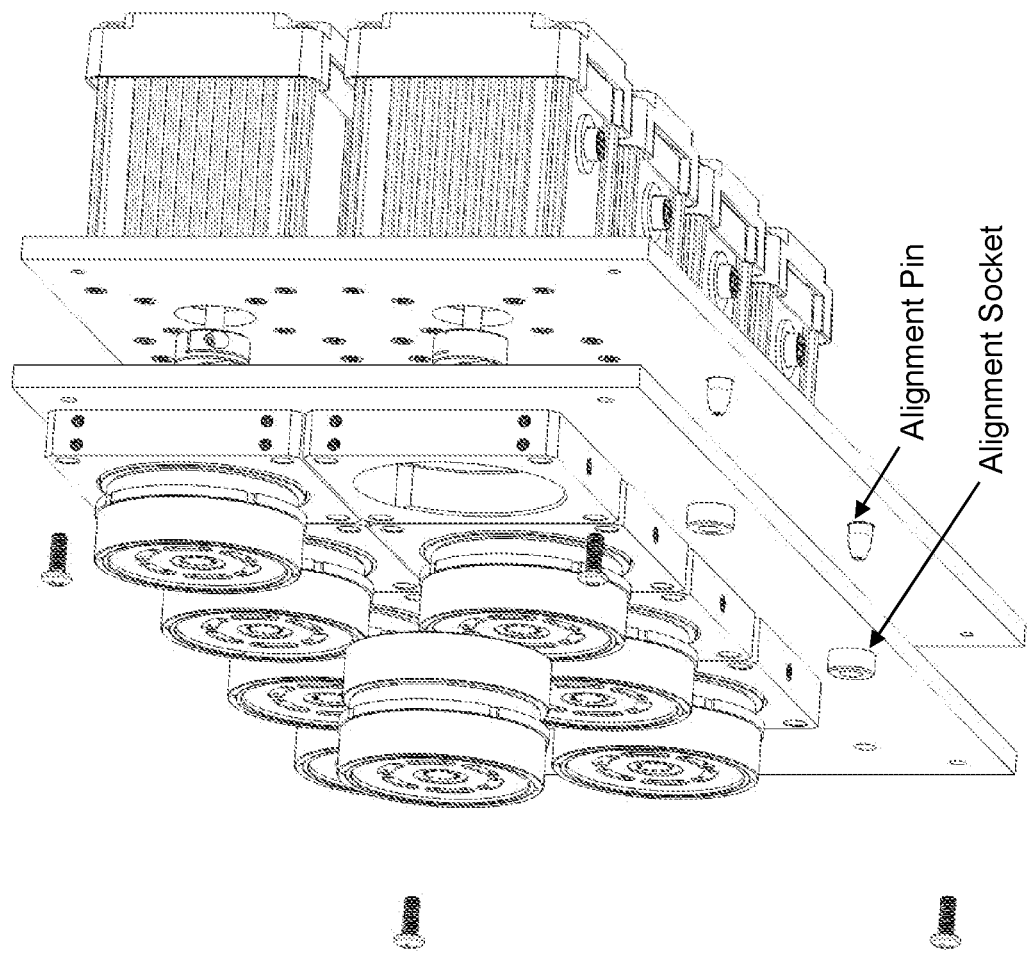
Figure 4F:
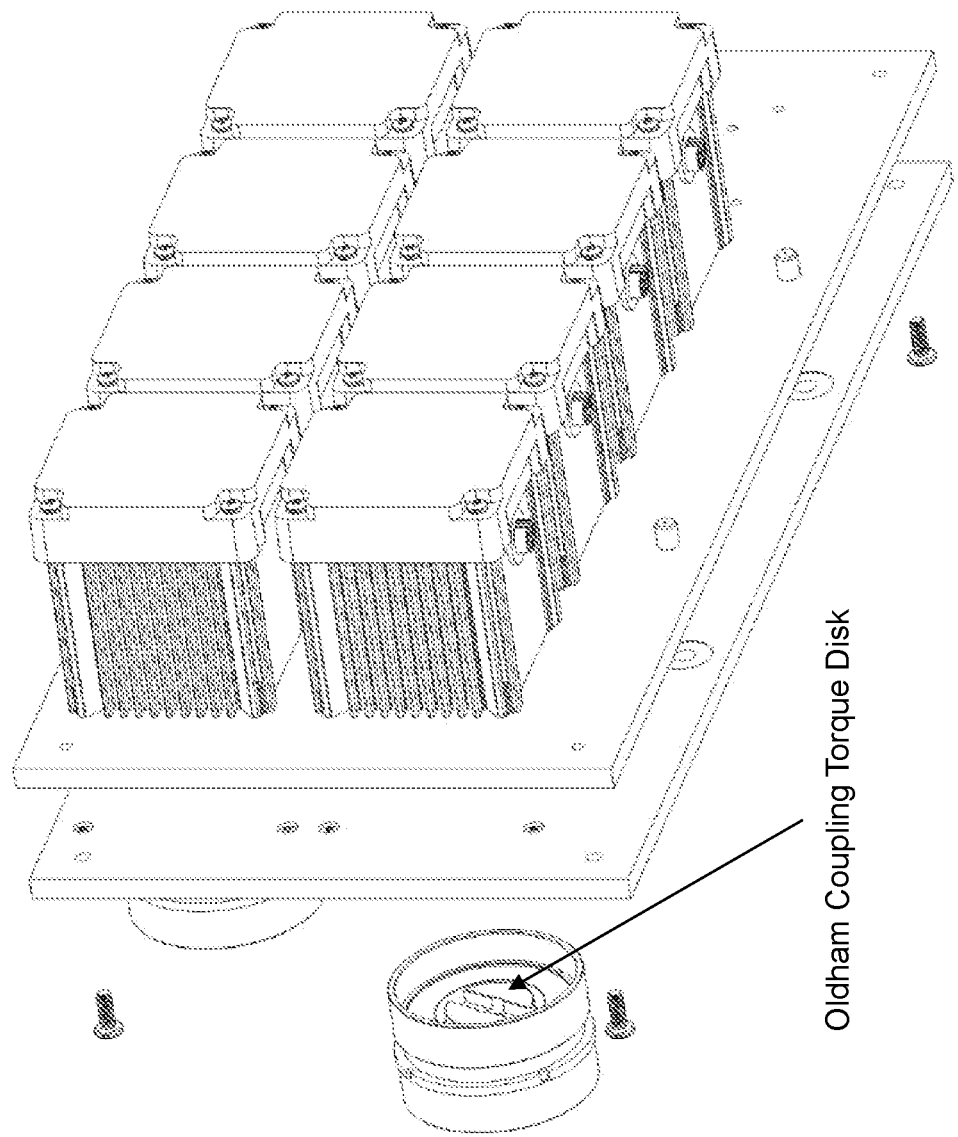
Figure 4G:
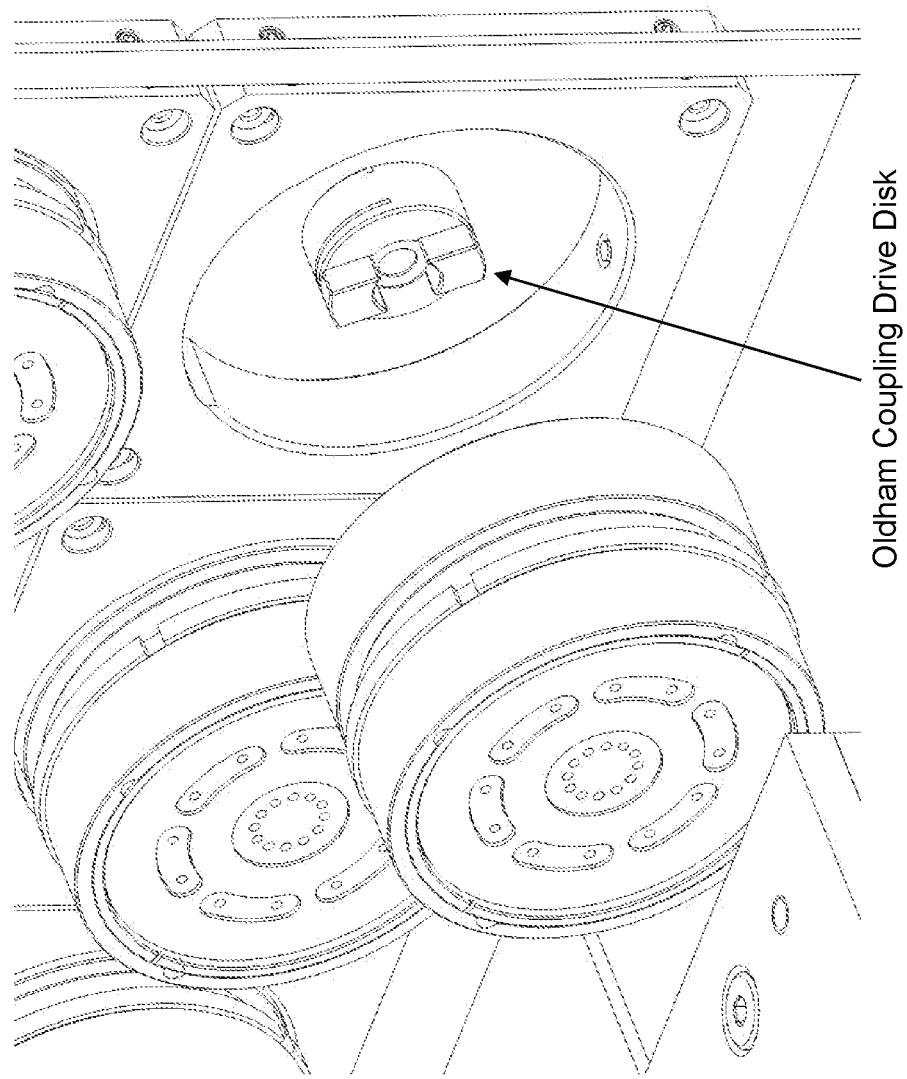

FIGS. 4A and 4B show one embodiment of the chassis that could contain one of the 12- or 48-channel fluidic systems shown in FIG. 1F. The chassis is self-contained and provides sterility and thermal and gas control. There are three drawers, one for the single 96-well input reservoir plate, another for the 48-well deep-well chemostat plate, and the third for one 96-well sample-transfer well plate.

To provide thermal control and ensure easy sterilization of the components in contact with biological samples, there are separate compartments for motors/electronics and fluidics. With this approach, the fluidic circuits in FIG. 1F are divided into sub-modules that can be installed and/or replaced individually and treated as assemblies that would be disposed of or reconditioned after a series of experiments: the input module that contains the media microformulator and the input reservoir plate, the chemostat modules that include the chemostat media delivery pumps, and the output module for chemostat media collection. FIGS. 4C-4G provide details that demonstrate how the motor and fluidic assemblies can be readily connected or separated, as required for exchange of fluidic cartridges to revise an experimental design, to replace worn fluidics, or for sterilization. This approach would obviate the need for a user to interact with the electronic assemblies within the motor compartment. Matching bulkhead connector mounts on the motor plate and the array plate or fluidic module support structure would support connection of the sensors shown in FIGS. 1F-1I with control electronics in the motor compartment or other spaces.

With 100-channel valves and 48-channel pumps (not shown), an embodiment based upon FIGS. 4A-4G can easily support 48 chemostats in a single well plate using the fluidic layout in FIGS. 1F-G. Other channel counts could support differing numbers of chemostats, bioreactors, well plates, or organ chips.

System Sensors

Sensors for electrochemically quantifiable analytes such as glucose, lactate, oxygen, pH, glutamate, alcohol, and neurotransmitters could be implemented individually at the level of each well, chemostat, or bioreactor, or could be located at the output of a sensor valve that can be connected sequentially to capture the effluent of each well, chemostat, or bioreactor. Hence, the calibration of sensors is simplified by either the microclinical analyzer in FIG. 1B or for multiple wells or biodevices, a combination of the 24-channel sensor valve in FIG. 2A and one or more pumps such as those in FIGS. 2E and 2F.

The sensing and regulation of pH, possibly every minute, is critical to the operation of microbial chemostats, particularly when cells are in the log-growth phase. Individual electrochemical pH (or other analyte) sensors could be installed either in the fluidic lines on both the input and output of the chemostat or bioreactor plate, e.g., as shown in FIGS. 1F and 1G, or the one or more on-line analytical instruments connected to the output of V1 in the bidirectional microformulator in FIG. 1H, or as performed by the analysis section in FIG. 1I comprising V3, P4, and V4. The pH sensors could be electrochemical sensors driven by potentiostats, or optically reporting sensor disks. Alternatively, the culture medium could include one or more colorimetric pH reporters for optical measurement of pH. If there were concerns about the biological effects of the colorimetric pH reagents, they could be added not at the input of the bioreactors/chemostats, but at the outputs, where even higher concentrations would be acceptable since the cells could be disposed of after measurement.

There are several ways in which pH can be controlled in the massively parallel CAPCAS. The easiest would be to formulate parallel sets of input reagents that feed V1 in FIG. 1F, one with low pH and another with high pH. The formulation process specified by the CAPCAS control software could then adjust the ratio of all solution pairs used to formulate the media that will be delivered to each well. The time response of this system will be determined by the cycle time between the two input reservoir sets in FIG. 1F, which in turn would be set by the volume delivered to each set of input reservoir wells. To achieve the fastest possible pH control, another set of pumps and valves, and possibly needles, could be inserted into each chemostat/bioreactor to allow direct injection of a strong acid or a strong base, as needed to adjust the pH of that well to the desired value. Similarly, the correcting acid or base could be delivered by two dedicated ports in V1. In any case, the CAPCAS control software would be responsible for the concentration and pH calculations needed to control any or all of the microformulator deliveries.

Critical to chemostat and suspension bioreactors is the measurement of cell density and characteristics. A key challenge in the use of small-volume suspended-cell bioreactors is to measure the number of cells in the bioreactor or the bioreactor effluent. A standard means to do this is to measure optical density (OD), which may require sequential dilutions to allow measurements over a wide range. This is difficult to do with adequate dynamic range using small fluid volumes. As shown in FIG. 1G, it will be possible to include in each chemostat/bioreactor effluent channel an optical sensor with a defined optical path along which the optical density can be measured by using a light source such as a light-emitting diode (LED) and a photodetector such as a phototransistor. Appropriate control of the LED intensity and detector gain can extend the range of OD measurements with a single instrument. Similarly, the optical path length can be chosen to match the experimentally encountered range of ODs to the dynamic range of the OD sensor. Alternatively, sensors with different path lengths could be operated in parallel. Finally, a valve could be added to dilute effluents with very high ODs, again with the diluted fluids being sent to waste rather than being reinjected into the process stream. Finally, an OD sensor could be configured to support measurements or even imaging of the transverse scattering of light along the optical path length, which contains information about the cell size distribution. The multi-channel optical sensing modules in FIG. 1G could thereby measure pH, optical density, other colorimetric or fluorescence reports, or identify the timing of the passage of a small bubble.

The OD measurement system or an equivalent LED/photodetector pair can be used to detect bubbles in any of the lines shown in FIG. 1F or 1G. Given that the pumps and valves can be controlled by the CAPCAS-IT software, the presence, absence, or speed of a bubble can serve as an excellent indicator of whether a reservoir is empty, or the end of a time- and space-limited sample has passed the detector. By proper timing of both pumps and valves, small bubbles could be intentionally injected into any tube and a pair of bubble detectors could be used to measure the time-of-flight of the bubble, and hence the pump flow rate. The bubble could then be ejected from the same port from which it was drawn. We have shown that this approach can be used cyclically with a single bubble to measure flow rates at different pump speeds.

An alternative is to measure the electrical impedance of the cell suspension, either in a bioreactor or a tube containing bioreactor effluent.

Measurement of environmental variables within the CAPCAS enclosure in FIG. 4A would ensure that the chemostats/bioreactors were operating at the needed temperature, humidity, and gas concentrations (if the gas control is through the well-plate headspace rather than in a sealed volume above each well). Airflow and pressures could be measured to ensure that the CAPCAS enclosure pressures were appropriate for the required biocontainment, for example at negative pressure for use in BSL-3 and BSL-4 facilities.

Mass spectrometry can be incorporated into CAPCAS, a feature that will make CAPCAS ideal as a robot scientist in that the samples from each chemostat or bioreactor will be directly injected, after on-line processing, into an on-line mass spectrometer for untargeted metabolomics. We have already shown that it is possible to couple, in real time, the effluent of microfluidic traps containing Jurkat cells to a custom, automated ultraperformance liquid chromatography (UPLC) desalting system and an ion mobility-mass spectrometer (IM-MS). This allowed us to study with three-minute temporal resolution how the cellular metabolome is affected by drugs.[50, 79] While not yet done on-line, as will be possible with CAPCAS, we have used UPLC-IM-MS and MS-MS to study the metabolomic and transport responses of cells in an organ-on-chip model of the blood-brain barrier.[80-82] All of these measurements could be readily performed with CAPCAS. Connections to an adjacent on-line mass spectrometer could be made at fluidic lines on output of the chemostat or bioreactor plate, e.g., as shown in FIGS. 1F and 1G, or the one or more on-line analytical instruments connected to the output of V1 in the bidirectional microformulator in FIG. 1H, or as performed by the analysis section in FIG. 1I comprising V3, P4, and V4.

The heart of the CAPCAS embodiments shown in FIGS. 1D, 1E, 1F and 1G would be an instrument capable of untargeted metabolomics or proteomics measurements, such as would be conducted by direct injection of chemostat effluent into an IM-MS[50, 79, 83, 84] that is preceded by an Agilent RapidFire Solid Phase Extraction (SPE) desalting system[52] that in turn delivers the desalted sample to an Agilent 6560 ion mobility quadrupole time-of-flight (IM-qTOF) mass spectrometer. RapidFire uses 4 ml SPE cartridges with 10 µL sample volumes. The aspirate, load/wash, elute, and re-equilibrate phases require only 10 seconds, and the automatic and rapid SPE cartridge changer allows sequential analysis using different cartridges (e.g., C18, HILIC, and graphitic carbon) for the broadest untargeted metabolite coverage. At 10 seconds per sample, the SPE-IM-MS system will be able to perform three SPE separations in both positive and negative mode for each of the 1,144 chemostats in a CAPCAS every 22.4 hours. Alternatively, a single chemostat could be sampled continuously with a time resolution of 10 s, or other arbitrary combinations can be used.

Transcriptomics data for the cells within each chemostat or bioreactor would be facilitated by the use of the output plate in FIG. 1F, in that at the end of an experiment, half of the cells would be removed and delivered, well-by-well, to the output plate, while the other half would remain in the chemostat plate. Both plates can be quickly removed from CAPCAS, one processed for both extracellular and intracellular proteomics and metabolomics,[85] and the other for untargeted transcriptomics using RNAseq or another platform. In the embodiment in FIG. 1G, there are two output plates, one of which could be used to collect effluent from each chemostat while the effluent previously collected in the other output plate is being analyzed. Should an on-line transcriptomics analyzer be developed, it too could be connected to the system by the sensor valve.

The advantage offered by the pump and valve hardware that enables CAPCAS is that hundreds or even thousands of different experiments could be conducted in parallel, providing correlated multiomics data sets that would be ideally suited for analysis by deep-learning neural networks and other AI techniques to establish heretofore unrecognized correlations between genes, proteins, and metabolites. Such experiments could be performed in either classical, open-loop mode with the human operator specifying the experimental parameters and cell strains studied, or in a robot-scientist, closed-loop mode where the AI/ML software guided these selections. It is worthy of note that any delays associated with cell processing, measurement, and the AI/ML analysis of the large multiomics data sets could be accounted for by interleaving multiple experimental series into a master set of experiments, such that the time interval between any particular experiment type would be set by the total analysis delays for that group. The longer the delays, the larger the number of different experiments that would be interleaved in the master set of experiments. The interleaving of measurements and bioreactor control for multiple experiments is made possible by the multiple channels of our pumps and valves.

There is an extensive literature on the use of Raman spectroscopy to monitor metabolism during yeast fermentation, the culture of other microbes, and the culture of mammalian cells[55-66, 86-88] As discussed for pH sensing, it would be straightforward to connect the CAPCAS sensor valve (V3) in FIG. 1F or the sensor selector valves (V4) in FIG. 1I to one or more analytical instruments. Note in FIG. 1F that a calibration valve (V3) can be used to calibrate any of the many possible down-stream sensors.

UV-Vis spectroscopy or imaging could be readily accomplished by using the same valves in FIG. 1F or 1H, and would enable the quantification of genetically encoded reporter genes that reflect a particular signaling or metabolic pathway. Cell morphology could be assessed on the cells exiting the chemostat or bioreactor by having some fraction directed through a sensor valve to pass through a microfluidic imaging system, either as continuous flow with a fast camera or stop-flow with a slower one. Similarly, the chemostat effluent could be connected to a microfluidic or larger Coulter Counter, a microfluidic cell sorter,[89] a fluorescence-activated cell sorter (FACS), or a CyTOF instrument. While FACS and CyTOF and other analytical instruments are expensive, having them directly connected to a large version of CAPCAS would be cost effective because hundreds or thousands of different experiments might be operating at the same time, keeping the instrument fully occupied and not requiring manual sample handling. The multi-port pumps and valves that are the subject of this invention make it possible to utilize a small number of sensors to measure and control a much larger number of bioreactors, organ chips, or other bio-objects.

For many of these approaches, sample preprocessing might be required, which could be accomplished using on-line microfluidics, for example parallel spiral cell sorters[68] that could allow the use of two output plates, one with media only and the other with highly enriched cells or cell lysers.[90, 91] It may be necessary to mix the chemostat effluent stream with agents to halt metabolism or lyse cells prior to freezing.

System Controllers

Given the large number of chemostats, bioreactors, well plates, or organ chips that will be serviced by this system, it will be necessary to implement a number of different automated control systems. Our novel microfluidic rotary planar peristaltic micropump (RPPM)[31-33] and rotary planar valve (RPV),[36] both powered by NEMA-17 stepper motors with a custom microcontroller and computer software to drive the system, enable the combination of a pump and valve in the microclinical analyzer in FIG. 1B and the microformulator in FIG. 1C. In present embodiments, the motors in the pumps and valves are DC stepping motors, often with angle encoders. Other motor types could be used, including brushed and brushless DC motors. In any case, to achieve the level of control of angle, velocity, and torque required for proper operation of the systems, each motor requires an independent controller, for example in the form of a dedicated microprocessor that controls the motor driver chip based upon factors such as the motor drive current and angular displacement of the motor. These controllers can be housed either within the motor enclosure or outside it, depending upon the design parameters and requirements for the system. With the enclosure architecture in FIG. 4A, the sealed motor compartment obviates the need for individual motor enclosures, as are shown in the figure.

We have previously described our Automated MultiPump Experiment Running Environment (AMPERE) software to control the pumps, valves, and ancillary equipment used in our microfluidic systems. AMPERE is digitally interfaced to CCD cameras for flow tracking, electronic scales for gravimetric autocalibration of RPPM/RPV systems, WiFi routers and a Network Time Protocol (NTP) server, and a variety of commercial flowmeters, valves, and other hardware. AMPERE could control the hundreds of motors that will be operating within an embodiment of CAPCAS, but as we will discuss below, its architecture does not support parallel, asynchronous operations that have feedback to control conditional operations. As discussed in detail in U.S. Pat. No. 11,447,734 B2, the CAPCAS platform can be controlled by a database-driven software system, termed CAPCAS-IT, that can readily interface to computers that are using artificial intelligence and machine learning to allow CAPCAS platforms to operate as self-driving biological laboratories, also known as robot scientists.

In this section, we discuss the physical controls that are needed to operate CAPCAS such as the embodiments in FIGS. 1F-1I.

A number of chemostat parameters would need to be controlled, including temperature, pH, media feed rate, nutrient and inhibitor levels, dissolved oxygen, and possibly carbon dioxide. There should be corresponding sensors as discussed above to validate that these parameters are in fact accurately controlled. It is necessary to determine the physical extent of the control. While it will be possible to control nutrient levels at each well, it will be possible but more complicated to provide different gas concentrations to adjacent wells. Thermal conductivity issues would suggest that a single plate should be at a uniform temperature; some embodiments of CAPCAS require that in a multi-plate system, each chemostat/bioreactor plate would be isothermal. One of the advantages of having AI/ML software design the individual experiments would be that experiments with similar parameter values, such as oxygen concentration, could all be performed on the same plate at the same time. It would then be possible to change these parameters during the next fermentation experiment.

In addition to motor control, plate control is needed to move plates in and out of the operational envelope while maintaining the sterility and cleanliness of each plate. As detailed in U.S. Pat. No. 11,447,734 B2, the sequence of events would be as follows: The user inserts the well plate into the tray in one of the drawers shown in FIG. 4A. The tray moves into the operational envelope; if lidded, the lid will be removed and stored in such a way that it will be put back on the plate when the plate is extracted. The plate tray is lifted up to mesh the plate with the fluidic interface element. In systems with a large number of plates and the associated fluid handling stations, chemostat plates can be delivered, inserted, and removed by iPlateBot robots as described in U.S. Pat. Nos. 11,447,734 B2 and 11,474,531 B2.

CAPCAS Interfaces to Other Systems

With the growing recognition that continuous culture provides major scientific benefits over batch culture in well plates and bioreactors, there is a pressing need for parallel, small volume, automated perfusion bioreactor systems. The pumps and valves that comprise CAPCAS will provide researchers with a large array of instrumented and precisely controlled microliter-per-minute or faster perfusion systems that enable massively parallel microbial- and mammalian-cell experiments that can be connected directly to an SPE-IM-MS system for metabolomics and operated as self-driving laboratories that benefit from the power of machine learning. Basic microbial science, pharmacology, and commercial biomanufacturing will all benefit from massively parallel experiments that can refine models of cellular signaling and metabolism, allowing researchers to explore connections that were previously beyond their grasp. CAPCAS provides a platform that can be produced in quantity and will be replicated at a cost well within the reach of both academic and industrial research groups.

A key difference between cells cultured in static media on flat plastic or Transwells and cells grown in organ chips is that the latter, because of their small fluid volumes, are most often perfused dynamically using syringe pumps, peristaltic pumps, gravity acting on input reservoirs that are higher than the outlet reservoirs, and pressurized reservoirs. The improved physiological recapitulation afforded by organ chips and the desire to avoid anoxic cores in thick tissue bioreactors and large organoids are contributing to a rapid growth in the perfusion of a variety of cell culture preparations. Some organ chips are operated on a rocker, with fluidic channels typically configured to provide bidirectional flow as an array of chips is rocked back and forth. It is possible to create fluid channels that support unidirectional flow, but these are not yet widely utilized. Gravity perfusion, syringe pumps and pressurized reservoirs all suffer from the limited volumes of reservoirs and the difficulty in having the effluent from one organ perfuse a second, downstream organ. The flow rate in stationary gravity-perfused systems drops steadily as media flows from the input or supply reservoir, whose level drops, into the outlet or collection reservoir, whose level rises. The steadily decreasing difference in reservoir height translates into a steadily decreasing flow rate. Typically, on a daily basis or even more frequently, media is manually withdrawn from the collection reservoir and either new or conditioned media is added to the input reservoir. The required rate of media replacement to maintain cell viability is determined primarily by the number of cells being cultured, with the rule-of-thumb that a cell with a picoliter volume requires a nanoliter of fresh media each day. While rocker and pumped systems allow reuse of media, the problem of media replacement remains.

Syringe pumps and pneumatic and roller-based peristaltic pumps can be used to perfuse and even interconnect organ chips, but it is important to avoid the introduction of bubbles into vascular channels, since a passing bubble can severely disrupt the endothelial cells that line the channel. Hence, these perfusion systems often include a bubble trap to capture any pump-introduced bubbles or bubbles that appear within a length of tubing or a microfluidic channel due to temperature changes affecting gas solubility. In contrast to pumped systems, gravity-perfused ones seldom encounter bubble problems because the reservoirs are open and any bubbles rise to the surface, burst, and disappear.

Regardless of the perfusion method, organ chips typically require a high level of human attention to refill syringes and pressurized reservoirs, provide fresh media to peristaltic-pumped and gravity-perfused systems, and remove waste media. This in turn severely restricts the level of parallelization and automation that has been achieved with organs-on-chips.

Figure 1J:
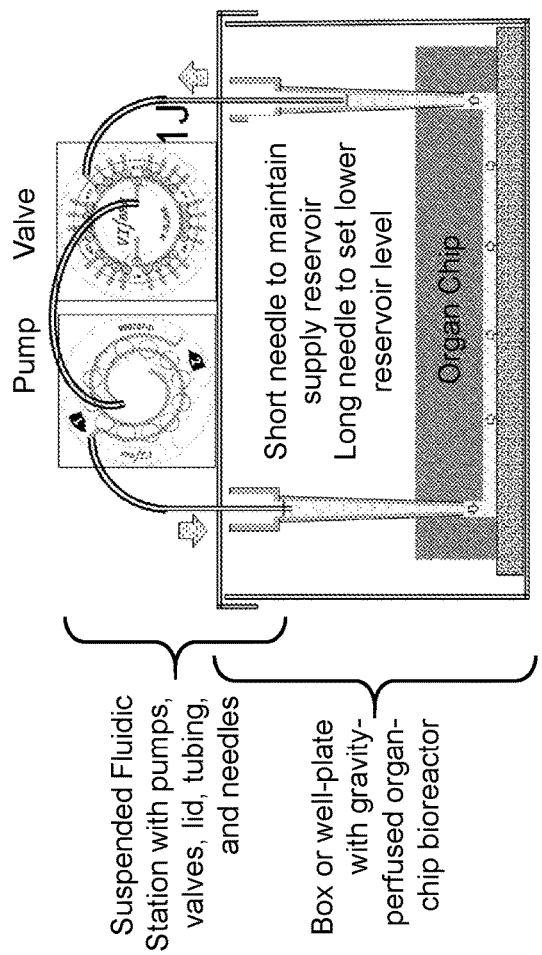
Figure 1L:
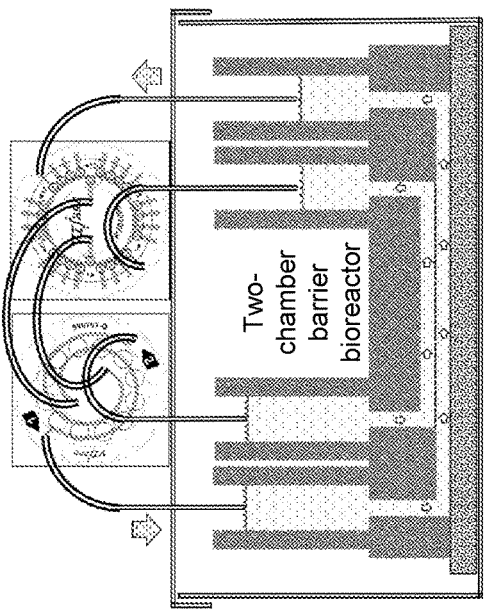

Many of these problems can be overcome by using a CAPCAS unit in a way that merges pumped and gravity-perfused systems and enjoys the benefits of both. The fluidic control system of this invention can be used to maintain automatically and without human intervention a uniformly high level of media in the delivery well of a gravity-perfused bioreactor while also removing fluid from the collection well to keep a low fluid level and hence a constant gravity perfusion rate, in contrast to the ever-decreasing rate in unattended gravity perfusion systems. Gravity perfusion on organ chips frequently uses water column heights of 20 mm or less, as can be readily achieved with a pipette tip inserted into a microfluidic chip. This corresponds to a pressure of approximately 200 Pa. FIGS. 1J-1M show how a short supply needle and a long collection needle can be inserted in the upper and lower gravity perfusion reservoirs, respectively. These needles can be connected to CAPCAS pump and valves just as were the chemostats and bioreactors, such that the delivery, removal, and analysis of fluids does not require human intervention. If one or more organ chips are placed in a well-plate-sized box, the iPlateBot can move these chips between different stations in an enclosure. Interconnections between organ chips can be designed into the pump, valve, tubing, and needle networks but connecting, for example, the collection needle from the outlet reservoir of one organ chip to the inlet reservoir of another organ chip. While FIG. 1J shows this for a pipette-tip gravity-perfused system, FIG. 1K extends this concept to an organ chip with integral fluid reservoirs. The decision of what fraction of the media is to be returned to a supply reservoir need not be made at the time of the fabrication of the chips, but instead by controlling the settings of pumps and valves already in the CAPCAS unit. FIG. 1L shows that the addition of more needles and more pump and valve channels allows this approach to be applied to a two-chamber barrier reactor, such as a neurovascular unit and the blood-brain barrier that it contains. Finally, closely placed needles would allow both the insert and the outer well of a Transwell chip to be perfused separately, as shown in FIG. 1M. While these drawings show only a simple pump and valve on a single organ chip or Transwell, the CAPCAS fluidic circuits already described could support multiple organ chips as easily as they support arrays of chemostats or bioreactors. The pump and valve above each of these boxes is meant to serve as a schematic representation of a multi-channel fluid-delivery and removal/perfusion/recirculation system. An array of such systems could be suspended in a larger enclosure and an iPlateBot plate transporter could shuttle these boxes between various stations, as discussed in detail in U.S. Pat. Nos. 11,447,734 B2 and 11,474,531 B2. The purpose of the boxes shown in FIGS. 1J-1M is to ensure sterility and humidification of the open reservoirs used to perfuse each biodevice. When the box is being transported, it is covered with a lid, just as is a well plate being transferred. When the box is delivered to the CAPCAS fluidic interface station, the box can be de-lidded and lifted into position beneath a suspended fluidic interface station using the same sequence of events, with the possibility that more vertical distance will be required between the deck and the de-lidding or fluid interface stations to accommodate the height of the box being greater than a well plate. When the box is in place in the fluidic interface station, the lid built into that station will ensure sterility of the contents of the box, including the sterile reservoirs therein.

The full automation of organ-chip perfusion would be particularly useful now that organ-chip viability is extending to many months, i.e., for long intervals of time that would otherwise require dedicated and attentive human technicians to both maintain chips and conduct pharmacology and toxicology experiments on them.

As another example, zebrafish embryos are used extensively in physiological studies because of their small size and transparency and the ease with which they can be altered genetically. The care and feeding of massive farms of these embryos can be time consuming, as are pharmacological experiments on them. Because CAPCAS can perfuse Transwells (FIG. 1M) such as those used to grow zebrafish embryos, it would be a straightforward extension of CAPCAS to the study by a robot scientist of zebrafish physiology.

One-Eight-One Pump Chip

Figure 5A:
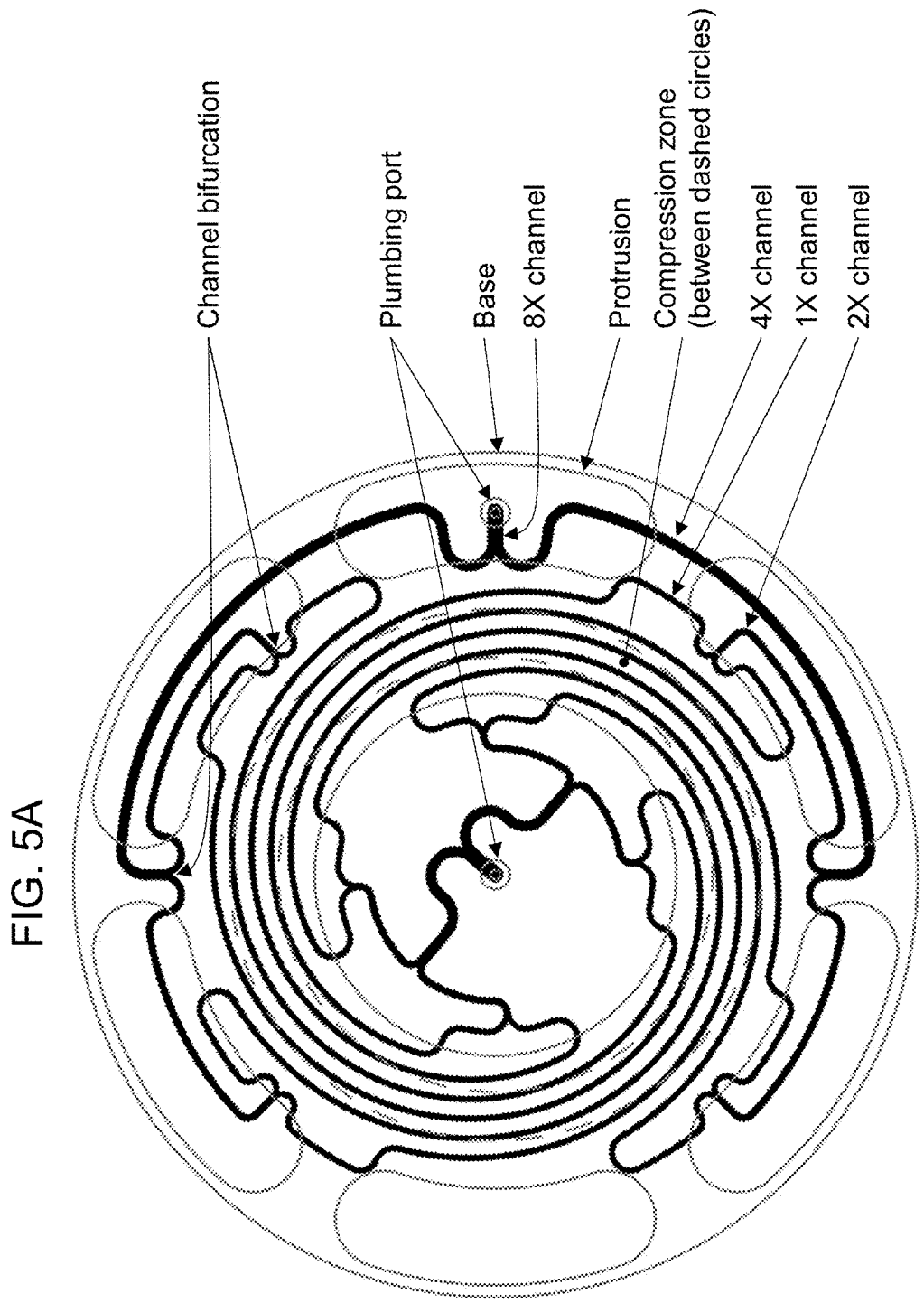
FIGS. 5A-5B show details of the one-eight-one manifold pump also shown in another embodiment in FIG. 2H, according to embodiments of the invention.
Figure 5B:
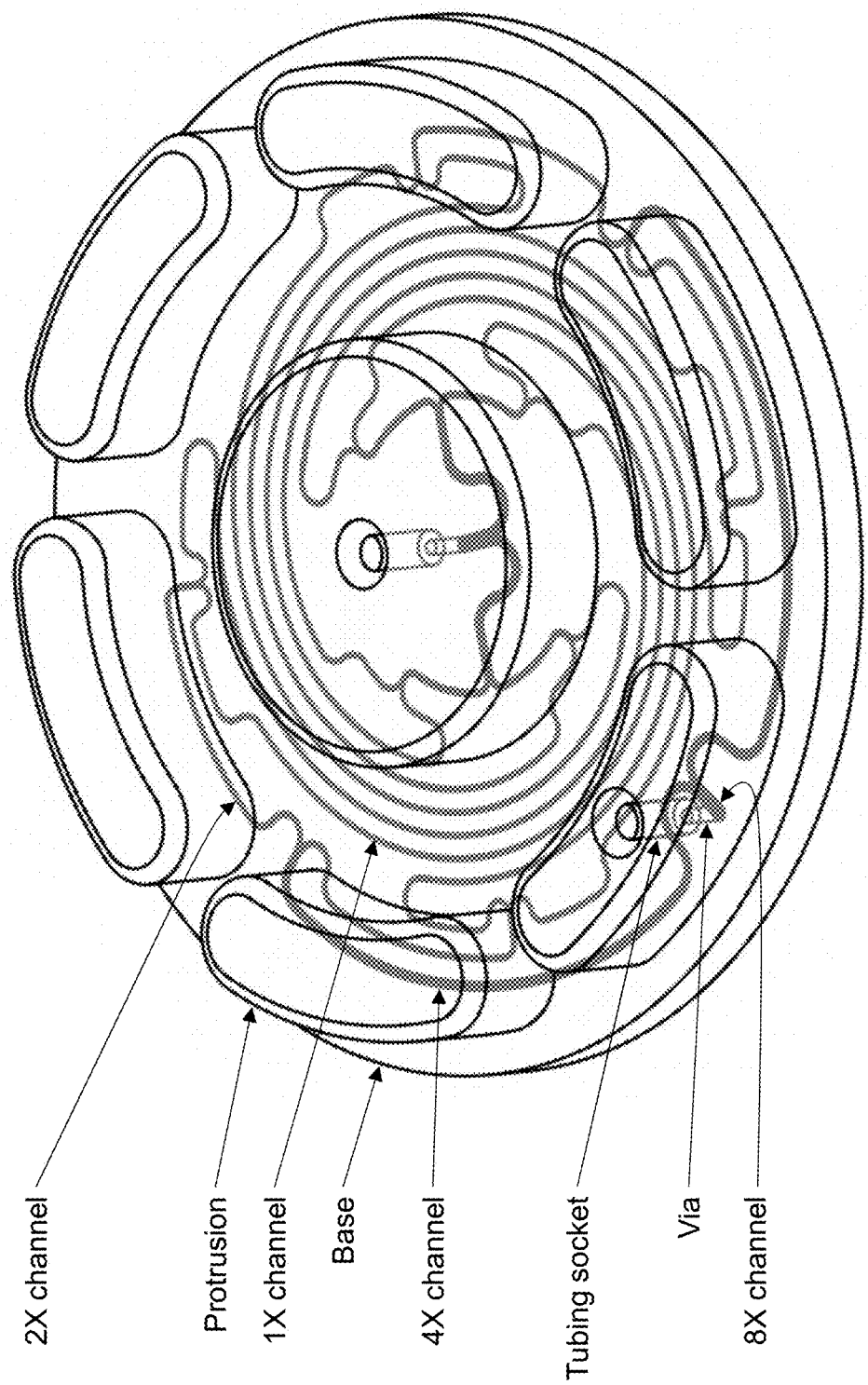

The one-eight-one pump chip shown in FIG. 2H and in more detail in FIGS. 5A and 5B features eight spiral channels that are directly, mechanically acted upon by the pump assembly's actuating elements. The downstream terminus of each spiral channel is a bifurcation, in which that channel converges with another, similar channel. The resulting channel, thereby carrying fluid from two spiral channels during pump operation, has a cross-sectional area that equals the sum of the cross-sectional areas of each of its contributing channels, and therefore can carry twice the fluid volume. We call this a 2X channel accordingly, and the spiral channels are termed 1X channels. The 2X channel, in turn, converges with another, similar 2X channel to form a 4X channel, whose volumetric flow rate is four times that of a 1X channel. After one more bifurcation, an 8X channel delivers all the fluid being pumped through the chip to a plumbing port, which is used to connect the pump chip to an external conduit such as flexible tubing.

The fluidic network upstream of the spiral channels is configured the same way as the downstream network, wherein an 8X channel begins at a plumbing port, splits into two 4X channels, and so on until the path reaches the spiral channels. Whereas fluid converges at the downstream bifurcations, it diverges at the upstream bifurcations. The pumping direction may be reversed by changing the rotational direction of the pump's actuator. Hence this design utilizes eight parallel pumping channels, each end of which is connected to a binary splitter network.

The merit of this design is that it provides a very high flow rate with very low pulsations.

Self-Centering Oldham Coupling Mechanism

FIGS. 3A-3B provide details regarding one embodiment of the invention that uses an Oldham coupling to allow mechanical separation of one or more motors from their fluidic cartridge, and thermal isolation during operation. We present the Oldham coupling as a coupling mechanism designed for use in our fluidic handling systems that compensates for axial misalignment—angular, parallel, and normal—between a driving construct and a driven construct, with little or no rotational backlash. The mechanism consists of three parts: input coupling, torque disc, and driven construct. In one embodiment, the driven construct is an actuator used directly in the operation of a pump or valve. In another embodiment, the driven construct is a second coupling that would mate with yet another coupling, thereby allowing further constructs to be connected to the drivetrain in a daisy chain fashion.

The torque disc consists of an upper slot that mates with the coupling boss, and a lower t-slot that mates with a t-boss in the driven construct. In this manner, the driven construct is permitted only two degrees of freedom relative to the torque disc, which would be translation along and rotation about an axis parallel to the length of the boss/slot. All other degrees of freedom between the torque disc and driven construct are constrained. The design of the upper slot/boss combination constrains three degrees of freedom between the torque disc and the coupling: rotation about an axis parallel to the input shaft, translation in a direction normal to the length of the boss/slot, and rotation about an axis parallel to the length of the boss slot. All other degrees of freedom between the coupling and torque disc are permitted. The combination of these constraints across the coupling, torque disc, and driven construct results in the ability to preserve rotation of the driven construct caused by the input shaft even if the rotational axes of these elements are misaligned. Furthermore, this combination allows for varying distance between the coupling and the torque disc along their respective axes of rotation.

To compensate for slight rotational misalignment between the coupling and coupling slot during assembly, we have incorporated an alignment chamfer in the coupling slot. This oblique entrance to the coupling slot will bring the two parts into precise alignment as they are mated, and can tolerate ±4.5° of initial rotational misalignment.

Figure 6:
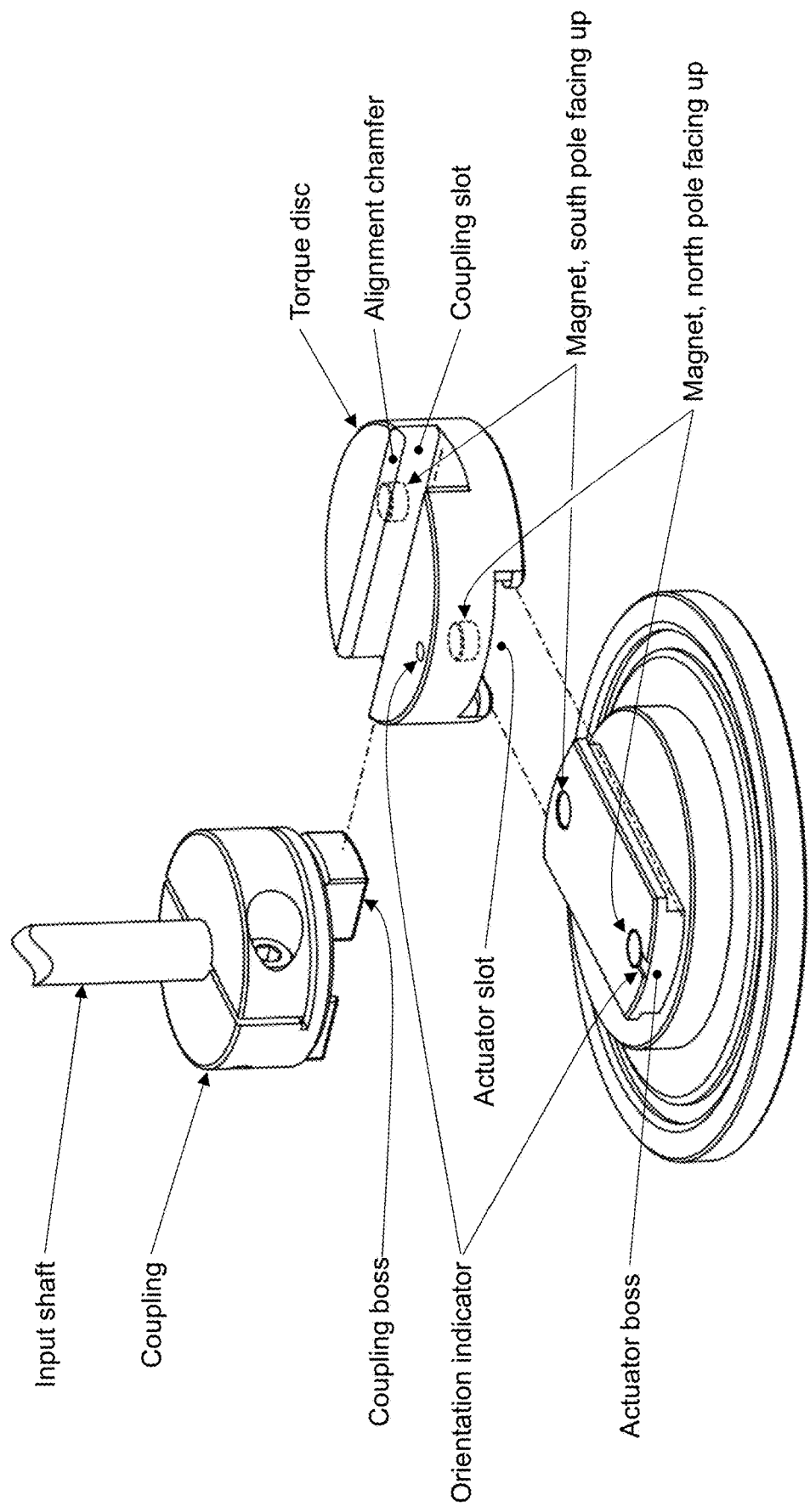
FIG. 6 shows a magnetically captured, self-centering Oldham coupling that improves upon the ones shown in FIGS. 3A, 3B, and 3L, according to embodiments of the invention.

In some applications it is beneficial to ensure that the torque disc remains concentric with the driven construct as it is being mated to a coupling. One of the difficulties with the design shown in FIGS. 3A-3B is that manipulations of the motor or fluidics modules prior to or during mating of the two parts can lead to the torque disk sliding from its ideally centered location coaxial with the other parts of the Oldham coupling. For example, when the present coupling mechanism is employed in the context of a fluidic cartridge, it would be disadvantageous during installation of that cartridge were the torque disc to slide away from the center of the actuator because it then becomes impossible to mate the cartridge with the coupling unless it is in exactly the correct rotational position wherein the coupling boss and coupling slot are aligned. For this reason we have outfitted the torque disc and the actuator with polarly opposed magnet pairs as shown in FIG. 6. Magnetic attraction keeps the torque disc centered on the actuator and resists movement therefrom. Because the torque disc and actuator are not mechanically locked together by the magnetic fields, translational motion between the two parts is still permitted, and the parts may be completely separated if desired. If the torque disc is installed backwards onto the actuator, the magnetic repulsion between the polarly opposed pairs will move the torque disc to a position in which it will be obvious that assembly was incorrect.

An additional feature of the present invention is the orientation indicator. These are marks on the actuator and the torque disc that are visible when underlying features are hidden. For example, when the mechanism is part of a fully assembled valve cartridge, an observer can determine the rotational position of an actuating groove on the far face of the actuator, which is not visible from that perspective, based on the position of the visible orientation indicator. The orientation indicators may also be used to aid in coupling the mechanism assembly; when the torque disc is in the proper orientation relative to the actuator, the indicators will line up.

In-Line Gear Reduction Adapter

The connection between the motor and the fluidic actuator in FIGS. 2A-20 through 4A-4G are all direct drive and in some cases include an Oldham coupling. That limits the torque and rotational velocity of the fluidic to that of the motor. The in-line gear reduction adapter in FIG. 7A was developed primarily to reduce the ratio of a pump actuator's speed relative to the driving motor's speed, but it could also be used to increase that ratio, or to increase the precision by which valve actuating features can be located relative to fluidic chip features. While the operating principles of a planetary gearing system are well known and have been previously described, here we present an embodiment that is specific to our fluidic handling technology. The mechanical gear reduction adapter in FIG. 7B has a ring gear, sun gear, and a system of planetary gears enclosed within a tubular housing. The selection of which of the three components is connected to coupling boss 1 and which is connected to coupling boss 2 will determine the relative direction and velocity of rotation of the two couplings, providing either a decrease in rotational speed accompanied by an increase in delivered torque, or an increase in rotational speed and decrease in available torque.

Figure 7A:
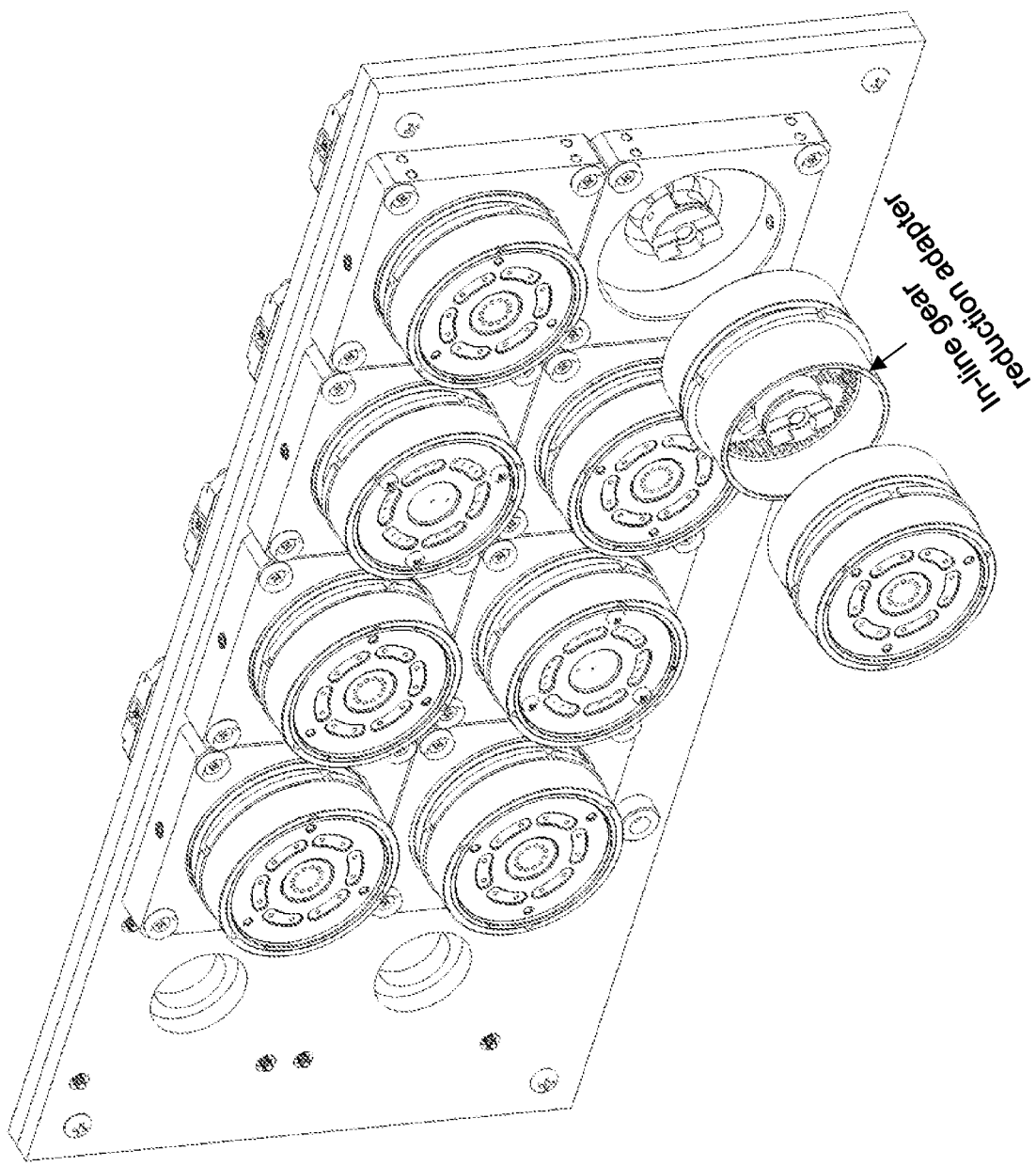

One of the benefits of the present invention is that as shown in FIG. 7A, one or more adapters can be installed between a driving element (e.g., a motor, or to another adapter) and a driven fluidic cartridge without any further modification to the system. Because the coupling features on the motor, the adapter, and the fluidic cartridge are designed to mate with neighboring couplings, the gear ratio of the system can be adjusted simply by removing the fluidic cartridge, attaching the adapter to the construct that was driving the cartridge, and replacing the cartridge at the end of the drivetrain.

Figure 7B:
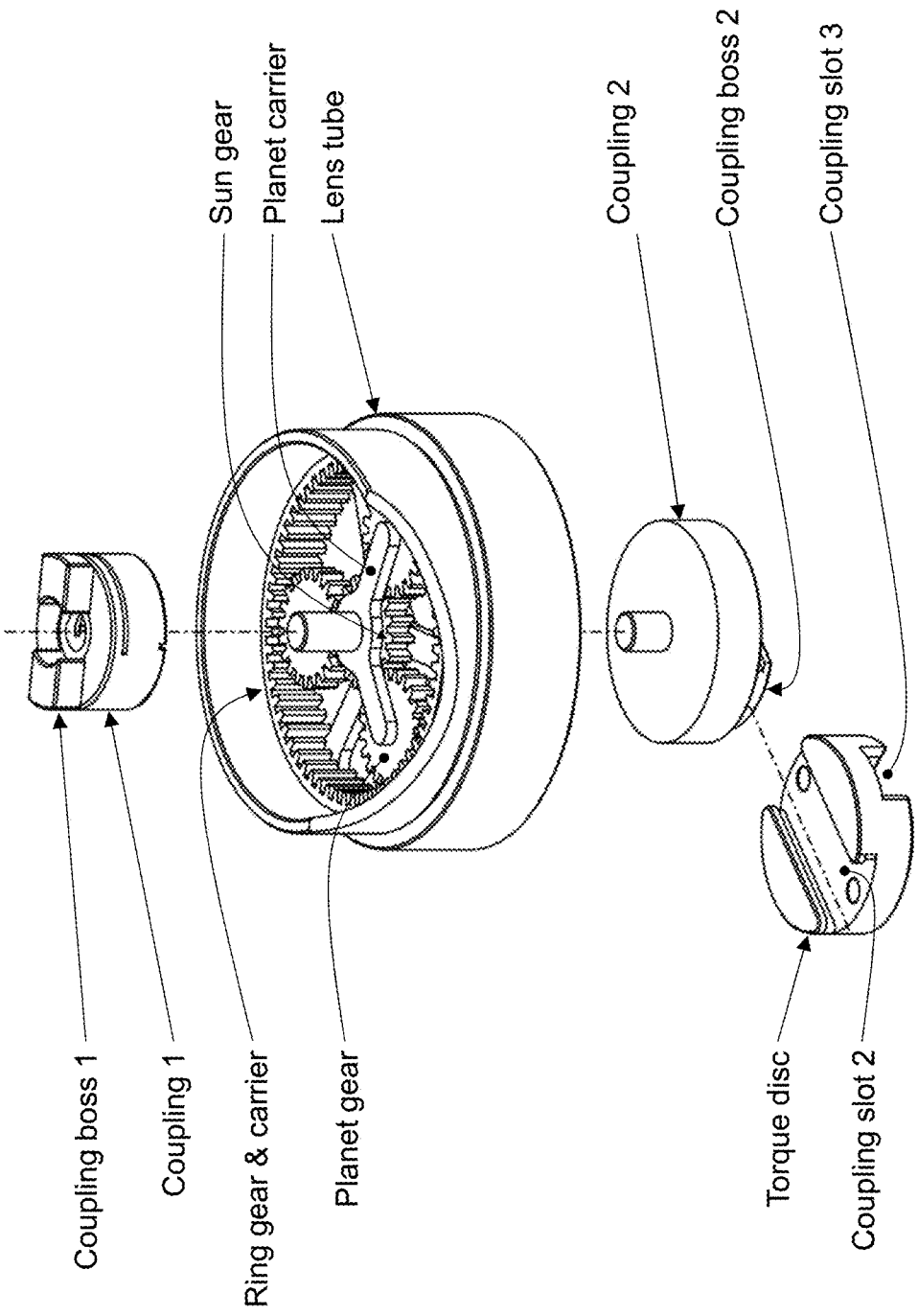
Figure 7E:
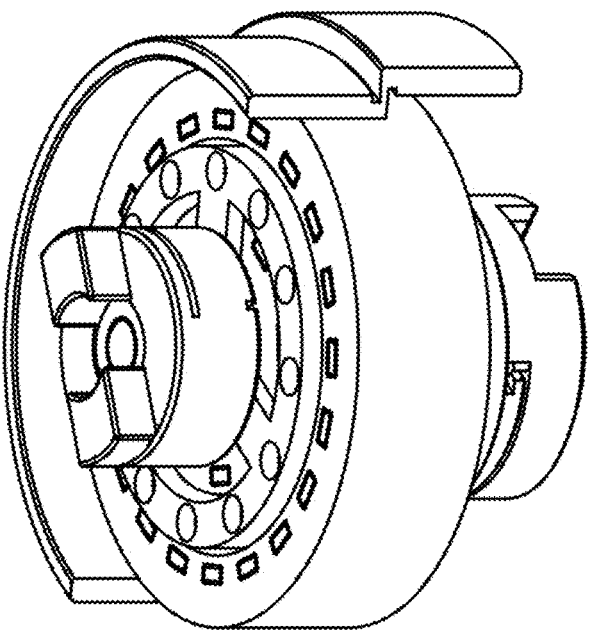
Figure 7D:
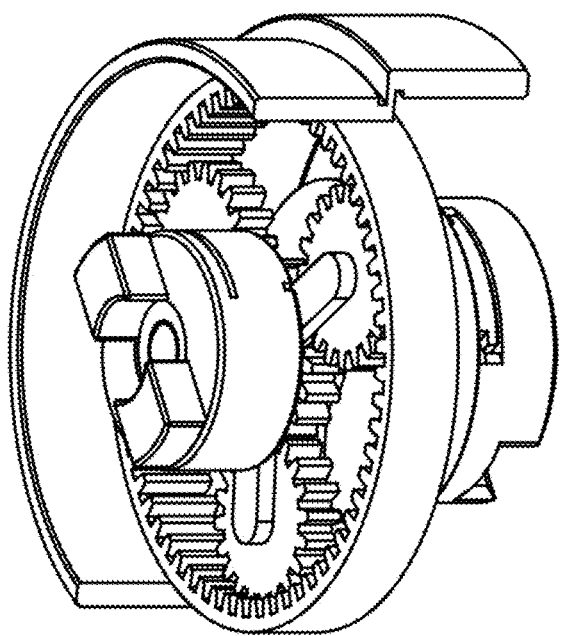

Another benefit of the present invention is that, like the fluidic cartridge, it includes features that compensate for axial misalignment that may occur in practical applications. We have designed a mechanical gearbox adapter, which operates on the principle of physical gear tooth meshing as shown in FIG. 7B, and we have also employed the magnetic gearbox in FIG. 7C, which relies on the flux-coupling dynamics between the magnets of the outer rotor, the ferromagnetic pole elements in the middle rotor, and the magnets of the inner rotor. As in other gearing systems, the input-to-output ratio may be adjusted by selecting appropriate gear or rotor circumferences within the gearbox. As a parallel with the mechanical system, the magnetic gear reduction adapter in FIG. 7C has an outer magnetic rotor, a rotating ferromagnetic pole element, and an inner magnetic rotor, all enclosed within a tubular housing. The selection of which of the three components is connected to coupling boss 1 and which is connected to coupling boss 2 will determine the relative direction and velocity of rotation of the two couplings, providing either a decrease in rotational speed accompanied by an increase in delivered torque, or an increase in rotational speed and decrease in available torque.

Continuous Perfusion Bioreactors

While the spiral microfluidic sorter[68-71] or alternating tangential flow or tangential flow filtration[72-75] could separate cells from extracellular media to allow separate analysis of the intracellular and extracellular proteomic and metabolomic profiles, the same technologies could also be used to return the cells to the bioreactor while allowing the conditioned media to exit the system, either for disposal or harvesting of secreted proteins and other cellular products. By including this separation, the chemostats would be converted to continuous perfusion bioreactors, wherein the cells were retained to increase in number and, if desired, continue to produce in quantity the targeted secreted proteins or other molecules. Hence, with the addition of the appropriate spiral, ATF, or TFF separation, the robot-scientist, self-driving CAPCAS platform could then be applied to entirely different classes of industrial problems, including the production of antibodies, enzymes, food protein, or other biomolecules.

The pumps and valves of this invention are ideally suited to operate a continuous perfusion bioreactor. In a batch-fed well plate, flask, or bioreactor that is seeded with a small number of dividing cells, the total number of cells that can be supported and the total amount of cell product that is produced are limited by the concentration of nutrients at the beginning of the batch and the maximum tolerable level of toxic nutrients that can be tolerated at the end of the batch. In a chemostat such as that in FIG. 1A, one of many possible microbial species will be able to replicate as long as there is an adequate supply of nutrients. The continuous inflow of nutrients would lead to a continuous increase in the number of cells in the bioreactor. If the volume of the chemostat is fixed, the continuous inflow must be accompanied by an equivalent continuous outflow. While the inflow would in theory not contain any cells, the outflow clearly would. If the flow rate into a chemostat is too fast, cells will be washed out before they have the time to divide, and eventually the chemostat will be flushed free from cells. Alternatively, the flow rate can be adjusted such that the number of cells washed out in each interval of time equals the number of new cells that are created by cellular division, and a steady state will be reached, hence the name "chemostat." The density of cells in the chemostat is determined by both the input nutrient concentration and flow rate.

In production reactors such as those that use CHO cells to produce antibodies, therapeutic proteins, or other large molecules, there may be economic reasons to increase the cell density within the reactor as high as possible and minimize the number of cells or high-value large molecules that are removed in the outflow. The conversion of a chemostat where cell loss is of no issue into a cell- and large-molecule-conserving perfusion bioreactor can be accomplished in several ways. With normal flow filtration (NFF), the media being removed from the bioreactors could be passed through a planar or hollow-fiber membrane filter to retain the cells and remove cell-free media. Unfortunately, filter fouling is a major drawback in NFF. With tangential flow filtering (TFF), a recirculating pump provides a continuous flow of cells and media across the surface of the filter membrane. A pressure difference across the membrane allows cell-free media to cross the membrane barrier, and the tangential flow minimized eliminates fouling. In alternating tangential flow (ATF), a diaphragm or other periodic push-pull pump alternates the direction of the flow across the membrane to eliminate membrane fouling. Alternatively, the radial Dean vortices in a spiral microfluidic channel can separate a mixed stream of cells and media into two streams, one enriched in cells and the other depleted. While normally implemented as a single large-scale spiral sorter[68], the CAPCAS could incorporate a separate spiral sorted on each of 48 wells.

Figure 8A:
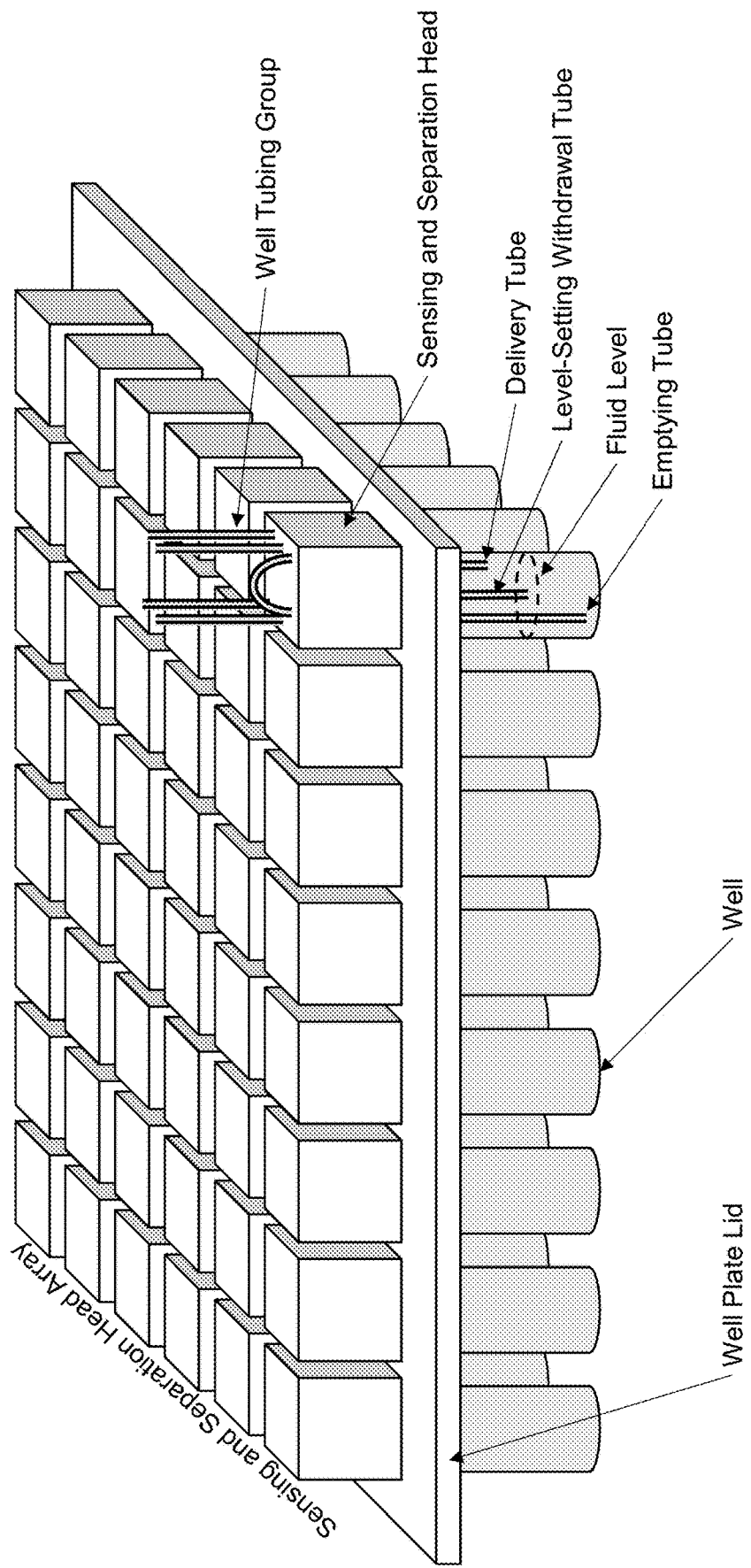
FIG. 8A show a multi-well, continuous perfusion bioreactor whose lid contains an array of sensing and separation heads which contain cell separators and media sensors, according to embodiments of the invention.

The microfluidic pumps and valves of this invention are ideally suited for this type of application, and the combination of pumps, valves, and filters can be implemented at a sufficiently small scale that it is possible to create a 48-well perfusion bioreactor on a single plate. FIGS. 8A-8E present a schematic representation of such a system. FIG. 8A show a multi-well, continuous perfusion bioreactor whose lid contains an array of sensing and separation heads which contain cell separators and media sensors. Calibration and input tubes, a recirculation tube, and waste and media output tubes comprise the well tubing group that would be connected to the pumps and valves in, for example, FIGS. 1F-1G. Each sensing and separation head contains a normal flow filter (NFF), a tangential flow filter (TFF), an alternating tangential flow filter (ATF), or a microfluidic spiral cell separator to remove suspended cells from the effluent and return these cells back to the bioreactor while removing cell-depleted media to maintain a constant volume in the bioreactor, as well as bubble and/or other sensors. Beneath the separation and sensing head are the three main tubes of the bioreactor: media/cell delivery, media/cell withdrawal, and a deep tube for removal of large volumes of cells and media. The array of sensing and separation heads can include a plurality of optical density (OD) measuring devices integrated into the continuous perfusion bioreactor.

Figure 8B:
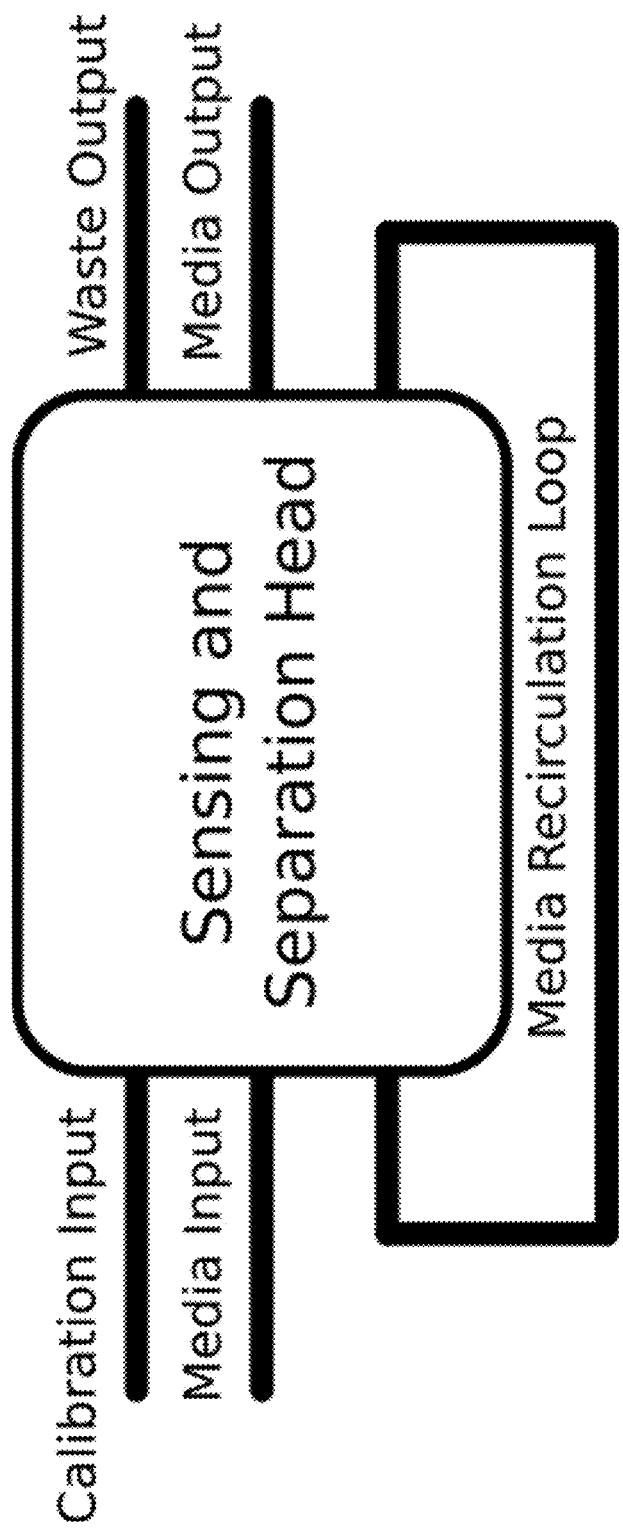
FIG. 8B shows a schematic representation of the sensing and separation head and the various tubes, according to embodiments of the invention.

FIG. 8B shows a schematic representation of the sensing and separation head and the various tubes that would be located above each bioreactor well. The pumps can either be internal or external to the head. The calibration and media input tubes, the recirculation loop, and the waste and media output tubes comprise the well tubing group in FIG. 8A.

Figure 8C:
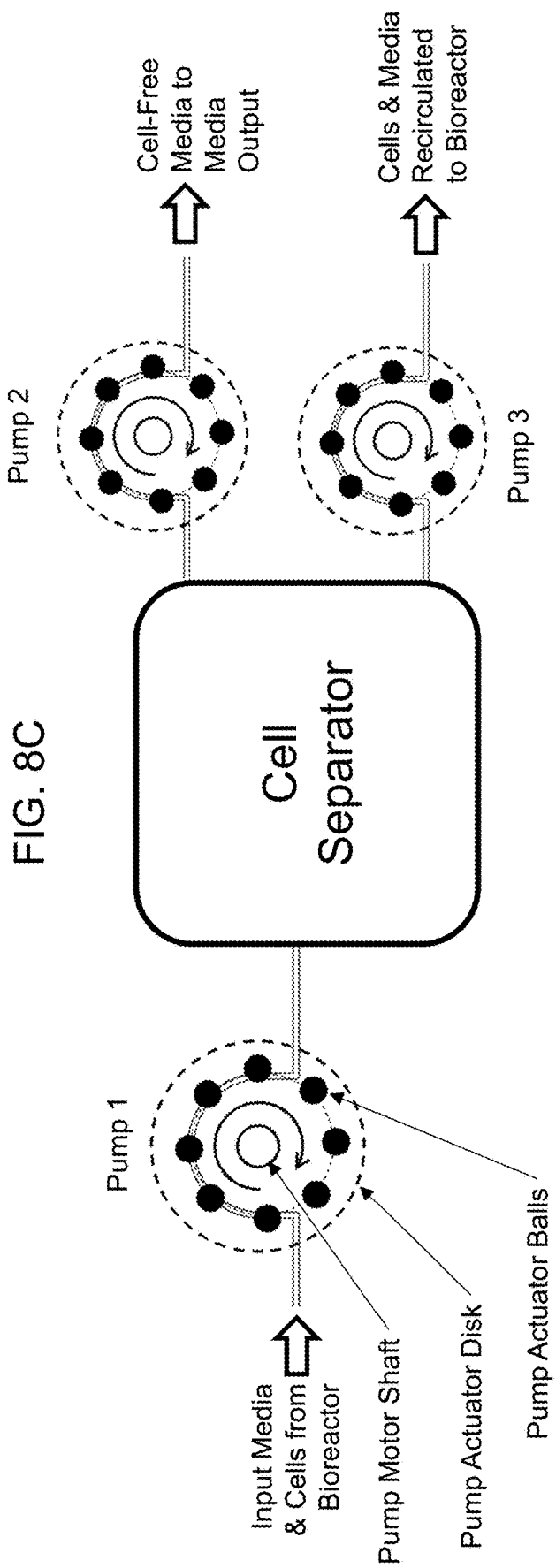
FIG. 8C shows how one input pump and two output pumps can control the cell separation and recycling process, according to embodiments of the invention.

FIG. 8C shows how one input pump and two output pumps can control the cell separation and recycling process. Valves (not shown) such as those in FIG. 2 could control the flow of media and/or media and cells to optical density, pH, or other sensors, where the short distance between the sensors and the fluid within the well would minimize the time required to move a sample from the well to its sensors.

Figure 8D:
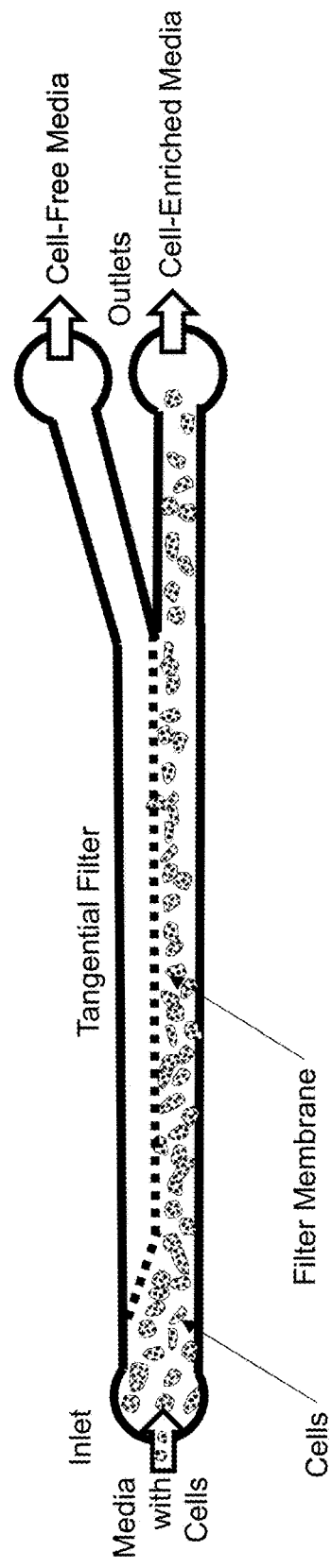
FIG. 8D provides a schematic representation of a tangential filter for separating cells from bulk media. The fouling of the filter membrane is prevented by periodic reversal of one or more pumps, according to embodiments of the invention.

FIG. 8D provides a schematic representation of a tangential filter for separating cells from bulk media. The fouling of the filter membrane is prevented by periodic reversal of one or more pumps. As discussed above, alternating tangential flow (ATF) or tangential flow filtration (TFF)[72-75] can be used for real-time separation of cells from media while minimizing filter fouling by cells, cell debris, and large molecules.

Figure 8E:
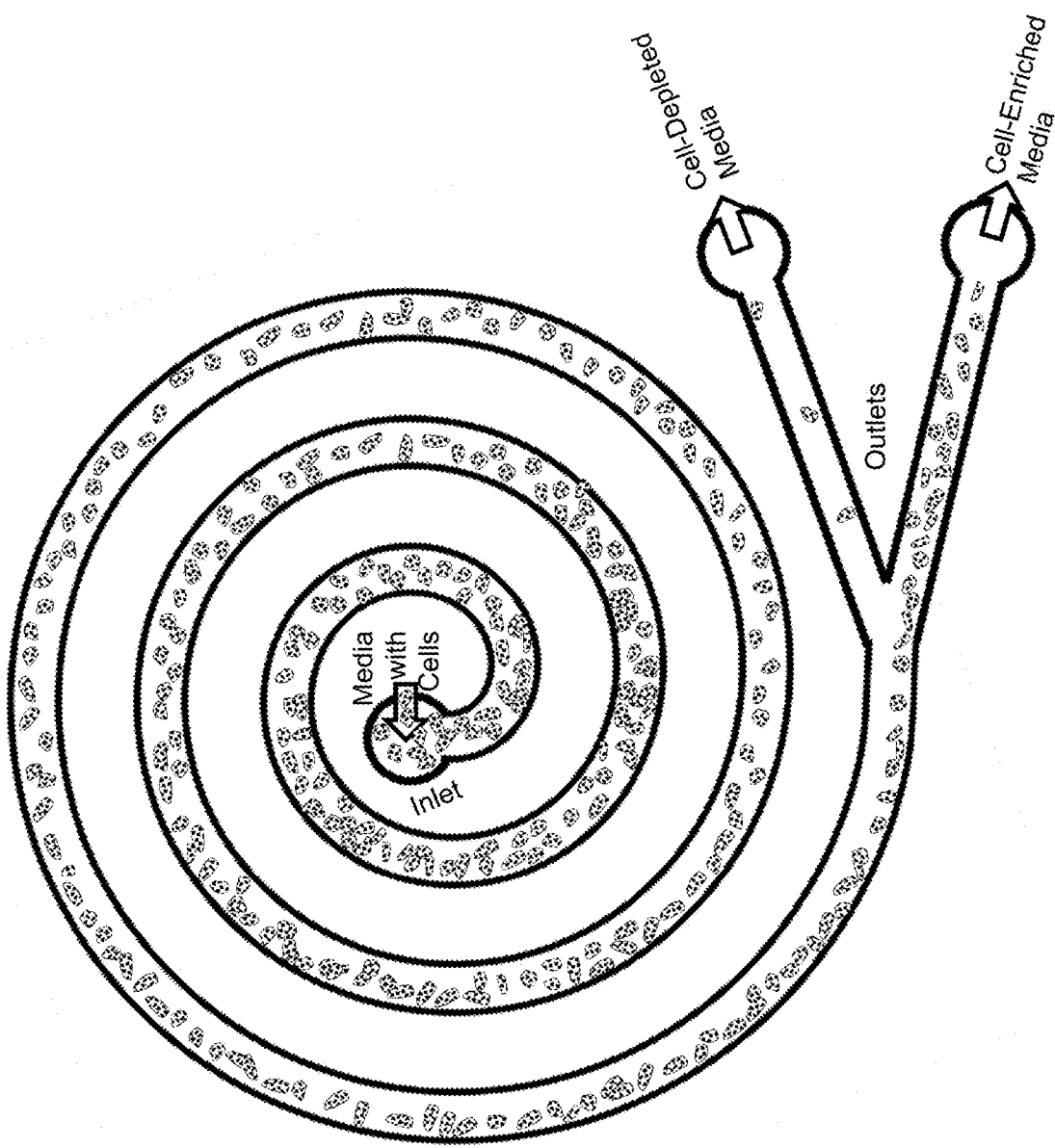
FIG. 8E shows a spiral inertial cell separator, also known as a spiral microfluidic sorter that could fit within each sensing and separation head, according to embodiments of the invention.

FIG. 8E shows a spiral inertial cell separator, also known as a spiral microfluidic sorter,[68-71] that could fit within each sensing and separation head.

Figure 9:
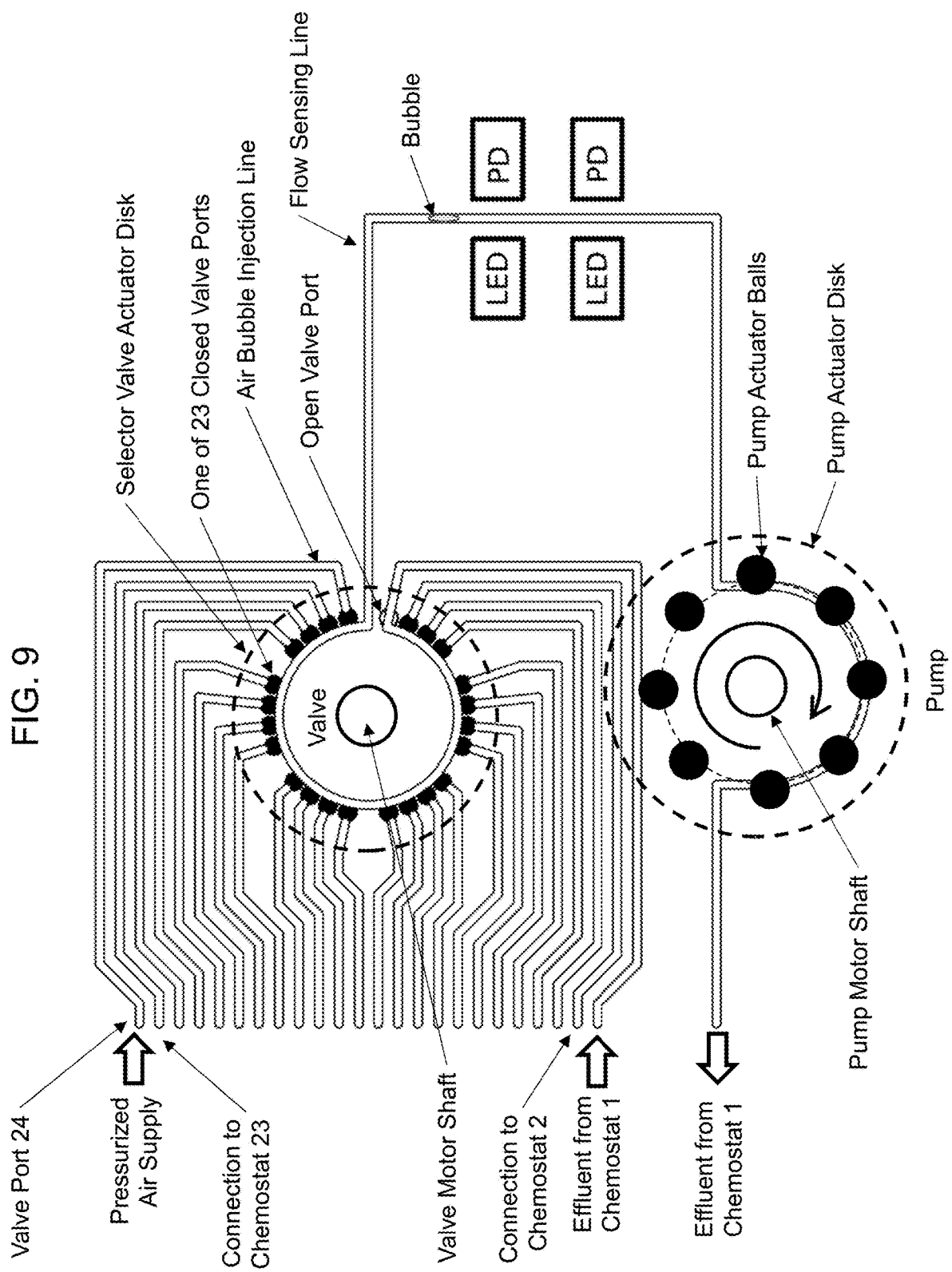
FIG. 9 illustrates how a pump and a valve operating in a coordinated manner can inject a bubble into a fluid carrying tube so that two spatially separated pairs of a light-emitting diode (LED) and a photodiode (PD) could detect the passage of the bubble and hence the flow velocity, according to embodiments of the invention.

FIG. 9 illustrates how a pump and a valve operating in a coordinated manner can inject a bubble into a fluid carrying tube so that two spatially separated pairs of a light-emitting diode (LED) and a photodiode (PD) could detect the passage of the bubble and hence the flow velocity. The array of sensing and separation heads in FIGS. 8A-8E can provide a plurality of bubble tracking flow meters integrated into the multi-well chemostat/bioreactor. The principle of one of these flowmeters is shown in FIG. 9, where the position of a selector valve actuator determines the chemostat from which effluent will be drawn. A transient rotation of the valve actuator to open valve port 24 will lead to the injection of a small bubble into the flow-sensing line, and the clockwise rotation of the rotary planar peristaltic pump will cause that bubble to move towards the first and then the second light-emitting diode (LED) and photodiode (PD) pair, whose two outputs will change with the passage of the bubble. The time interval between the two signals and the distance between the two LED/PD pairs can be used to calculate flow velocity imposed by the pump. Flows from other chemostats could be measured by rotating the valve actuator to open other ports. In some embodiments, the valve used could be the cut-in valve in FIG. 2L-2M so that the effluent of all chemostats can flow except for the one selected for measurement. Alternatively, a bubble flow meter could be located in one of the three analyzer positions shown in FIG. 1I to measure the flow rate, and hence volume, withdrawn from a single fluidic module. The other analyzer positions on this valve could be connected to other on-line instruments that measure optical density, pH, and mass spectrometry and other analytical quantities. The use of a single LED-photodiode pair could also detect bubbles as process control and to detect one or more bubbles injected to demark the boundary between two samples.

System Control Software

The CAPCAS hardware embodiments described in FIGS. 1D-1I present the means by which multiple chemostats, bioreactors, well plates, organ chips, and other bio-objects can be continuously perfused and analyzed. In order to create a robot scientist that can function as a self-driving biological laboratory, each of the pumps and valves must operate under carefully timed computer control that is informed by a variety of sensors that are distributed throughout the system. In contrast to open-loop systems without feedback control of pH or other biological variables that might operate with a simple set of serial instructions, many of the CAPCAS operations must be carefully coordinated; for example, only when a bioreactor becomes acidic should a pair of valves be switched, or when the optical density becomes too high, a pump speed should be increased, a pump should be turned off when a bubble is detected but the valve should not be switched to another pump if either pump is still running. Furthermore, the control must interface bidirectionally with the artificial intelligence/machine-learning (AI/ML) software that designs the experiments and analyzes the resulting data, termed CAPCAS-AI. However, such conditional logic and bidirectional communication is not supported in the Automated MultiPump Experiment Running Environment (AMPERE) that has previously been used to control our microfluidic pumps and valves, for example in our MultiWell MicroFormulator.

Addressing the need for conditional logic for distributed control of CAPCAS and the bidirectional interface to CAPCAS-AI requires a dedicated software system, termed CAPCAS-IT, which is a software application that enables control over hardware through its own protocol-building capabilities or remotely through a structured query language (SQL) database, termed CAPCAS-DB. CAPCAS-IT communicates with connected hardware to perform operations to run an experiment and receive feedback on hardware functions and measurements. CAPCAS-IT can also read and write settings and experimental data to CAPCAS-DB. This can occur periodically during the running of an experiment. This allows CAPCAS-IT to keep up to date when changes are made to CAPCAS-DB. Details of this software system are provided in U.S. Pat. No. 11,447,734 B2.

Alternative Embodiments

While the scale of the systems presented herein focuses on pumps and valves designed for operation with well plates, organ chips, or other similarly sized bio-objects, the topology and operation of such a CAPCAS unit can be scaled to larger or smaller fluidic volumes. The addition of fluidic buses could be used to reduce the size of each unit, or increase the speed with which media was formulated. The sizes of the enclosures described are set by laboratory convention and respect the height and width of doorways, but larger or smaller enclosures would be possible. Coupled organs could be implemented by the use of a bidirectional microformulator, or by means of connections hard-plumbed into the lid or a fluidic bus. An important feature of the pump, valve, and other hardware design of the CAPCAS approach is that a large number of chemostat or bioreactor plates can be operated over long periods of time without being disturbed by creating a fluid handling system that can perfuse the chemostats or bioreactors without interruption, something that is not possible in conventional high-throughput screening systems where a fluid handler outside the incubator is needed to refresh the media of wells that would otherwise be held in an incubator. Other robot designs could deliver well plates to fluidic stations, or compact fluidic stations could be delivered to fixed plates.

In summary, the CAPCAS platform pump and valve cartridges that are the subject of this invention and the system embodiments described offer an alternative to large, room-sized high-throughput screening systems that rely on daily media changes and transport of plates or organ chips between incubator, fluid handler, and plate reader. However, CAPCAS would be compatible with and interfaceable to existing well-plate robotics. It would be ideal for any experiment that requires continuous or controlled perfusion, particularly over the long term. It would be useful for any bioreactor or culture system that could fit in a well-plate footprint, and would be particularly well suited for long-growth-time models that would require frequent feeding or media adjustments. The fluidic control and delivery systems are supported in a station above the working deck and can replace rocker systems for gravity perfusion. The CAPCAS chassis in FIG. 4A would not require an incubator and could be small enough that a single-chemostat-plate unit could sit on a laboratory bench or within a cell culture hood, or it could be a large free-standing unit that operated a thousand or more independent chemostats. The use of multiple iPlate-Bots would enable parallel, asynchronous delivery and removal of well plates from multiple CAPCAS fluidic control stations. The robot scientist software that drives CAPCAS can design and execute complex experiments and generate and test hypotheses in a manner that is vastly more efficient than what humans alone can achieve.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

Some references, which may include patents, patent applications, and various publications, are cited and discussed in the description of the invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference.

LIST OF REFERENCES

1. Watson, D E, Hunziker, R, and Wikswo, J P. Fitting tissue chips and microphysiological systems into the grand scheme of medicine, biology, pharmacology, and toxicology. Exp. Biol. Med., 242:1559-1572. 2017. PMCID: PMC5661772.
2. ASTM. Standard F3570-22, Standard Terminology Relating to Microphysiological Systems. In: Book of Standards Volume: 13.02, Developed by Subcommittee: F04.43. 2022.
3. LeDuc, P R, Messner, W C, and Wikswo, J P. How do control-based approaches enter into biology? Annu. Rev. Biomed. Eng., 13:369-396. 2011.
4. King, R D, Whelan, K E, Jones, F M, Reiser, P G K, Bryant, C H, Muggleton, S H, Kell, D B, and Oliver, S G. Functional genomic hypothesis generation and experimentation by a robot scientist. Nature, 427:247-252. 2004.
5. King, R D, Rowland, J, Oliver, S G, Young, M, Aubrey, W, Byrne, E, Liakata, M, Markham, M, Pir, P, Soldatova, L N, Sparkes, A, Whelan, K E, and Clare, A. The automation of science. Science, 324:85-89. 2009.
6. King, R D, Rowland, J, Aubrey, W, Liakata, M, Markham, M, Soldatova, L N, Whelan, K E, Clare, A, Young, M, Sparkes, A, Oliver, S G, and Pir, P. The Robot Scientist Adam. Comp, 42:46-54. 2009.
7. Williams, K, Bilsland, E, Sparkes, A, Aubrey, W, Young, M, Soldatova, L N, De Grave, K, Ramon, J, de Clare, M, Sirawaraporn, W, Oliver, S G, and King, R D. Cheaper faster drug development validated by the repositioning of drugs against neglected tropical diseases. J. R. Soc. Interface, 12: 20141289. 2015.
8. Coutant, A, Roper, K, Trejo-Banos, D, Bouthinon, D, Carpenter, M, Grzebyta, J, Santini, G, Soldano, H, Elati, M, Ramon, J, Rouveirol, C, Soldatova, L N, and King, R D. Closed-loop cycles of experiment design, execution, and learning accelerate systems biology model development in yeast. Proc. Natl. Acad. Sci. U.S.A., 116:18142-18147. 2019.
9. Kadouri, A, and Spier, R E. Some myths and messages concerning the batch and continuous culture of animal cells. Cytotechnology, 24:89-98. 1997.
10. Hoskisson, P A, and Hobbs, G. Continuous culture—making a comeback? Microbiol.-SGM, 151:3153-3159. 2005.
11. Ziv, N, Brandt, N J, and Gresham, D. The Use of Chemostats in Microbial Systems Biology. J. Vis. Exp., 80: e50168. 2013.
12. Croughan, M S, Konstantinov, K B, and Cooney, C. The Future of Industrial Bioprocessing: Batch or Continuous? Biotechnol. Bioeng., 112:648-651. 2015.
13. Bielser, J M, Wolf, M, Souquet, J, Broly, H, and Morbidelli, M. Perfusion mammalian cell culture for recombinant protein manufacturing—A critical review. Biotechnol. Adv., 36:1328-1340. 2018.

14. Karst, D J, Steinebach, F, and Morbidelli, M. Continuous integrated manufacturing of therapeutic proteins. Curr. Opin. Biotechnol., 53:76-84. 2018.
15. Monod, J. La technique de culture continue théorie et applications. Ann. Inst. Pasteur (Paris), 79:390-410. 1950.
16. Novick, A, and Szilard, L. Description of the Chemostat. Science, 112:715-716. 1950.
17. Novick, A, and Szilard, L. Experiments with the Chemostat on Spontaneous Mutations of Bacteria. Proc. Natl. Acad. Sci., 36:708-719. 1950.
18. "Integrated Organ-on-Chip Systems and Applications of the Same," Wikswo, J P, Cliffel, D E, Markov, D A, McLean, J A, McCawley, L J, Samson, P C, Reiserer, R S, Block, F E, and McKenzie, J R, U.S. Pat. No. 10,444,223 B2 (Oct. 15, 2019)
19. "Integrated human organ-on-chip microphysiological systems," Wikswo, J P, Samson, P C, Block III, F E, Reiserer, R S, Parker, K K, McLean, J A, McCawley, L J, Markov, D, Levner, D, Ingber, D E, Hamilton, G A, Goss, J A, Cunningham, R, Cliffel, D E, McKenzie, J R, Bahinski, A, and Hinojosa, C D, U.S. Pat. No. 9,725,687 B2 (Aug. 8, 2017)
20. Miller, D R, Schaffer, D K, Neely, M D, McClain, E S, Travis, A R, Block III, F E, McKenzie, J R, Werner, E M, Armstrong, L, Markov, D A, Bowman, A B, Ess, K C, Cliffel, D E, and Wikswo, J P. A bistable, multiport valve enables microformulators creating microclinical analyzers that reveal aberrant glutamate metabolism in astrocytes derived from a tuberous sclerosis patient. Sens. Actuators B Chem., 341: 129972. 2021.
21. Eklund, S E, Snider, R M, Wikswo, J, Baudenbacher, F, Prokop, A, and Cliffel, D E. Multianalyte microphysiometry as a tool in metabolomics and systems biology. J. Electroanal. Chem., 587:333-339. 2006.
22. Snider, R M, McKenzie, J R, Kraft, L, Kozlov, E, Wikswo, J P, and Cliffel, D E. The effects of Cholera Toxin on cellular energy metabolism. Toxins (Basel), 2:632-648. 2010. PMCID: PMC3153216.
23. Lima, E A, Snider, R M, Reiserer, R S, McKenzie, J R, Kimmel, D W, Eklund, S E, Wikswo, J P, and Cliffel, D E. Multichamber multipotentiostat system for cellular microphysiometry. Sensors Actuators B: Chem., 204:536-543. 2014. PMCID: PMC4167374.
24. McKenzie, J R, Cliffel, D E, and Wikswo, J P. Electrochemical monitoring of cellular metabolism. In: Encyclopedia of Applied Electrochemistry. R. Savinell, K. Ota and G. Kreysa, eds. Springer Science+Business Media, New York. pp 522-528. 2014.
25. McKenzie, J R, Cognata, A C, Davis, A N, Wikswo, J P, and Cliffel, D E. Real-Time Monitoring of Cellular Bioenergetics with a Multianalyte Screen-Printed Electrode. Anal. Chem., 87:7857-7864. 2015. PMCID: PMC4770793.
26. "Device and Methods for Detecting the Response of a Plurality of Cells to at Least one Analyte of Interest," Cliffel, D, Baudenbacher, F J, Wikswo, J P, Eklund, S, Balcarcel, R R, and Gilligan, J M, U.S. Pat. No. 7,713,733 B2 (May 11, 2010)
27. "Apparatus and methods for monitoring the status of a metabolically active cell," Baudenbacher, F J, Wikswo, J P, Balcarcel, R R, Cliffel, D, Eklund, S, Gilligan, J M, McGuinness, O, Monroe, T, Prokop, A, Stremler, M A, and Werdich, A A, U.S. Pat. No. 7,704,745 B2 (Apr. 27, 2010)
28. "Cartridge systems, capacitive pumps and multi-throw valves and pump-valve systems and applications of same," Schaffer, D K, Markov, D A, Reiserer, R S, McCawley, L J, Geuy, M, Britt, C M, and Wikswo, J P, U.S. Pat. No. 11,135,582 B2 (Oct. 5, 2021)
29. "Cartridge systems, capacitive pumps and multi-throw valves and pump-valve systems and applications of the same," Schaffer, D K, Markov, D A, Reiserer, R S, McCawley, L, Geuy, M, Britt, C M, and Wikswo, J P, U.S. Pat. No. 11,465,144 B2 (12 Oct. 2022)
30. "Microfluidic systems for multiple bioreactors and applications of same," Wikswo, J P, Schaffer, D K, Reiserer, R S, and Geuy, M D, Application PCT/US21/42141 (Jul. 19, 2021)
31. "Peristaltic micropump and related systems and methods," Gould, P A, Hoang, L T, Schaffer, D K, Reiserer, R S, Samson, P C, and Wikswo, J P, U.S. Pat. No. 10,781,809 B2 (Sep. 22, 2020)
32. "Peristaltic micropump and related systems and methods," Gould, P A, Hoang, L T, Scherrer, J R, Matloff, W J, Seale, K T, Curtis, E L, Schaffer, D K, Hall, D J, Kole, A, Reiserer, R S, Tidwell, H, Samson, P C, and Wikswo, J P, U.S. Pat. No. 10,487,819 B2 (Nov. 26, 2019)
33. "Organ on chip integration and applications of the same," Block III, F E, Samson, P C, Werner, E M, Markov, D A, Reiserer, R S, McKenzie, J R, Cliffel, D E, Matloff, W J, Block Jr, F E, Scherrer, J R, Tidwell, W H, and Wikswo, J P, U.S. Pat. No. 9,874,285 B2 (Jan. 23, 2018)
34. "Microfluidic systems, pumps, valves, fluidic chips thereof, and applications of same," Reiserer, R S, Schaffer, D K, Samson, P C, Markov, D A, Geuy, M D, McCawley, L J, and Wikswo, J P, PCT Patent Application PCT/US20/40061 (Jun. 29, 2020)
35. "Multichannel Pumps and Applications of Same," Wikswo, J P, Reiserer, R S, Schaffer, D K, Markov, D A, and Britt, C M, PCT Patent Application PCT/US19/47190 Published as WO2020/041260 A1 (Feb. 27, 2020)
36. "Normally closed microvalve and applications of the same," Block III, F E, Samson, P C, and Wikswo, J P, U.S. Pat. No. 9,618,129 B2 (Apr. 11, 2017)
37. "Microbioreactor with vertical-via rotary metering valves and applications of same," Schaffer, D K, Wikswo, J P, Reiserer, R S, Geuy, M D, Spivey, E C, Britt, C M, Brown, J A, Markov, D A, Faley, S, McCawley, L J, and Samson, P C, U.S. Provisional Patent Application 63/017,744 (Apr. 30, 2020)
38. "Microfluidic systems for multiple bioreactors and applications of same," Wikswo, J P, Reiserer, R S, and Schaffer, D K, PCT Patent Application 63/053,388 (Jul. 17, 2020)
39. "Pressure regulation system, pressure release valves thereof, passive pressurized fluid reservoirs, and applications of same," Samson, P C, Schaffer, D K, Reiserer, R S, Schatzki, L, Markov, D A, Britt, C M, and Wikswo, J P, PCT Patent Application PCT/US19/47324 Published as WO2020/041357 A2 (Feb. 27, 2020)
40. "Multicompartment microfluidic bioreactors, cylindrical rotary valves and applications of same," Wikswo, J P, Spivey, E C, Schaffer, D K, Reiserer, R S, Seale, K T, and Block, F E, PCT Patent Application PCT/US2019/034285 Published as WO2019/231977 A1 (Dec. 5, 2019)
41. "Interconnections of multiple perfused engineered tissue constructs and microbioreactors, multi-microformulators and applications of the same," Wikswo, J P, Markov, D A, Samson, P C, Block III, F E, Schaffer, D K, and Reiserer, R S, European Patent Application published as EP3415611 (Dec. 19, 2018)
42. "Interconnections of multiple perfused engineered tissue constructs and microbioreactors, multi-microformulators and applications of the same," Wikswo, J P, Markov, D A, Samson, P C, Block III, F E, Schaffer, D K, and Reiserer, R S, European Patent Application published as EP3190172 A3 (Aug. 30, 2017)
43. Cyr, K J, Avaldi, O M, and Wikswo, J P. Circadian hormone control in a human-on-a-chip: In vitro biology's ignored component? Exp. Biol. Med., 242:1714-1731. 2017. PMCID: PMC5832251.
44. "Interconnections of multiple perfused engineered tissue constructs and microbioreactors, multi-microformulators and applications of the same," Wikswo, J P, Block III, F E, and Samson, P C, U.S. Pat. No. 10,577,574 B2 (Mar. 3, 2020)
45. "System and method for microdialysis imaging and regional fluidic delivery and control and applications of same," Wikswo, J P, Reiserer, R S, and Hawkins, K, U.S. Pat. No. 10,538,726 B2 (Jan. 21, 2020)
46. "Interconnections of multiple perfused engineered tissue constructs and microbioreactors, multi-microformulators and applications of the same," Wikswo, J P, Markov, D A, Samson, P C, Block III, F E, Schaffer, D K, and Reiserer, R S, U.S. Pat. No. 10,023,832 B2 Published as China Patent ZL201710014601.1 (Jul. 17, 2018)
47. "System and method for microdialysis imaging and regional fluidic delivery and control and applications of same," Wikswo, J P, Hawkins, K G, and Reiserer, R S, National Phase patent application Ser. No. 16/397,019 (Apr. 29, 2019)
48. Unger, M A, Chou, H P, Thorsen, T, Scherer, A, and Quake, S R. Monolithic microfabricated valves and pumps by multilayer soft lithography. Science, 288:113-116. 2000.
49. Thorsen, T, Maerkl, S J, and Quake, S R. Microfluidic Large-Scale Integration. Science, 298:580-584. 2002.
50. Enders, J R, Marasco, C C, Wikswo, J P, and McLean, J A. A Dual-Column Solid Phase Extraction Strategy for Online Collection and Preparation of Continuously Flowing Effluent Streams for Mass Spectrometry. Anal. Chem., 84:8467-8474. 2012. PMCID: PMC3518407.
51. Marasco, C C, Goodwin, C R, Winder, D G, Schramm-Sapyta, N L, McLean, J A, and Wikswo, J P. Systems-level view of cocaine addiction: The interconnection of the immune and nervous systems. Exp. Biol. Med., 239: 1433-1442. 2014. PMCID: PMC4216763.
52. Zhang, X, Romm, M, Zheng, X Y, Zink, E M, Kim, Y M, Burnum-Johnson, K E, Orton, D J, Apffel, A, Ibrahim, Y M, Monroe, M E, Moore, R J, Smith, J N, Ma, J, Renslow, R S, Thomas, D G, Blackwell, A E, Swinford, G, Sausen, J, Kurulugama, R T, Eno, N, Darland, E, Stafford, G, Fjeldsted, J, Metz, T O, Teeguarden, J G, Smith, R D, and Baker, E S. SPE-IMS-MS: An automated platform for sub-sixty second surveillance of endogenous metabolites and xenobiotics in biofluids. Clin. Mass Spectrom., 2:1-10. 2016.
53. May, J C, Dodds, J N, Kurulugama, R T, Stafford, G C, Fjeldsted, J C, and McLean, J A. Broadscale resolving power performance of a high precision uniform field ion mobility-mass spectrometer. Analyst, 140:6824-6833. 2015. PMCID: PMC4586486.
54. May, J C, Goodwin, C R, Lareau, N M, Leaptrot, K L, Morris, C B, Kurulugama, R T, Mordehai, A, Klein, C, Barry, W, Darland, E, Overney, G, Imatani, K, Stafford, G C, Fjeldsted, J C, and McLean, J A. Conformational Ordering of Biomolecules in the Gas Phase: Nitrogen Collision Cross Sections Measured on a Prototype High Resolution Drift Tube Ion Mobility-Mass Spectrometer. Anal. Chem., 86:2107-2116. 2014. PMCID: PMC3931330.
55. Kim, H S, Waqued, S C, Nodurft, D T, Devarenne, T P, Yakovlev, V V, and Han, A. Raman spectroscopy compatible PDMS droplet microfluidic culture and analysis platform towards on-chip lipidomics. Analyst, 142:1054-1060. 2017.
56. Jahn, I J, Zukovskaja, O, Zheng, X S, Weber, K, Bocklitz, T W, Cialla-May, D, and Popp, J. Surface-enhanced Raman spectroscopy and microfluidic platforms: challenges, solutions and potential applications. Analyst, 142:1022-1047. 2017.
57. Abu-Absi, N R, Kenty, B M, Cuellar, M E, Borys, M C, Sakhamuri, S, Strachan, D J, Hausladen, M C, and Li, Z J. Real Time Monitoring of Multiple Parameters in Mammalian Cell Culture Bioreactors Using an In-Line Raman Spectroscopy Probe. Biotechnol. Bioeng., 108:1215-1221. 2011.
58. Whelan, J, Craven, S, and Glennon, B. In situ Raman spectroscopy for simultaneous monitoring of multiple process parameters in mammalian cell culture bioreactors. Biotechnol. Prog., 28:1355-1362. 2012.
59. Rafferty, C, O'Mahony, J, Burgoyne, B, Rea, R, Balss, K M, and Latshaw, D C. Raman spectroscopy as a method to replace off-line pH during mammalian cell culture processes. Biotechnol. Bioeng., 117:146-156. 2020.
60. Iversen, J A, Berg, R W, and Ahring, B K. Quantitative monitoring of yeast fermentation using Raman spectroscopy. Anal. Bioanal. Chem., 406:4911-4919. 2014.
61. Markov, D A, Lillie, E M, Garbett, S P, and McCawley, L J. Variation in diffusion of gases through PDMS due to plasma surface treatment and storage conditions. Biomed. Microdevices, 16:91-96. 2014. PMCID: PMC3945670.
62. Eklund, S E, Cliffel, D E, Kozlov, E, Prokop, A, Wikswo, J P, Jr., and Baudenbacher, F J. Modification of the Cytosensor™ Microphysiometer to Simultaneously Measure Extracellular Acidification and Oxygen Consumption Rates. Anal. Chim. Acta, 496:93-101. 2003.
63. Velkovsky, M, Cliffel, D, Eklund, S, Eluvathingal, S, Stremler, M A, and Wikswo, J P. Extracting Metabolic Fluxes from Measurements with a Multianalyte Micro-Physiometer. Biophysical Society 49th Annual Meeting, Long Beach, Calif., 2005,
64. Eklund, S E, Thompson, R G, Snider, R M, Carney, C K, Wright, D W, Wikswo, J, and Cliffel, D E. Metabolic discrimination of select list agents by monitoring cellular responses in a multianalyte microphysiometer. Sensors, 9:2117-2133. 2009. PMCID: PMC3345856.
65. Velkovsky, M, Snider, R, Cliffel, D E, and Wikswo, J P. Modeling the measurements of cellular fluxes in microbioreactor devices using thin enzyme electrodes. J. Math. Chem., 49:251-275. 2011. PMCID: PMC3768171.
66. "Integrated organ-on-chip systems and applications of the same," Wikswo, J P, Cliffel, D E, Markov, D A, McLean, J A, McCawley, L J, Samson, P C, Reiserer, R S, Block, F E, and McKenzie, J R, U.S. Pat. No. 10,078, 075 B2 (Sep. 18, 2018)
67. Byrd, T F, Hoang, L T, Kim, E G, Pfister, M E, Werner, E M, Arndt, S E, Chamberlain, J W, Hughey, J J, Nguyen, B A, Schneibel, E J, Wertz, L L, Whitfield, J S, Wikswo, J P, and Seale, K T. The microfluidic multitrap nanophysiometer for hematologic cancer cell characterization reveals temporal sensitivity of the calcein-AM efflux assay. Sci. Rep., 4: 5117. 2014. PMCID: PMC4038811.
68. Kwon, T, Prentice, H, De Oliveira, J, Madziva, N, Warkiani, M E, Hamel, J F P, and Han, J. Microfluidic Cell Retention Device for Perfusion of Mammalian Suspension Culture. Sci. Rep., 7: 6703. 2017.
69. Sonmez, U, Jaber, S, and Trabzon, L. Super-enhanced particle focusing in a novel microchannel geometry using inertial microfluidics. J. Micromech. Microeng., 27: 065003. 2017.
70. Warkiani, M E, Tay, A K P, Guan, G F, and Han, J. Membrane-less microfiltration using inertial microfluidics. Sci. Rep., 5: 11018. 2015.
71. Warkiani, M E, Guan, G F, Luan, K B, Lee, W C, Bhagat, A A S, Chaudhuri, P K, Tan, D S W, Lim, W T, Lee, S C, Chen, P C Y, Lim, C T, and Han, J. Slanted spiral microfluidics for the ultra-fast, label-free isolation of circulating tumor cells. Lab Chip, 14:128-137. 2014.
72. Bosco, B, Paillet, C, Amadeo, I, Mauro, L, Orti, E, and Forno, G. Alternating Flow Filtration as an Alternative to Internal Spin Filter Based Perfusion Process: Impact on Productivity and Product Quality. Biotechnol. Prog., 33:1010-1014. 2017.
73. Clincke, M-F, Mölleryd, C, Zhang, Y, Lindskog, E, Walsh, K, and Chotteau, V. Study of a recombinant CHO cell line producing a monoclonal antibody by ATF or TFF external filter perfusion in a WAVE Bioreactor™. BMC Proc., 5: P105. 2011.
74. Karst, D J, Serra, E, Villiger, T K, Soos, M, and Morbidelli, M. Characterization and comparison of ATF and TFF in stirred bioreactors for continuous mammalian cell culture processes. Biochem. Eng. J., 110:17-26. 2016.
75. Wang, S, Godfrey, S, Ravikrishnan, J, Lin, H, Vogel, J, and Coffman, J. Shear contributions to cell culture performance and product recovery in ATF and TFF perfusion systems. J. Biotechnol., 246:52-60. 2017.
76. Gorkov, L P. On the Forces Acting on a Small Particle in an Acoustic Field Within an Ideal Fluid. Dokl. Phys., 6:773-775. 1962.
77. Goddard, G, Martin, J C, Graves, S W, and Kaduchak, G. Ultrasonic particle-concentration for sheathless focusing of particles for analysis in a flow cytometer. Cytometry Part A, 69A:66-74. 2006.
78. Gencturk, E, Ulgen, K O, and Mutlu, S. Thermoplastic microfluidic bioreactors with integrated electrodes to study tumor treating fields on yeast cells. Biomicrofluidics, 14: 034104. 2020.
79. Marasco, C C, Enders, J R, Seale, K T, McLean, J A, and Wikswo, J P. Real-time Cellular Exometabolome Analysis with a Microfluidic-mass Spectrometry Platform. PLoS One, 10: e0117685. 2015. PMCID: PMC4344306.
80. Brown, J A, Pensabene, V, Markov, D A, Allwardt, V, Neely, M D, Shi, M, Britt, C M, Hoilett, O S, Yang, Q, Brewer, B M, Samson, P C, McCawley, L J M, James M., Webb, D J, Li, D, Bowman, A B, Reiserer, R S, and Wikswo, J P. Recreating blood-brain barrier physiology and structure on chip: A novel neurovascular microfluidic bioreactor. Biomicrofluidics, 9: 054124. 2015. PMCID: PMC4627929.
81. Brown, J A, Codreanu, S G, Shi, M, Sherrod, S D, Markov, D A, Neely, M D, Britt, C M, Hoilett, O S, Reiserer, R S, Samson, P C, McCawley, L J, Webb, D J, Bowman, A B, McLean, J A, and Wikswo, J P. Metabolic consequences of inflammatory disruption of the blood-brain barrier in an organ-on-chip model of the human neurovascular unit. J. Neuroinflammation, 13: 306. 2016. PMCID: PMC5153753.
82. Brown, J A, Faley, S L, Shi, Y, Hillgren, K M, Sawada, G A, Baker, T K, Wikswo, J P, and Lippmann, E S. Advances in blood-brain barrier modeling in microphysiological systems highlight critical differences in opioid transport due to cortisol exposure. Fluids Barriers CNS, 17: 38. 2020. PMCID: PMC7269003.
83. May, J C, and McLean, J A. Advanced Multidimensional Separations in Mass Spectrometry: Navigating the Big Data Deluge. Annu. Rev. Anal. Chem., 9:387-409. 2016.
84. Enders, J R, Marasco, C C, Kole, A, Nguyen, B, Sundarapandian, S, Seale, K T, Wikswo, J P, and McLean, J A. Towards monitoring real-time cellular response using an integrated microfluidics-MALDINESI-ion mobility-mass spectrometry platform. IET Syst. Biol., 4:416-427. 2010. PMCID: PMC4254925.
85. Gutierrez, D B, Gant-Branum, R L, Romer, C E, Farrow, M A, Allen, J L, Dahal, N, Nei, Y W, Codreanu, S G, Jordan, A T, Palmer, L D, Sherrod, S D, McLean, J A, Skaar, E P, Norris, J L, and Caprioli, R M. An Integrated, High-Throughput Strategy for Multiomic Systems Level Analysis. J. Proteome Res., 17:3396-3408. 2018.
86. Rafferty, C, Johnson, K, O'Mahony, J, Burgoyne, B, Rea, R, and Balss, K M. Analysis of chemometric models applied to Raman spectroscopy for monitoring key metabolites of cell culture. Biotechnol. Prog., 36: e2977. 2020.
87. Short, K W, Carpenter, S, Freyer, J P, and Mourant, J R. Raman spectroscopy detects biochemical changes due to proliferation in mammalian cell cultures. Biophys. J., 88:4274-4288. 2005.
88. Ali, A, Abouleila, Y, and Germond, A. An Integrated Raman Spectroscopy and Mass Spectrometry Platform to Study Single-Cell Drug Uptake, Metabolism, and Effects. J. Vis. Exp.: e60449. 2020.
89. Wolff, A, Perch-Nielsen, I R, Larsen, U D, Friis, P, Goranovic, G, Poulsen, C R, Kutter, J P, and Telleman, P. Integrating advanced functionality in a microfabricated high-throughput fluorescent-activated cell sorter. Lab Chip, 3:22-27. 2003.
90. Hui, W C, Yobas, L, Samper, V D, Heng, C K, Liw, S, Ji, H, Chen, Y, Cong, L, Li, J, and Lim, T M. Microfluidic systems for extracting nucleic acids for DNA and RNA analysis. Sensors and Actuators A, 133:335-339. 2007.
91. Gao, J, Yin, X F, and Fang, Z L. Integration of single cell injection, cell lysis, separation and detection of intracellular constituents on a microfluidic chip. Lab Chip, 4:47-52. 2004.

What is claimed is:

1. A fluidic cartridge, comprising:
a fluidic disk having a plurality of alignment openings;
a fluidic chip comprising a body having a first surface and an opposite, second surface, one or more channels formed in the body in fluidic communications with input ports and output ports for transferring one or more fluids between the input ports and the output ports, and a plurality of protrusions formed on the first surface, wherein the plurality of protrusions are received in the plurality of alignment openings of the fluidic disk for aligning the fluidic chip to the fluidic disk;
an actuator operably engaging with the one or more channels at the second surface of the body for selectively and individually transferring the one or more fluids through the one or more channels from at least one of the input ports to at least one of the output ports at desired flow rates;
a tube member defining a cylindrical housing for accommodating the fluidic disk, the fluidic chip and the actuator therein;
a means for mounting a motor for operably driving the actuator to be activated or deactivated; and a means for detachably connecting the motor to the actuator, wherein the mounting means comprises a motor plate or motor support structure on which the motor is mounted; and an array plate or other support structure attached to the motor plate or motor support structure for locating the fluidic cartridge relative to the motor.

2. The fluidic cartridge of claim 1, wherein the fluidic chip comprises a one-eight-one pump chip comprising eight spiral channels that are directly, mechanically acted upon by the pump assembly's actuating elements.

3. The fluidic cartridge of claim 2, wherein the downstream terminus of each spiral channel is a bifurcation, in which that channel converges with another, similar channel, resulting a 2X channel.

4. The fluidic cartridge of claim 3, wherein the 2X channel carrying fluid from two spiral channels during pump operation has a cross-sectional area that equals the sum of the cross-sectional areas of each of its contributing channels, and thereby carrying twice the fluid volume.

5. The fluidic cartridge of claim 4, wherein the 2X channel, in turn, converges with another, similar 2X channel to form a 4X channel, whose volumetric flow rate is four times that of a 1X channel, wherein after one more bifurcation, an 8X channel delivers all the fluid being pumped through the chip to a plumbing port, which is used to connect the pump chip to an external conduit including flexible tubing.

6. The fluidic cartridge of claim 5, wherein the fluidic network upstream of the spiral channels is configured the same way as the downstream network, wherein an 8X channel begins at a plumbing port, splits into two 4X channels, and so on until the path reaches the spiral channels.

7. The fluidic cartridge of claim 2, wherein the fluidic chip utilizes eight parallel pumping channels, each end of which is connected to a binary splitter network.

8. The fluidic cartridge of claim 1, wherein the fluidic cartridge is in a cylindrical form having an axial symmetry.

9. The fluidic cartridge of claim 1, wherein the fluidic cartridge is detachable or separable from the motor.

10. The fluidic cartridge of claim 1, wherein the fluidic cartridge is portable, sterilizable replaceable, and/or disposable.

11. A fluidic system, comprising:
a plurality of fluidic cartridges disposed on a platform, each fluidic cartridge being according to claim 1, wherein the plurality of cartridges comprises pump cartridges, valve cartridges, or a combination of them.

12. A fluidic cartridge, comprising:
a fluidic disk having a plurality of alignment openings;
a fluidic chip comprising a body having a first surface and an opposite, second surface, one or more channels formed in the body in fluidic communications with input ports and output ports for transferring one or more fluids between the input ports and the output ports, and a plurality of protrusions formed on the first surface, wherein the plurality of protrusions are received in the plurality of alignment openings of the fluidic disk for aligning the fluidic chip to the fluidic disk;
an actuator operably engaging with the one or more channels at the second surface of the body for selectively and individually transferring the one or more fluids through the one or more channels from at least one of the input ports to at least one of the output ports at desired flow rates; and a tube member defining a cylindrical housing for accommodating the fluidic disk, the fluidic chip and the actuator therein,
wherein the tube member comprises:
a double-threaded tube having a first portion and a second portion extending from the first portion;
a threaded lock ring threading onto an exterior surface of the first portion of the double-threaded tube;
a fluidic compression threaded tube threading onto the exterior surface of the first portion of the double-threaded tube and abutting against the threaded lock ring.

13. The fluidic cartridge of claim 12, further comprising:
a means for mounting a motor for operably driving the actuator to be activated or deactivated; and
a means for detachably connecting the motor to the actuator.

14. The fluidic cartridge of claim 13, wherein the mounting means comprises a motor plate or motor support structure on which the motor is mounted.

15. The fluidic cartridge of claim 14, further comprising an array plate or other support structure attached to the motor plate or motor support structure for locating the fluidic cartridge relative to the motor.

16. The fluidic cartridge of claim 15, wherein the fluidic cartridge is thermally isolated from the motor.

17. The fluidic cartridge of claim 15, utilizing alignment pins and sockets to separate and reconnect the motor on the motor plate or motor support structure from the fluidic module on the array plate or other support structure.

18. The fluidic cartridge of claim 15, wherein the fluidic cartridge, once compressed, is inserted into the array plate or other fluidic module support structure and held in place with one or more tube retaining screws or other fastening means.

19. The fluidic cartridge of claim 12, further comprising:
at least a first threaded retaining ring and a second threaded retaining ring threaded into the fluidic compression threaded tube, such that the fluidic disk is placed between the first threaded retaining ring and the second threaded retaining ring that in turn, is placed between the fluidic disk and the fluidic chip.

20. The fluidic cartridge of claim 19, wherein the actuator comprises:
an actuator bearing assembly placed on the second surface of the fluidic chip; and
an actuator body operably engaging with the actuator bearing assembly.

21. The fluidic cartridge of claim 20, being a valve cartridge, wherein the actuator bearing assembly comprises:
a plurality of actuation balls; and
an actuation ball cage accommodating the plurality of actuation balls.

22. The fluidic cartridge of claim 20, being a pump cartridge, wherein the actuator bearing assembly comprises:
a plurality of actuation balls;
a sprocket accommodating the plurality of actuation balls;
a pocket accommodating the plurality of actuation balls; and
a traction ring placed on the plurality of actuation balls.

23. The fluidic cartridge of claim 20, wherein by the use of the double-threaded tube, the compression of a pump or valve is adjustable simply by rotating the fluidic compression threaded tube and locking it in place with the threaded lock ring.

24. The fluidic cartridge of claim 20, further comprising a thrust bearing placed between the motor and the actuator in the housing for supporting a compressive force that is applied by the actuator to the fluidic chip and whose double grooves maintain the axial alignment of the actuator.

25. The fluidic cartridge of claim 24, wherein the thrust bearing comprises:
a grooved lower thrust bearing race formed on an upper surface of the actuator body of the actuator;
a grooved upper thrust bearing race;
a thrust bearing ball cage placed between the lower thrust bearing race and the upper thrust bearing race;
a plurality of thrust bearing balls accommodated in the thrust bearing ball cage; and
a threaded retaining ring threaded onto an interior surface of the second portion of the double-threaded tube and positioned against the upper thrust bearing race for retaining the thrust bearing as placed in the housing.

26. The fluidic cartridge of claim 20, wherein the connecting means comprises a coupling mechanism for operably coupling the fluidic cartridge to the motor, or decoupling the fluidic cartridge from the motor.

27. The fluidic cartridge of claim 26, wherein the coupling mechanism comprises an input coupling, a torque disk, and a driven construct.

28. The fluidic cartridge of claim 27, wherein the driven construct corresponds to the actuator used directly in the operation of the fluidic cartridge.

29. The fluidic cartridge of claim 27, wherein the driven construct is a second coupling that operably mates with yet another coupling, thereby allowing further constructs to be connected to the drivetrain in a daisy chain fashion.

30. The fluidic cartridge of claim 27, wherein the coupling mechanism is an Oldham coupling mechanism comprising:
an Oldham coupling torque disk coupled to the actuator body of the actuator; and
an Oldham coupling drive disk coupled between the Oldham coupling torque disk and the motor.

31. The fluidic cartridge of claim 30, wherein the torque disk comprises an upper slot that mates with the coupling boss, and a lower t-slot that mates with a t-boss in the driven construct.

32. The fluidic cartridge of claim 31, wherein the motor side of the actuator body is provided with an Oldham coupling key having a capture key so that it holds in place the Oldham coupling torque disk when the motor plate is separated from the array plate or fluidic module support structure.

33. The fluidic cartridge of claim 30, wherein the coupling mechanism further comprises pairs of magnets that maintain the approximate axial alignment of the coupling of the torque disk to the actuator during assembly.

34. The fluidic cartridge of claim 30, further comprising an in-line gear reduction adapter operably coupled between the fluidic cartridge and the motor.

35. The fluidic cartridge of claim 34, wherein the in-line gear reduction adapter is a mechanical gear reduction adapter comprising a ring gear, sun gear, and a system of planetary gears enclosed within a tubular housing.

36. The fluidic cartridge of claim 34, wherein the in-line gear reduction adapter is a magnetic gear reduction adapter comprising an outer magnetic rotor, a rotating ferromagnetic pole element, and an inner magnetic rotor, enclosed within a tubular housing.

37. A fluidic cartridge, comprising:
a fluidic disk having a plurality of alignment openings;
a fluidic chip comprising a body having a first surface and an opposite, second surface, one or more channels formed in the body in fluidic communications with input ports and output ports for transferring one or more fluids between the input ports and the output ports, and a plurality of protrusions formed on the first surface, wherein the plurality of protrusions are received in the plurality of alignment openings of the fluidic disk for aligning the fluidic chip to the fluidic disk;
an actuator operably engaging with the one or more channels at the second surface of the body for selectively and individually transferring the one or more fluids through the one or more channels from at least one of the input ports to at least one of the output ports at desired flow rates; and
a tube member defining a cylindrical housing for accommodating the fluidic disk, the fluidic chip and the actuator therein,
wherein the plurality of protrusions is in fluidic communication with the one or more channels through interface ports formed in the plurality of protrusions for allowing connection of external tubing to the fluidic module, wherein the interface ports correspond to the input ports and the output ports.

38. The fluidic cartridge of claim 37, wherein each of the interface ports has a shoulder formed with a smaller diameter via within each interface port to prevent tubing from bottoming out against channel floors.

39. The fluidic cartridge of claim 37, being fluidically connectable to another cartridge or fluidic device through a fluidic interface connector coupled to the interface ports on the plurality of protrusions.

40. The fluidic cartridge of claim 39, wherein the fluidic interface connector is a flexible ribbon connector.

41. A continuous perfusion bioreactor, comprising:
an array of sensing and separation heads containing cell separators and media sensors, wherein each sensing and separation head is in fluidic communication with a well and a well tubing group operably connected to pumps and/or valves,
wherein the well tubing group comprises calibration and input tubes for operably delivering calibration input and media input to said sensing and separation head, a recirculation tube for operably circulating media in said sensing and separation head, and waste and media output tubes for operably removing waste output and media output from said sensing and separation head.

42. The continuous perfusion bioreactor of claim 41, wherein said pumps and/or valves comprise pump cartridges and/or valve cartridges.

43. The continuous perfusion bioreactor of claim 41, wherein each sensing and separation head comprises a normal flow filter (NFF), and/or a tangential filter comprising a tangential flow filter (TFF) or an alternating tangential flow filter (ATF).

44. The continuous perfusion bioreactor of claim 43, wherein the tangential filter is adapted for real-time separation of cells from media while minimizing filter fouling by cells, cell debris, and large molecules, wherein the fouling of the filter membrane is prevented by periodic reversal of one or more pumps.

45. The continuous perfusion bioreactor of claim 41, wherein each sensing and separation head comprises a cell separator for removing suspended cells from an effluent and returning these cells back to the continuous perfusion bioreactor while removing cell-depleted media to maintain a constant volume in the continuous perfusion bioreactor.

46. The continuous perfusion bioreactor of claim 45, wherein said cell separator is operably connected between one input pump and two output pumps that control the cell separation and recycling process.

47. The continuous perfusion bioreactor of claim 45, wherein said cell separator is a microfluidic spiral cell separator.

48. The continuous perfusion bioreactor of claim 41, wherein each sensing and separation head is in fluidic communication with said well through media/cell delivery tubes, media/cell withdrawal tubes, and emptying tubes for removal of large volumes of cells and media therefrom.

49. The continuous perfusion bioreactor of claim 41, wherein the array of sensing and separation heads is provided with a plurality of bubble tracking flow meters integrated into the continuous perfusion bioreactor.

50. The continuous perfusion bioreactor of claim 49, wherein each bubble tracking flow meter comprises two spatially separated pairs of a light-emitting diode (LED) and a photodiode (PD) operably connected between a pump and a valve operating in a coordinated manner for detecting the passage of the bubble and thereby the flow velocity.

51. The continuous perfusion bioreactor of claim 50, wherein at least one of the plurality of bubble tracking flow meters is located in one desired position in a fluidic system to measure the flow rate, and hence volume, withdrawn from a single fluidic module.

52. The continuous perfusion bioreactor of claim 41, wherein the array of sensing and separation heads is provided with a plurality of optical density (OD) measuring devices integrated into the continuous perfusion bioreactor.

* * * * *

UNITED STATES PATENT AND TRADEMARK OFFICE
CERTIFICATE OF CORRECTION

| | | |
|---|---|---|
| PATENT NO. | : 11,746,317 B2 | Page 1 of 1 |
| APPLICATION NO. | : 17/984151 | |
| DATED | : September 5, 2023 | |
| INVENTOR(S) | : Ronald S. Reiserer et al. | |

It is certified that error appears in the above-identified patent and that said Letters Patent is hereby corrected as shown below:

In the Specification

Column 1, Lines 39-52: reading:
"This invention was made with government support under Grant No. UH3TR002097 awarded by the National Institutes of Health (NIH) National Center for Advancing Translational Sciences (NCATS), National Institute of Neurological Disorders and Stroke (NINDS), and Eunice Kennedy Shriver National Institute of Child Health and Human Development (NICHD); Grant Nos. U01TR002383 and (through CFD Research Corporation) HHSN271201700044C awarded by NCATS; by the National Science Foundation (NSF) under Grant No. CBET-1706155 and Grant No. 2117782; and by the National Aeronautics and Space Administration (NASA) under Grant No. 80NSSC20K0108. The government has certain rights in the invention."

Should read as follows:
-- This invention was made with government support under Contract No. HHSN2712017000044C, and Grant Nos. TR002383, TR002243, TR002097, and CA202229, awarded by the National Institutes of Health, Grant Nos. CBET1706155 and 2117782, awarded by the National Science Foundation, and Grant No. 80NSSC20K0108, awarded by the National Aeronautics and Space Administration. The government has certain rights in the invention. --

Signed and Sealed this
Eighth Day of October, 2024

Katherine Kelly Vidal
*Director of the United States Patent and Trademark Office*